(12) United States Patent
Brand et al.

(10) Patent No.: US 10,479,792 B2
(45) Date of Patent: Nov. 19, 2019

(54) COMPOUNDS

(71) Applicants: GlaxoSmithKline Intellectual Property Development Limited, Brentford, Middlesex (GB); University of Dundee, Dundee (GB)

(72) Inventors: Stephen Brand, Dundee (GB); Peter George Dodd, Dundee (GB); Eun Jung Ko, Dundee (GB); Maria Marco Martin, Madrid (ES); Timothy James Miles, Madrid (ES); Lars Henrik Sandberg, Dundee (GB); Michael George Thomas, Dundee (GB); Stephen Thompson, Dundee (GB)

(73) Assignees: GlaxoSmithKline Intellectual Property Development Limited, Brentford (GB); University of Dundee, Dundee (GB)

( * ) Notice: Subject to any disclaimer, the term of this patent is extended or adjusted under 35 U.S.C. 154(b) by 0 days.

(21) Appl. No.: 15/750,896

(22) PCT Filed: Aug. 3, 2016

(86) PCT No.: PCT/EP2016/068592
§ 371 (c)(1),
(2) Date: Feb. 7, 2018

(87) PCT Pub. No.: WO2017/025416
PCT Pub. Date: Feb. 16, 2017

(65) Prior Publication Data
US 2018/0222911 A1 Aug. 9, 2018

(30) Foreign Application Priority Data
Aug. 7, 2015 (EP) .................................. 15382418

(51) Int. Cl.
| | | |
|---|---|---|
| *C07D 487/04* | (2006.01) | |
| *A61K 31/53* | (2006.01) | |
| *A61K 31/52* | (2006.01) | |
| *A61P 33/02* | (2006.01) | |
| *A61P 33/14* | (2006.01) | |
| *A61K 31/519* | (2006.01) | |
| *A61K 31/5377* | (2006.01) | |
| *A61K 31/553* | (2006.01) | |

(52) U.S. Cl.
CPC .......... *C07D 487/04* (2013.01); *A61K 31/519* (2013.01); *A61K 31/53* (2013.01); *A61K 31/5377* (2013.01); *A61K 31/553* (2013.01); *A61P 33/14* (2018.01); *Y02A 50/409* (2018.01); *Y02A 50/414* (2018.01); *Y02A 50/415* (2018.01)

(58) Field of Classification Search
CPC .. C07D 487/04; A61K 31/53; A61K 31/5377; A61K 31/519; A61P 33/02
USPC .................. 544/184, 281; 514/243, 259.1
See application file for complete search history.

(56) References Cited

U.S. PATENT DOCUMENTS

| | | | |
|---|---|---|---|
| 9,186,361 B2 * | 11/2015 | Chatterjee | .......... A61K 31/5377 |
| 9,303,034 B2 * | 4/2016 | Biggart | ................ C07D 487/04 |
| 2014/0274926 A1 | 9/2014 | Chatterjee et al. | |
| 2014/0275013 A1 | 9/2014 | Chatterjee et al. | |
| 2014/0275119 A1 | 9/2014 | Liang et al. | |
| 2016/0045505 A1 * | 2/2016 | Jiricek | ................. C07D 491/08 |
| | | | 514/63 |

FOREIGN PATENT DOCUMENTS

| | | |
|---|---|---|
| WO | WO 2010/059418 A1 | 5/2010 |
| WO | WO 2014/151729 A1 | 9/2014 |
| WO | WO 2014/151784 A1 | 9/2014 |
| WO | WO 2015/095477 A1 | 6/2015 |

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Proteasome inhibition for treatment of leishmaniasis, Chagas disease and sleeping sickness, by Khare, Shilpi; Nagle, Advait S.; Biggart, Agnes; Lai, Yin H.; Lang, Fang; Davis, Lauren C.; Barnes, S. Whitney; Mathison, Casey J. N.; Myburgh, Elmarie; Gao, Mu-Yun; et al. From Nature (London, United Kingdom) (2016), 537(7619), 229-233. 701:10.1038/nature19339.

(Continued)

*Primary Examiner* — Venkataraman Balasubramanian
(74) *Attorney, Agent, or Firm* — Barbara J. Carter

(57) ABSTRACT

A compound of Formula (I), or a salt thereof,

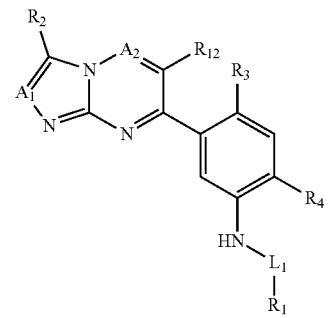

compositions comprising the compound, processes for its preparation and its use in therapy, for example in the treatment of parasitic diseases such as Chagas disease, Human African Trypanosomiasis (HAT), Animal African trypanosomiasis (AAT) and leishmaniasis, particularly visceral leishmaniasis (VL).

24 Claims, No Drawings

(56) References Cited

OTHER PUBLICATIONS

Substituted 2-Phenylimidazopyridines: A New Class of Drug Leads for Human African Trypanosomiasis. By Tatipaka, Hari Babu; Gillespie, J. Robert; Chatterjee, Amab K.; Norcross, Neil R.; Hulverson, Matthew A.; Ranade, Ranae M.; Nagendar, Pendem; Creason, Sharon A.; McQueen, Joshua; Duster, Nicole A.; et al. From Journal of Medicinal chemistry (2014), 57(3), 828-835.

β-(Oxazolo[4,5-b]pyridin-2-yl)anilides as a novel class of potent inhibitors for the kinetoplastid Trypanosoma brucei, the musative agent for human African trypanosomiasis. By Fenins, Lori; Rahmani, Raphael; Sykes, Melissa L.; Jones, Amy J.; Avery, Vicky M.; Teston, Eliott; Almohaywi, Basmah; Yin, Jie Xiang; Smith, Jason; Hyland, Chris; et al. From European Journal of Medicinal Chemistry (2013), 66, 450-465.

\* cited by examiner

COMPOUNDS

This application is a § 371 application of International Application No. PCT/EP2016/068592, filed 3 Aug. 2016, which claims the benefit of European Application No. EP15382418.0, filed 7 Aug. 2015, the disclosures of which are incorporated herein in their entireties.

TECHNICAL FIELD OF THE INVENTION

This invention provides a class of compounds, salts thereof, compositions comprising them, processes for their preparation and their use in therapy, for example in the treatment or prevention of parasitic diseases such as Chagas disease, Human African Trypanosomiasis (HAT), Animal African trypanosomiasis (AAT) and leishmaniasis, particularly visceral leishmaniasis (VL).

BACKGROUND OF THE INVENTION

Leishmaniasis

Leishmaniasis is caused in humans and animals by protozoan parasites from several *leishmania* species that are transmitted to hosts by the bites of infected female phlebotomine sandflies.

There are three main human forms of leishmaniasis—visceral (often known as kala-azar and the most serious form of the disease), cutaneous (the most common), and mucocutaneous (the most disfiguring). Most leishmaniases are zoonoses (diseases that can be transmitted from animals to humans) and the reservoir hosts include many species of mammals. Dogs are important reservoirs of *L. Infantum* responsible for visceral leishmaniasis.

Animals can also suffer from visceral, cutaneous and mucocutaneous forms of the disease.

It is estimated that 350 million people are at risk of the disease (most of them are children), with 1.3 million new cases and 20 000 to 30 000 deaths per year. (Leishmaniasis Worldwide and Global Estimates of Its Incidence. Alvar J. et al. (2012) PLoS ONE 7(5): e35671. doi:10.1371/journal.pone.0035671) Current treatments have serious drawbacks in terms of efficacy, safety, drug resistance, stability, cost and the majority lack an oral dosing option (Structures, Targets and Recent Approaches in Anti-Leishmanial Drug Discovery and Development. Seifert K., Open Med Chem J. 2011; 5:31-39. doi: 10.2174/1874104501105010031). Geographical efficacy variation in the current treatments has started to be observed—for example, the efficacy of liposomal amphotericin B in East Africa is below what is seen in the Indian sub-continent for the same dosage ((a) Berman J D, Badaro R, Thakur C P, Wasunna K M, Behbehani K, et al. (1998) Efficacy and safety of liposomal amphotericin B (AmBisome) for visceral leishmaniasis in endemic developing countries. Bull World Health Organ 76: 25-32. (b) Eltahir A. G. Khalil, Teklu Weldegebreal, Brima M. Younis et al. Safety and Efficacy of Single Dose versus Multiple Doses of AmBisome® for Treatment of Visceral Leishmaniasis in Eastern Africa: A Randomised Trial. PLOS Neglected Tropical Diseases: published 16 Jan. 2014 (info:doi/10.1371/journal.pntd.0002613). Efficacy rates are also found to vary within Africa (Hailu A, Musa A, Wasunna M, Balasegaram M, Yifru S, et al. (2010) Geographical Variation in the Response of Visceral Leishmaniasis to Paromomycin in East Africa: A Multicentre, Open-Label, Randomized Trial. PLoS Negl Trop Dis 4(10): e709. doi:10.1371/journal.pntd.0000709).

As such there is a real unmet medical need for new oral drugs and combination therapy for the treatment and potential elimination of leishmaniasis in certain geographical areas, requiring the development of multiple new oral agents.

Chagas Disease

Chagas disease is an anthropozoonosis due to the flagellated protozoan parasite *Trypanosoma cruzi*. It is transmitted to humans and other mammals by infected faeces of a blood-sucking triatominae bug through the insect sting, another skin break or through mucous membranes, including conjunctiva or oral/digestive mucosa, occasionally causing outbreaks with contaminated food. Transmission through blood transfusion, pregnancy and delivery are also possible, and less frequently, through organ transplantation or laboratory accident.

Chagas disease is endemic throughout much of Mexico, Central America, and South America where an estimated 7-8 million people are infected. The triatomine bug thrives under poor housing conditions (for example, mud walls, thatched roofs), so in endemic countries, people living in rural areas are at greatest risk for acquiring infection. The recent migration of populations from countries endemic for the disease has increased the geographic distribution of Chagas disease, so that it is now becoming an important health issue in the USA and Canada and in many parts of Europe and the western Pacific. The most common destination for migrants from Latin America is the USA, where more than three hundred thousand individuals are infected with *T. cruzi*. Spain has the second highest number of infected immigrants, an estimated sixty-seven thousand patients. Approximately thirteen thousand die each year from the complications of Chagas-induced heart disease—a result of the chronic infection.

Chagas disease presents itself in 2 phases. The initial, acute phase lasts for about 2 months after infection. During the acute phase, a high number of parasites circulate in the blood. In most cases, symptoms are absent or mild, but can include fever, headache, enlarged lymph glands, pallor, muscle pain, difficulty in breathing, swelling and abdominal or chest pain. Manifestations of the acute disease resolve spontaneously in about 90% of infected individuals even if the infection is not treated with trypanocidal drugs. About 60-70% of these patients will never develop clinically apparent disease. These patients have the indeterminate form of chronic Chagas disease, which is characterised by positivity for antibodies against *T. cruzi* in serum, a normal 12-lead electrocardiogram (ECG), and normal radiological examination of the chest, oesophagus, and colon. The remaining 30-40% of patients will subsequently develop a determinate form of chronic disease.

Up to 30% of patients with the determinate form may suffer from cardiac disorders and up to 10% from digestive (typically enlargement of the oesophagus or colon), neurological or mixed alterations or disorders. The infection can lead to sudden death or heart failure caused by progressive destruction of the heart muscle.

There is currently no vaccine for Chagas disease. Chemotherapy options are limited: benznidazole and nifurtimox are the only trypanocidal drugs available with proven efficacy against Chagas disease. Both medicines are almost 100% effective in curing the disease if given soon after infection at the onset of the acute phase. However, while studies have shown that these nitroderivatives can reduce parasitaemia in the chronic indeterminate form of the disease, clear evidence of their impact on patient-related outcomes remains elusive.

Furthermore, benznidazole and nifurtimox are not consistently used in part because of their substantial side effects (peripheral neurotoxicity, digestive system irritation and serious dermatological conditions).

Newer, safer and more efficacious treatments for Chagas disease are urgently needed.

Human African Trypanosomiasis (HAT) Human African Trypanosomiasis (HAT), also called African sleeping sickness, is a parasitic disease caused by the protozoa *Trypanosoma brucei* and transmitted by infected tsetse flies (*Glossina* spp.), from mother to child during pregnancy and can be mechanically transmitted through blood products.

Two forms of disease exist depending on the parasite sub-species:

*Trypanosoma brucei gambiense* (*T.b. gambiense*) occurring in west and central Africa, represents approximately 95% of the reported cases of sleeping sickness and causes a chronic infection. A person can be infected for months or even years without major signs or symptoms of the disease. When symptoms emerge, the patient is often already in stage 2 disease.

*Trypanosoma brucei rhodesiense* (*T.b. rhodesiense*) is found in eastern and southern Africa and represents approximately 5% of the reported cases. This sub-species of the parasite causes an acute infection. First signs and symptoms of stage 2 disease are observed a few months or weeks after infection.

The disease progresses through two distinct stages. Stage 1 is the initial haemolymphatic phase of infection and presents with non-specific symptoms including fever, rash, and fatigue. Untreated stage 1 HAT results in stage 2 disease or neurological phase, where parasites invade the central nervous system causing severe neurological symptoms and eventually death. Disturbance of the sleep cycle, which gives the disease its name, is an important feature of this second stage.

Currently four drugs are registered for the treatment of sleeping sickness. They showed different efficacy profiles depending on the *T. brucei* subspecies and the stage of the disease. The current standard treatment for stage 1 is intravenous or intramuscular pentamidine (for *T. b. gambiense*), or intravenous suramin (for *T. b. rhodesiense*). For stage 2, the front line treatment is intravenous melarsoprol, intravenous eflornithine only, or eflornithine in combination with nifurtimox. Intravenous melarsoprol in combination with oral nifurtimox may also be used. All drugs suffer from undesirable and in some cases serious adverse effects.

Safer and more efficacious treatments for HAT are urgently needed.

Animal African Trypanosomiasis (AAT)

Animal trypanosomiasis is also known as Animal African trypanosomiasis (AAT), and is a disease of vertebrate non-human animals. Human African trypanosomiasis (HAT) is commonly known as sleeping sickness. Animal trypanosomiasis is caused by various parasite species and sub-species of the *Trypanosoma* genus, trypanosomes that are pathogenic to animals, including *Trypanosoma congolense, Trypanosoma vivax, Trypanosoma brucei, Trypanosoma simiae, Trypanosoma godfreyi, Trypanosoma suis*, and *Trypanosoma evansi*. It is thought that there are likely further, un-identified trypanosome species or sub-species that are pathogenic to animals and also cause animal trypanosomiasis. Trypanosomes are protozoan parasites in the family Trypanosomatidae and most trypanosomes are transmitted by tsetse flies with the trypanosomes infecting the blood of the animal. As such, an infected animal can act as a disease reservoir with resultant potential for further disease spread in areas affected by the tsetse fly. In Africa, the disease is most common in areas affected by tsetse flies and is spread by the bite of an infected tsetse or other infected flies. Many different animals can be infected by animal trypanosomiasis, including domestic livestock, such as cattle, goats, pigs, sheep and camels. Wild animals, including elephants and leopards have also been found to have trypanosomiasis. Different parasites affect different ranges of organism. Animals are primarily at risk from this disease wherever trypanosomes and the tsetse fly vector exist, and in Africa this "tsetse belt" is between latitude 15° N and 29° S, from the southern edge of the Sahara desert to Zimbabwe, Angola and Mozambique.

In cattle the disease is frequently fatal unless treated. The symptoms include loss of condition, severe weight loss/emaciation, anaemia and fever. Current treatments for animal trypanosomiasis were introduced more than 50 years ago with isometamidium chloride, ethidium bromide and diminazene acetate forming the main treatments at present. However, as discussed by Chitanga et al, in recent years there have been increasing problems due to resistance to the presently available treatments, Chitanga et al., "High Prevalence of Drug Resistance in Animal Trypanosomes with a History of Drug Exposure". PLoS Neglected Tropical Diseases, 2011, 5, e1454.

The disease is a particular problem in sub-Saharan Africa, where it is commonly referred to as AAT, nagana, or nagana pest, and has a major effect on agriculture. In regions where herds are affected, not only are meat and milk production significantly reduced, but also the use of infected animals for vital tasks such as ploughing are compromised. Bouyer et al. "Community- and farmer-based management of animal African trypanosomiasis in cattle". Trends in Parasitology, 2013, 29, 519-522.

Thus it would be of great economic benefit to cattle farmers in regions affected by animal trypanosomiasis, and particularly farmers in sub-Saharan Africa to provide an improved treatment for AAT, an improved AAT treatment suitable for intramuscular injection, an improved AAT treatment suitable for intramuscular injections formulated as a single-dose for direct action (treatment of an infected animal) and/or prophylactic utility (uninfected animal).

Thus there is a need for new and effective anti-animal trypanosomiasis agents. In particular there is a need for new anti-animal trypanosomiasis agents which: are effective against *Trypanosoma congolense, Trypanosoma vivax, Trypanosoma brucei, Trypanosoma simiae, Trypanosoma godfreyi, Trypanosoma* suis, and/or *Trypanosoma evansi* infections; are effective against drug-resistant *Trypanosoma congolense* and/or *Trypanosoma vivax*; have transmission-blocking potential; which can be formulated for pharmaceutical or veterinary use, such as for intramuscular or oral administration; or which can be formulated for subcutaneous injection; or further which can be used for single-dose treatment; or which can be used for prophylactic treatment.

WO 2014/151784 and US 2014/0275119 disclose certain imidazopyrimidine compounds useful for treating, preventing, inhibiting, ameliorating, or eradicating the pathology and/or symptomology of a disease caused by a parasite, such as Leishmaniasis, Human African Trypanosomiasis and Chagas disease.

WO 2014/151630 and US 2014/0275013 disclose certain compounds useful for treating, preventing, inhibiting, ameliorating, or eradicating the pathology and/or symptomology of a disease caused by a parasite, such as Leishmaniasis, Human African Trypanosomiasis and Chagas disease.

WO 2015/095477 and US 2015/175613 disclose certain [1,2,4]triazolo[1,5-a]pyrimidine compounds useful for treating, preventing, inhibiting, ameliorating, or eradicating the pathology and/or symptomology of a disease caused by a parasite, such as Leishmaniasis, Human African Trypanosomiasis and Chagas disease.

US 2008/0039457 discloses certain [1,2,4]triazolo[4,3-b][1,2,4triazine compounds useful in the treatment of cancer and other diseases related to the dysregulation of kinase pathways.

SUMMARY OF THE INVENTION

The present invention provides a compound of Formula (I), or a salt thereof,

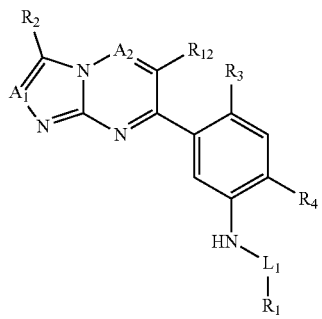

(I)

wherein
$A_1$ is CH;
$A_2$ is selected from $CR_{13}$ and N;
$R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$; wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups independently selected from hydroxy, methoxy, $C_1$-$C_3$alkyl and halo;
$L_1$ is a linker group selected from —C(O)— and —S(O)$_n$—, wherein n represents 1 to 2;
$R_3$ is selected from hydrogen, halo, methyl, methoxy and cyano;
$R_4$ is selected from hydrogen, halo, methyl, methoxy and cyano;
$R_2$ is selected from hydrogen, halo, Ar, Cy, X, $NR_{5a}R_{5b}$ and —C(O)—$R_{15}$;
Ar is selected from phenyl and $C_5$-$C_6$heteroaryl, each of which is optionally substituted with one to three groups independently selected from halo and -$L_2$-$R_7$;
$L_2$ is a linker group selected from a bond, —(CH$_2$)$_m$—, —O(CH$_2$)$_m$—, —$C_2$-$C_4$alkenyl-, —$OC_2$-$C_4$alkenyl-, —(CH$_2$)$_p$—NH—(CH$_2$)$_q$—, and —(CH$_2$)$_p$C(O)—(CH$_2$)$_q$—; wherein m represents 1 to 4 and p and q independently represent 0 to 4;
$R_7$ is selected from hydrogen; hydroxy; $NR_{8a}R_{8b}$; $C_4$-$C_7$heterocycloalkyl optionally substituted with one or two $C_1$-$C_3$alkyl groups; $C_3$-$C_7$cycloalkyl; $C_1$-$C_6$alkoxy optionally substituted with one $NR_{14a}R_{14b}$ group; and phenyl optionally substituted with one to three groups independently selected from halo, methoxy and methyl;
Cy is selected from $C_3$-$C_7$cycloalkyl, $C_4$-$C_7$heterocycloalkyl, $C_5$-$C_7$cycloalkenyl and $C_5$-$C_7$heterocycloalkenyl, each of which is optionally substituted with one to three groups independently selected from $C_1$-$C_3$alkyl, $C_1$-$C_3$alkoxy, $C_4$-$C_7$heterocycloalkyl, $NR_{11a}R_{11b}$, =O, —C(O)—$R_{15}$ and —C(O)O—$R_{15}$;
X is selected from $C_1$-$C_6$alkyl, $C_2$-$C_6$alkenyl and $C_1$-$C_6$alkoxy, each of which is optionally substituted with one to three groups independently selected from hydroxy, methoxy, halo, $NR_{13a}R_{13b}$ and $C_4$-$C_7$heterocycloalkyl, wherein $C_4$-$C_7$heterocycloalkyl is optionally substituted with one to three $C_1$-$C_3$alkyl groups;
$R_{5a}$ is selected from hydrogen; $C_1$-$C_6$alkyl optionally substituted with one group selected from Ar and Cy; —C(O)—$R_9$; —C(O)—$OR_9$; and —SO$_2$—$R_9$;
$R_{5b}$ is selected from hydrogen and $C_1$-$C_3$alkyl;
$R_{8a}$ and $R_{8b}$ are independently selected from hydrogen and $C_1$-$C_3$alkyl;
$R_9$ is selected from $C_1$-$C_6$alkyl, $C_3$-$C_7$cycloalkyl, $C_4$-$C_7$heterocycloalkyl, phenyl and $C_5$-$C_6$heteroaryl;
$R_{10a}$ and $R_{10b}$ are independently selected from hydrogen and $C_1$-$C_3$alkyl;
$R_{11a}$ and $R_{11b}$ are independently selected from hydrogen and $C_1$-$C_3$alkyl;
$R_{12}$ is selected from hydrogen, halo and methyl;
$R_{13}$ is selected from hydrogen, $C_1$-$C_3$alkyl, —C(O)—$C_4$-$C_7$heterocycloalkyl, —C(O)—$C_1$-$C_3$alkyl and —C(O)—$C_3$-$C_7$cycloalkyl;
$R_{13a}$ and $R_{13b}$ are independently selected from hydrogen and $C_1$-$C_3$alkyl;
$R_{14a}$ and $R_{14b}$ are independently selected from hydrogen and $C_1$-$C_3$alkyl; and
$R_{15}$ is selected from $C_1$-$C_6$alkyl, Ar, $C_3$-$C_7$cycloalkyl and $C_4$-$C_7$heterocycloalkyl.

The present invention is also directed to a compound of Formula (I), or a pharmaceutically acceptable salt thereof.

The present invention is also directed to a compound of Formula (I) which is

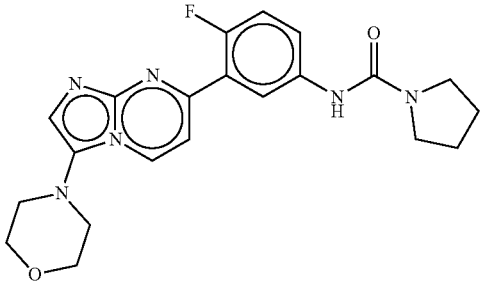

The present invention is further directed to a pharmaceutical composition comprising (a) a compound of Formula (I), or a pharmaceutically acceptable salt thereof, and (b) a pharmaceutically acceptable excipient.

The present invention is also directed to a combination comprising (a) a compound of Formula (I), or a pharmaceutically acceptable salt thereof, and (b) at least one additional therapeutic agent.

The present invention is further directed to a compound of Formula (I), or a pharmaceutically acceptable salt thereof, for use in therapy.

The present invention is also directed to a compound of Formula (I), or a pharmaceutically acceptable salt thereof, for use in the treatment or prevention of a parasitic disease selected from Chagas disease, Human African Trypanosomiasis and leishmaniasis. In one embodiment, the parasitic disease is leishmaniasis. In one embodiment, the leishmaniasis is visceral leishmaniasis. In another embodiment, the parasitic disease is Chagas disease. In another embodiment, the parasitic disease is Human African Trypanosomiasis.

The present invention is further directed to use of a compound of Formula (I), or a pharmaceutically acceptable salt thereof, in the manufacture of a medicament for the treatment or prevention of a parasitic disease selected from Chagas disease, Human African Trypanosomiasis and leishmaniasis. In one embodiment, the parasitic disease is leishmaniasis. In one embodiment, the leishmaniasis is visceral leishmaniasis. In another embodiment, the parasitic disease is Chagas disease.

There is further provided a method of treatment or prevention of a parasitic disease selected from Chagas disease, Human African Trypanosomiasis and leishmaniasis, which method comprises administering to a mammal in need thereof, a therapeutically effective amount of a compound of Formula (I), or a pharmaceutically acceptable salt thereof. In one embodiment, the mammal is a human. In another embodiment, the leishmaniasis is visceral leishmaniasis. In a further embodiment, the parasitic disease is Chagas disease.

The present invention is also directed to a compound of Formula (IA), or a salt thereof,

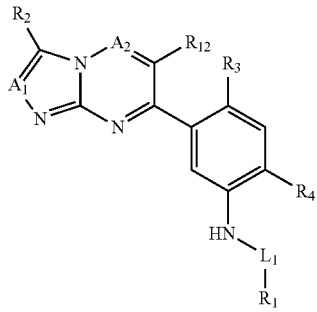

(IA)

wherein
$A_1$ is CH;
$A_2$ is selected from $CR_{13}$ and N;
$R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$; wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups selected from hydroxy, methoxy, $C_1$-$C_3$alkyl and halo;
$L_1$ is a linker group selected from —C(O)— and —S(O)$_n$—; wherein n represents 1 to 2;
$R_3$ is selected from hydrogen, halo, methyl, methoxy and cyano;
$R_4$ is selected from hydrogen, halo, methyl, methoxy and cyano;
$R_2$ is selected from hydrogen, halo, Ar, Cy, X and $NR_{5a}R_{5b}$;
Ar is selected from phenyl and $C_5$-$C_6$heteroaryl, each of which is optionally substituted with one to three groups independently selected from $NR_{6a}R_{6b}$ and -$L_2$-$R_7$;
$L_2$ is a linker group selected from a bond, —(CH$_2$)$_m$—, —O(CH$_2$)$_m$—, —$C_2$-$C_4$alkenyl- and —$OC_2$-$C_4$alkenyl-; wherein m represents 1 to 4;
$R_7$ is selected from hydrogen, $C_4$-$C_7$heterocycloalkyl, $C_3$-$C_7$cycloalkyl, $C_1$-$C_6$alkoxy, hydroxy and $NR_{8a}R_{8b}$;
Cy is selected from $C_3$-$C_7$cycloalkyl, $C_4$-$C_7$heterocycloalkyl, $C_5$-$C_7$cycloalkenyl and $C_5$-$C_7$heterocycloalkenyl, each of which is optionally substituted with one to three groups independently selected from $C_1$-$C_3$alkyl, $C_4$-$C_7$heterocycloalkyl and $NR_{11a}R_{11b}$;
X is selected from $C_1$-$C_6$alkyl, $C_2$-$C_6$alkenyl and $C_1$-$C_6$alkoxy, each of which is optionally substituted with one to three groups independently selected from hydroxy, methoxy, halo and $C_4$-$C_7$heterocycloalkyl, wherein $C_4$-$C_7$heterocycloalkyl is optionally substituted with one to three $C_1$-$C_3$alkyl groups;
$R_{5a}$ is selected from hydrogen, $C_1$-$C_6$alkyl, —C(O)—$R_9$, —C(O)—$OR_9$ and —SO$_2$—$R_9$;
$R_{5b}$ is selected from hydrogen and $C_1$-$C_3$alkyl;
$R_{6a}$ and $R_{6b}$ are independently selected from hydrogen and $C_1$-$C_3$alkyl;
$R_{8a}$ and $R_{8b}$ are independently selected from hydrogen and $C_1$-$C_6$alkyl;
$R_9$ is selected from $C_1$-$C_6$alkyl, $C_3$-$C_7$cycloalkyl, $C_4$-$C_7$heterocycloalkyl, phenyl and $C_5$-$C_6$heteroaryl;
$R_{10a}$ and $R_{10b}$ are independently selected from hydrogen and $C_1$-$C_3$alkyl;
$R_{11a}$ and $R_{11b}$ are independently selected from hydrogen and $C_1$-$C_3$alkyl;
$R_{12}$ is selected from hydrogen, halo and methyl; and
$R_{13}$ is selected from hydrogen and $C_1$-$C_3$alkyl.

The present invention is also directed to a compound of Formula (IA), or a pharmaceutically acceptable salt thereof.

The present invention is also directed to a compound of Formula (IA) which is

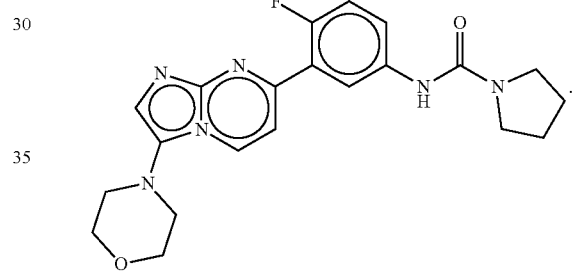

The present invention also relates to pharmaceutical compositions comprising a compound of Formula (IA), or a pharmaceutically acceptable salt thereof. Accordingly, the present invention is further directed to a pharmaceutical composition comprising a compound of Formula (IA), or a pharmaceutically acceptable salt thereof. The present invention is also directed to a pharmaceutical composition comprising (i) a compound of Formula (IA), or a pharmaceutically acceptable salt thereof; and (ii) a pharmaceutically acceptable excipient.

The present invention is also directed to a combination comprising (a) a compound of Formula (IA), or a pharmaceutically acceptable salt thereof, and (b) at least one additional therapeutic agent.

The present invention is further directed to a compound of Formula (IA), or a pharmaceutically acceptable salt thereof, for use in therapy. According to another aspect, the invention relates to a compound of Formula (IA), or a pharmaceutically acceptable salt thereof, for use in therapy, which therapy is human or veterinary.

Furthermore, the present invention also relates to a method of treatment or prevention of a parasitic disease, for example Chagas disease, Human African Trypanosomiasis, Animal African trypanosomiasis or leishmaniasis, particularly visceral leishmaniasis, which method comprises administering to a mammal in need thereof, a therapeutically effective amount of a compound of Formula (IA), or a pharmaceutically acceptable salt thereof. In one aspect, the mammal is a human. Accordingly, there is provided a method of treatment or prevention of a parasitic disease selected from Chagas disease, Human African Trypanosomiasis and leishmaniasis, which method comprises administering to a mammal in need thereof, a therapeutically effective amount of a compound of Formula (IA), or a pharmaceutically acceptable salt thereof. In one embodiment, the mammal is a human. In one embodiment, the parasitic disease is leishmaniasis. In another embodiment, the leishmaniasis is visceral leishmaniasis. In a further embodiment, the parasitic disease is Chagas disease. In a further embodiment, the parasitic disease is Human African Trypanosomiasis.

In another aspect, the invention relates to a compound of Formula (IA), or a pharmaceutically acceptable salt thereof, for use in the treatment of a parasitic disease, for example Chagas disease, Human African Trypanosomiasis, Animal African trypanosomiasis or leishmaniasis, particularly visceral leishmaniasis. Accordingly, the present invention is also directed to a compound of Formula (IA), or a pharmaceutically acceptable salt thereof, for use in the treatment or prevention of a parasitic disease selected from Chagas disease, Human African Trypanosomiasis and leishmaniasis. In one embidiment, the parasitic disease is leishmaniasis. In one embodiment, the leishmaniasis is visceral leishmaniasis. In another embodiment, the parasitic disease is Chagas disease. In a further embodiment, the parasitic disease is Human African Trypanosomiasis.

In another aspect, the invention relates to the use of a compound of Formula (IA), or a pharmaceutically acceptable salt thereof, in the manufacture of a medicament for the treatment or prevention of a parasitic disease, for example Chagas disease, Human African Trypanosomiasis, Animal African trypanosomiasis or leishmaniasis, particularly visceral leishmaniasis. Accordingly, the present invention is further directed to use of a compound of Formula (IA), or a pharmaceutically acceptable salt thereof, in the manufacture of a medicament for the treatment or prevention of a parasitic disease selected from Chagas disease, Human African Trypanosomiasis and leishmaniasis. In one embodiment, the parasitic disease is leishmaniasis. In one embodiment, the leishmaniasis is visceral leishmaniasis. In another embodiment, the parasitic disease is Chagas disease. In a further embodiment, the parasitic disease is Human African Trypanosomiasis.

DETAILED DESCRIPTION OF THE INVENTION

In a first aspect, the present invention is directed to a compound of Formula (I), or a salt thereof.

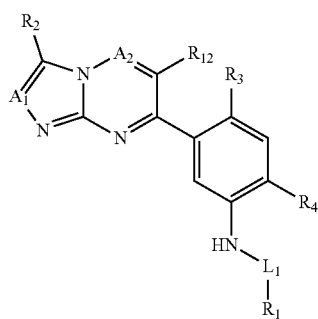

(I)

In a second aspect, the present invention is directed to a compound of Formula (I), or a pharmaceutically acceptable salt thereof.

It is to be understood that reference herein to "a compound of the invention" means a compound of Formula (I) or (IA), or a salt thereof.

Since a compound of the invention is intended for use in pharmaceutical compositions it will readily be understood that it is provided in substantially pure form, for example at least 60% pure, more suitably at least 75% pure and preferably at least 85%, especially at least 98% pure (% are on a weight for weight basis). Impure preparations of the compound of the invention may be used for preparing the more pure forms used in the pharmaceutical compositions; these less pure preparations of the compounds should contain at least 1%, more suitably at least 5% and preferably from 10 to 59% of a compound of the invention or pharmaceutically acceptable salt thereof.

In one aspect, the invention relates to a compound of Formula (I) or (IA) which is in the form of a free base. In a further aspect, the invention relates to a pharmaceutically acceptable salt of a compound of Formula (I) or (IA).

Salts of the compounds of Formula (I) or (IA) include pharmaceutically acceptable salts and salts which may not be pharmaceutically acceptable but may be useful in the preparation of compounds of Formula (I) or (IA) and pharmaceutically acceptable salts thereof. Salts may be derived from certain inorganic or organic acids or bases.

Examples of salts are pharmaceutically acceptable salts. Pharmaceutically acceptable salts include acid addition salts. For a review on suitable salts see Berge et al., *J. Pharm. Sci.*, 66:1-19 (1977).

Examples of pharmaceutically acceptable acid addition salts of a compound of Formula (I) or (IA) include inorganic acids such as, for example, hydrochloric acid, hydrobromic acid, orthophosphoric acid, nitric acid, phosphoric acid, or sulfuric acid, or with organic acids such as, for example, methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesuphonic, hexanoic acid or acetylsalicylic acid.

In one aspect of the invention, a compound of Formula (I) or (IA) is in the form of a hydrochloric acid, hydrobromic acid, orthophosphoric acid, nitric acid, phosphoric acid, or sulfuric acid salt.

Examples of pharmaceutically acceptable inorganic base addition salts of a compound of Formula (I) or (IA) include salts of ammonium, calcium, copper, ferric, ferrous, lithium, magnesium, manganic, manganous, potassium, sodium, zinc and the like.

A salt of a compound of Formula (I) or (IA) can exist in all possible stoichiometric and non-stoichiometric forms.

Salts may be formed using techniques well-known in the art, for example by precipitation from solution followed by filtration, or by evaporation of the solvent.

Salts may be prepared in situ during the final isolation and purification of the compound, or by separately reacting the purified compound in its free base form with a suitable acid or base, respectively. The salt may precipitate from solution and be collected by filtration or may be recovered by evaporation of the solvent.

Typically, a pharmaceutically acceptable acid addition salt can be formed by reaction of a compound of Formula (I) or (IA) with a suitable acid (such as hydrobromic, hydrochloric, sulfuric, maleic, p-toluenesulphonic, methanesulphonic, naphthalenesulphonic or succinic acids), optionally in a suitable solvent such as an organic solvent, to give the salt which is usually isolated for example by crystallisation and filtration.

The compound of Formula (I) or (IA) may also be prepared as the N-oxide.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Accordingly, compounds of Formula (I) or (IA) may exist as solvates. As used herein, the term solvate encompasses solvates of both a free base compound as well as any salt thereof.

Certain compounds of the invention contain chiral atoms and hence can exist in one or more (at least one) stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode. Unless otherwise specified (for example when the absolute stereochemistry is shown), for compounds of the invention which possess at least one stereocentre, and which can therefore form enantiomers, the compound can contain a mixture of enantiomers, for example a 1:1 mixture of enantiomers, i.e. a racemic mixture of enantiomers. This mixture of enantiomers may be separated using conventional techniques such as chiral HPLC. For an isomer of compound of the invention for which the absolute stereochemistry is stated or which is otherwise described as a single enantiomer, said isomer of a compound of the invention has, in one embodiment, at least 80% e.e. In another embodiment, said isomer of a compound of the invention has at least 90% e.e., for example at least 95% e.e. In another embodiment said isomer of compound of the invention corresponds to at least 98% e.e, for example at least 99% e.e.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest. In one aspect of the invention, a compound of Formula (I) or (IA) is crystalline.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

Compounds of Formula (I) or (IA) may exist in the form of isotopic variations. An isotopic variation of a compound of Formula (I) or (IA), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^2$H, $^3$H, $^{13}$C, $^{14}$C, $^{15}$N, $^{17}$O, $^{18}$O, $^{18}$F and $^{36}$Cl, respectively. Certain isotopic variations of a compound of Formula (I) or (IA) or a salt or solvate thereof, for example, those in which a radioactive isotope such as $^3$H or $^{14}$C is incorporated, are useful in drug and/or substrate tissue distribution studies. Tritium, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of a compound of Formula (I) or (IA), or a pharmaceutically salt thereof, can generally be prepared by conventional procedures such as by the illustrative methods or by the preparations described in the Examples hereafter using appropriate isotopic variations of suitable reagents.

It will be appreciated from the foregoing, that compounds of Formula (I) or (IA) and salts thereof may exist as solvates, hydrates, isomers and polymorphic forms.

It will be appreciated by those skilled in the art that certain derivatives of the compounds of Formula (I) or (IA), whilst not necessarily possessing pharmacological activity as such, may be administered and thereafter metabolised in the body to form compounds of Formula (I) or (IA) which compounds are pharmacologically active. Such derivatives are herein referred to as "prodrugs". Accordingly, a compound of Formula (I) or (IA) may exist in the form of a prodrug. Examples of suitable derivatives are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1.

Terms and Definitions

As used herein for Formula (IA), the term "$C_1$-$C_6$alkyl" means a straight or branched chain saturated hydrocarbon group (alkyl) containing at least one, and at most six, carbon atoms. Examples of $C_1$-$C_6$alkyl include, but are not limited to, methyl, ethyl, n-propyl, isopropyl, n-butyl, isobutyl, tert-butyl, pentyl, neopentyl, or hexyls.

As used herein for Formula (IA), the term "$C_1$-$C_3$alkyl" means a straight or branched alkyl containing at least one, and at most three, carbon atoms. Examples of $C_1$-$C_3$alkyl include methyl, ethyl, n-propyl and isopropyl.

As used herein for Formula (IA), the term "$C_2$-$C_6$alkenyl" means a straight or branched chain unsaturated hydrocarbon group, containing at least two, and at most six, carbon atoms, wherein the hydrocarbon group has one or more positions of unsaturation each of which is present as a double bond. Examples of $C_2$-$C_6$alkenyl include, but are not limited to, ethenyl (—CH=CH—), propenyl (—CH$_2$—CH=CH—), isopropenyl, butenyl, pentenyl, hexenyl, 1-propenyl, 2-butenyl and 2-methyl-2-butenyl.

As used herein for Formula (IA), the term "—$C_2$-$C_4$alkenyl-" means a divalent radical (acting as a linker group) of $C_2$-$C_4$alkene, which is a straight or branched chain unsaturated hydrocarbon group containing at least two, and at most four, carbon atoms wherein the hydrocarbon group has one or more positions of unsaturation each of which is present as a double bond. Examples of —$C_2$-$C_4$alkenyl- include, but are not limited to, -ethenyl-, -propenyl- and -isopropenyl-.

As used herein for Formula (IA), the term "—OC$_2$-C$_4$alkenyl-" means a divalent radical (acting as a linker group) of O—C$_2$-C$_4$alkene, wherein C$_2$-C$_4$alkene is as defined herein, and wherein one of the radicals is on the oxygen atom and the other radical is on one of the carbon atoms. Examples of —OC$_2$-C$_4$alkenyl- include, but are not limited to, -Oethenyl-, -Opropenyl- or -Oisopropenyl-.

As used herein for Formula (IA), the term "C$_1$-C$_6$alkoxy" means a straight or branched OC$_1$-C$_6$alkyl group containing at least one, and at most six, carbon atoms. Examples of C$_1$-C$_6$alkoxy include, but are not limited to, methoxy, ethoxy, n-propoxy, isopropoxy, butoxy, isobutoxy, pentoxy and hexoxy.

As used herein for Formula (IA), the term "C$_3$-C$_7$cycloalkyl" means a non-aromatic, saturated carbocyclic ring containing at least three and at most seven carbon atoms. Examples of C$_3$-C$_7$cycloalkyl groups include cyclopropyl, cyclobutyl, cyclopentyl, cyclohexyl and cycloheptyl.

As used herein for Formula (IA), the term "C$_5$-C$_7$cycloalkenyl" means a non-aromatic, unsaturated carbocyclic ring containing at least five and at most seven carbon atoms. Examples of C$_4$-C$_7$cycloalkenyl groups include cyclopentenyl, cyclohexenyl and cycloheptenyl.

As used herein for Formula (IA), the term "—OC$_3$-C$_7$cycloalkyl" means a C$_3$-C$_7$cycloalkyl group, as defined herein, attached to an oxygen atom, the oxygen atom having a radical forming a point of attachment for the —OC$_3$-C$_7$cycloalkyl group. Examples of —OC$_3$-C$_7$cycloalkyl groups include cyclopropyloxy, cyclobutyloxy, cyclopentyloxy, cyclohexyloxy and cycloheptyloxy.

As used herein for Formula (IA), the term "C$_4$-C$_7$heterocycloalkyl" means a saturated ring containing at least four and at most seven atoms, which includes one or more, for example two, ring heteroatoms selected from nitrogen, oxygen and sulfur. Examples of C$_4$-C$_7$heterocycloalkyl groups include, but are not limited to, tetrahydrofuranyl tetrahydropyranyl, tetrahydrothiopyranyl, pyrrolidinyl, tetrahydrothiophenyl, piperidinyl, piperazinyl, morpholinyl, 1,4-dioxanyl, thiomorpholinyl, 1,4-oxathianyl, 1,4-dithianyl, dioxepanyl, azepanyl, oxepanyl and diazepanyl. The point of attachment to the rest of the molecule may be by any suitable carbon or nitrogen atom.

As used herein for Formula (IA), the term "C$_5$-C$_7$heterocycloalkenyl" means a non-aromatic unsaturated ring containing at least five and at most seven atoms, which includes one or more, for example two, ring heteroatoms selected from nitrogen, oxygen and sulfur. Examples of C$_5$-C$_7$heterocycloalkenyl groups include, but are not limited to, dihydropyranyl, dihydrofuranyl, dihydrothiophenyl, pyrrolinyl, azepinyl, oxepinyl, thiepiny, dioxepinyl, dihydropyrrolyl, dihydropyrazolyl, dihydroimidazolyl, dihydrooxazolyl, dihydrothiazolyl and dihydrothiopyranyl.

As used herein for Formula (IA), the term "C$_5$-C$_6$heteroaryl" refers to an aromatic ring comprising five or six heteroatoms selected from N, O and S. Examples of C$_5$-C$_6$heteroaryl groups include, but are not limited to, furanyl, thiophenyl, pyrrolyl, pyridyl, pyrimidyl, imidazolyl and isoxazolyl.

As used herein for Formula (IA), the term "halo" refers to fluoro (F), chloro (Cl), bromo (Br) or iodo (I).

As used herein for Formula (I), the term "C$_1$-C$_6$alkyl" means a straight or branched chain saturated hydrocarbon group (alkyl) containing at least one, and at most six, carbon atoms. Examples of C$_1$-C$_6$alkyl include, but are not limited to, methyl, ethyl, n-propyl, isopropyl, n-butyl, isobutyl, tert-butyl, pentyl, neopentyl, or hexyls.

As used herein for Formula (I), the term "C$_1$-C$_3$alkyl" means a straight or branched alkyl containing at least one, and at most three, carbon atoms. Examples of C$_1$-C$_3$alkyl include methyl, ethyl, n-propyl and isopropyl.

As used herein for Formula (I), the term "C$_2$-C$_6$alkenyl" means a straight or branched chain unsaturated hydrocarbon group, containing at least two, and at most six, carbon atoms, wherein the hydrocarbon group has one or more (at least one) positions of unsaturation each of which is present as a double bond. Examples of C$_2$-C$_6$alkenyl include, but are not limited to, ethenyl (CH=CH), propenyl (CH$_2$—CH=CH), isopropenyl, butenyl, pentenyl, hexenyl, 1-propenyl, 2-butenyl and 2-methyl-2-butenyl.

As used herein for Formula (I), the term "—C$_2$-C$_4$alkenyl-" means a divalent radical (acting as a linker group) of C$_2$-C$_4$alkene, which is a straight or branched chain unsaturated hydrocarbon group containing at least two, and at most four, carbon atoms wherein the hydrocarbon group has one or more (at least one) positions of unsaturation each of which is present as a double bond. Examples of —C$_2$-C$_4$alkenyl- include, but are not limited to, -ethenyl-, -propenyl- and -isopropenyl-.

As used herein for Formula (I), the term "—OC$_2$-C$_4$alkenyl-" means a divalent radical (acting as a linker group) of O—C$_2$-C$_4$alkene, wherein C$_2$-C$_4$alkene is as defined herein, and wherein one of the radicals is on the oxygen atom and the other radical is on one of the carbon atoms. Examples of —OC$_2$-C$_4$alkenyl- include, but are not limited to, -Oethenyl-, -Opropenyl- or -Oisopropenyl-.

As used herein for Formula (I), the term "C$_1$-C$_6$alkoxy" means a straight or branched OC$_1$-C$_6$alkyl group containing at least one, and at most six, carbon atoms. Examples of C$_1$-C$_6$alkoxy include, but are not limited to, methoxy, ethoxy, n-propoxy, isopropoxy, butoxy, isobutoxy, pentoxy and hexoxy.

As used herein for Formula (I), the term "C$_3$-C$_7$cycloalkyl" means a non-aromatic, saturated carbocyclic ring containing at least three and at most seven carbon atoms. Examples of C$_3$-C$_7$cycloalkyl groups include cyclopropyl, cyclobutyl, cyclopentyl, cyclohexyl and cycloheptyl.

As used herein for Formula (I), the term "C$_5$-C$_7$cycloalkenyl" means a non-aromatic, unsaturated carbocyclic ring containing at least five and at most seven carbon atoms. Examples of C$_4$-C$_7$cycloalkenyl groups include cyclopentenyl, cyclohexenyl and cycloheptenyl.

As used herein for Formula (I), the term "—OC$_3$-C$_7$cycloalkyl" means a C$_3$-C$_7$cycloalkyl group, as defined herein, attached to an oxygen atom, the oxygen atom having a radical forming a point of attachment for the —OC$_3$-C$_7$cycloalkyl group. Examples of —OC$_3$-C$_7$cycloalkyl groups include cyclopropyloxy, cyclobutyloxy, cyclopentyloxy, cyclohexyloxy and cycloheptyloxy.

As used herein for Formula (I), the term "C$_4$-C$_7$heterocycloalkyl" means a saturated ring containing at least four and at most seven ring atoms, wherein at least one of the ring atoms is a heteroatom selected from nitrogen, oxygen and sulfur. Examples of C$_4$-C$_7$heterocycloalkyl groups include, but are not limited to, tetrahydrofuranyl tetrahydropyranyl, tetrahydrothiopyranyl, pyrrolidinyl, tetrahydrothiophenyl, piperidinyl, piperazinyl, morpholinyl, 1,4-dioxanyl, thiomorpholinyl, 1,4-oxathianyl, 1,4-dithianyl, dioxepanyl, azepanyl, oxepanyl and diazepanyl. The point of attachment to the rest of the molecule may be by any suitable carbon or nitrogen atom.

As used herein for Formula (I), the term "C$_5$-C$_7$heterocycloalkenyl" means a non-aromatic unsaturated ring containing at least five and at most seven ring atoms, wherein at least one of the ring atoms is a heteroatom selected from nitrogen, oxygen and sulfur. Examples of $C_5$-$C_7$heterocycloalkenyl groups include, but are not limited to, dihydropyranyl, dihydrofuranyl, dihydrothiophenyl, pyrrolinyl, azepinyl, oxepinyl, thiepiny, dioxepinyl, dihydropyrrolyl, dihydropyrazolyl, dihydroimidazolyl, dihydrooxazolyl, dihydrothiazolyl and dihydrothiopyranyl.

As used herein for Formula (I), the term "$C_5$-$C_6$heteroaryl" refers to an aromatic ring comprising five or six ring atoms, wherein at least one of the ring atoms is a heteroatom selected from nitrogen, oxygen and sulfur. Examples of $C_5$-$C_6$heteroaryl groups include, but are not limited to, furanyl, thiophenyl, pyrrolyl, pyridyl, pyrimidyl, imidazolyl and isoxazolyl.

As used herein for Formula (I), the term "halo" refers to fluoro (F), chloro (Cl), bromo (Br) or iodo (I).

As used herein, the term "unsaturated" means having one or more (at least one) double bonds.

In respect of Formula (I), in one aspect of the invention, $A_2$ is N. In another aspect, $A_2$ is $CR_{13}$. In another aspect, $A_2$ is CH.

In respect of Formula (I), in one aspect of the invention, $R_1$ is $C_4$-$C_7$heterocycloalkyl optionally substituted with one $C_1$-$C_3$alkyl or with one or two halo. In one aspect, R1 is pyrrolidinyl, oxazolyl or azetidinyl, each optionally substituted with one methyl or with one or two fluoro. In one aspect, R1 is pyrrolidinyl, difluroroazetidinyl, or difluoropyrrolidinyl. In another aspect, $R_1$ is pyrrolidinyl. In another aspect, $R_1$ is 1-pyrrolidinyl.

In respect of Formula (I), in one aspect of the invention, $L_1$ is selected from —C(O)— and —S(O)$_n$—; wherein n represents 2. In another aspect, $L_1$ is —C(O)—.

In respect of Formula (I), in one embodiment of the invention, $L_1$-$R_1$ is

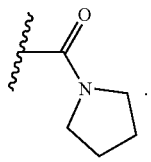 [SMILES: *C(=O)N1CCCC1]

In respect of Formula (I), in one aspect of the invention, $R_3$ is selected from hydrogen, halo, methyl and methoxy. In another aspect, $R_3$ is hydrogen or halo. In another aspect, $R_3$ is halo. In another aspect, $R_3$ is fluoro or chloro. In a further aspect, $R_3$ is fluoro.

In a yet further aspect, $R_3$ is hydrogen. In a further aspect, $R_3$ is hydrogen or fluoro.

In respect of Formula (I), in one aspect of the invention, $R_4$ is hydrogen, halo or methyl. In another aspect, $R_4$ is hydrogen.

In respect of Formula (I), in one aspect of the invention, $R_3$ is selected from fluoro, chloro, methyl, and methoxy, and $R_4$ is hydrogen; or $R_4$ is selected from fluoro, chloro, and methyl, and $R_3$ is hydrogen.

In respect of Formula (I), in one aspect of the invention, $R_2$ is selected from hydrogen, halo, Ar, Cy and X. In another aspect, $R_2$ is hydrogen.

In respect of Formula (I), in one aspect of the invention, $R_2$ is halo. In another aspect, $R_2$ is fluoro or chloro.

In respect of Formula (I), in one aspect of the invention, $R_2$ is Ar.

In respect of Formula (I), in one aspect of the invention, Ar is selected from phenyl and $C_5$-$C_6$heteroaryl, each of which is optionally substituted with one group selected from halo and -$L_2$-$R_7$.

In respect of Formula (I), in one aspect of the invention, Ar is selected from phenyl and $C_5$-$C_6$heteroaryl, each of which is optionally substituted with one group which is -$L_2$-$R_7$.

In respect of Formula (I), in one aspect of the invention, Ar is optionally substituted phenyl. In another aspect, Ar is unsubstituted phenyl.

In respect of Formula (I), in one aspect of the invention, Ar is optionally substituted $C_5$-$C_6$heteroaryl. In one aspect, Ar is optionally substituted pyridyl. In another aspect, Ar is optionally substituted 2-pyridyl. In another aspect, Ar is optionally substituted 3-pyridyl. In another aspect, Ar is optionally substituted 4-pyridyl. In one aspect of the invention, Ar is unsubstituted $C_5$-$C_6$heteroaryl.

In respect of Formula (I), in one aspect of the invention, $L_2$ is selected from a bond, —(CH$_2$)$_m$— and —O(CH$_2$)$_m$—, wherein m represents 1 to 4. In another aspect, $L_2$ is a bond. In another aspect, $L_2$ is —(CH$_2$)$_m$—. In a further aspect, $L_2$ is $C_2$-$C_4$alkenyl-. In one aspect, m represents 1 to 3.

In respect of Formula (I), in one aspect of the invention, $R_7$ is selected from hydrogen, $C_4$-$C_7$heterocycloalkyl, and $C_1$-$C_6$alkoxy. In another aspect, $R_7$ is hydrogen. In another aspect, $R_7$ is $C_4$-$C_7$heterocycloalkyl, for example morpholinyl. In another aspect, $R_7$ is $C_1$-$C_6$alkoxy, for example methoxy.

In respect of Formula (I), in one aspect of the invention, $R_2$ is Cy.

In respect of Formula (I), in one aspect of the invention, Cy is selected from $C_4$-$C_7$heterocycloalkyl and $C_5$-$C_7$heterocycloalkenyl, each of which is optionally substituted with one to three $C_1$-$C_3$alkyl groups.

In respect of Formula (I), in one aspect of the invention, Cy is selected from $C_4$-$C_7$heterocycloalkyl, and $C_5$-$C_7$heterocycloalkenyl, each of which is optionally substituted with one or two groups independently selected from $C_1$-$C_3$alkyl, $C_1$-$C_3$alkoxy, =O, —C(O)—$R_{15}$ and —C(O)O—$R_{15}$. In another aspect, Cy is selected from $C_4$-$C_7$heterocycloalkyl, and $C_5$-$C_7$heterocycloalkenyl, each of which is optionally substituted with one or two $C_1$-$C_3$alkyl groups, for example with one or two methyl groups.

In respect of Formula (I), in one aspect of the invention, Cy is optionally substituted $C_4$-$C_7$heterocycloalkyl. In another aspect, Cy is unsubstituted $C_4$-$C_7$heterocycloalkyl. In one aspect, Cy is morpholinyl. In another aspect, Cy is 4-morpholinyl.

In respect of Formula (I), in one aspect of the invention, Cy is optionally substituted $C_5$-$C_7$heterocycloalkenyl. In another aspect, Cy is unsubstituted $C_4$-$C_7$heterocycloalkenyl In respect of Formula (I), in one aspect of the invention, $R_2$ is X.

In respect of Formula (I), in one aspect of the invention, X is selected from $C_1$-$C_6$alkyl and $C_2$-$C_6$alkenyl, each of which is optionally substituted with one to three groups independently selected from hydroxy, methoxy, halo and $C_4$-$C_7$heterocycloalkyl, wherein $C_4$-$C_7$heterocycloalkyl is optionally substituted with one to three $C_1$-$C_3$alkyl groups. In another aspect, X is selected from $C_1$-$C_6$alkyl and $C_2$-$C_6$alkenyl, each of which is optionally substituted with one group selected from hydroxy, methoxy, halo and $C_4$-$C_7$heterocycloalkyl, wherein $C_4$-$C_7$heterocycloalkyl is optionally substituted with one to three $C_1$-$C_3$alkyl groups.

In respect of Formula (I), in one aspect of the invention, X is optionally substituted $C_1$-$C_6$alkyl. In another aspect, X is $C_1$-$C_6$alkyl substituted with one hydroxy group. In another aspect, X is $C_1$-$C_6$alkyl substituted with one $C_4$-$C_7$heterocycloalkyl group which is optionally substituted with one to three $C_1$-$C_3$alkyl groups. In another aspect, X is —$CH_2$— substituted with one $C_4$-$C_7$heterocycloalkyl group which is optionally substituted with one to three $C_1$-$C_3$alkyl groups. In respect of Formula (I), in one aspect, X is —$CH_2$— substituted with one $C_4$-$C_7$heterocycloalkyl group selected from morpholinyl, piperazinyl and piperidinyl, each of which is optionally substituted with one to three $C_1$-$C_3$alkyl groups, for example a methyl group. In another aspect, X is unsubstituted $C_1$-$C_6$alkyl.

In respect of Formula (I), in one aspect of the invention, X is optionally substituted $C_2$-$C_6$alkenyl. In another aspect, X is $C_2$-$C_6$alkenyl substituted with one hydroxy group. In another aspect, X is unsubstituted $C_2$-$C_6$alkenyl.

In respect of Formula (I), in one aspect of the invention, $R_{5a}$ is selected from hydrogen and $C_1$-$C_6$alkyl.

In respect of Formula (I), in one aspect of the invention, $R_{5b}$ is hydrogen.

In respect of Formula (I), in one aspect of the invention, $R_{8a}$ and $R_{8b}$ are independently selected from $C_1$-$C_3$alkyl.

In respect of Formula (I), in one aspect of the invention, $R_9$ is $C_1$-$C_6$alkyl.

In respect of Formula (I), in one aspect of the invention, $R_{10a}$ and $R_{10b}$ are independently selected from hydrogen and methyl.

In respect of Formula (I), in one aspect of the invention, $R_{11a}$ and $R_{11b}$ are independently selected from hydrogen and methyl.

In respect of Formula (I), in one aspect of the invention, $R_{12}$ is selected from hydrogen and methyl. In another aspect, $R_{12}$ is hydrogen.

In respect of Formula (I), in one aspect of the invention, $R_{13}$ is selected from hydrogen, $C_1$-$C_3$alkyl and —C(O)—$C_4$-$C_7$heterocycloalkyl. In another aspect, $R_{13}$ is selected from hydrogen, methyl and ethyl. In another aspect, $R_{13}$ is hydrogen.

In respect of Formula (I), in one aspect of the invention, $R_{12}$ is hydrogen and $R_{13}$ is selected from hydrogen and $C_1$-$C_3$alkyl. In another aspect, $R_{12}$ is hydrogen and $R_{13}$ is selected from hydrogen, methyl and ethyl. In another aspect, $R_{12}$ is methyl and $R_{13}$ is hydrogen.

In respect of Formula (I), in one aspect of the invention, $R_{15}$ is $C_1$-$C_6$alkyl.

In one aspect of the invention, there is provided a compound of Formula (I), or a salt thereof, wherein:
$A_1$ is CH;
$A_2$ is selected from $CR_{13}$ and N;
$R_1$ is $C_4$-$C_7$heterocycloalkyl, optionally substituted with one methyl or one or two halo;
$L_1$ is —C(O)—;
$R_3$ is selected from hydrogen and halo;
$R_4$ is selected from hydrogen, halo, and methyl;
$R_2$ is selected from hydrogen, halo, Ar, Cy, and X;
Ar is selected from phenyl and $C_5$-$C_6$heteroaryl, each of which is optionally substituted with one group selected from halo and and -$L_2$-$R_7$;
$L_2$ is a linker group selected from —$(CH_2)_m$— and —$O(CH_2)_m$—, wherein m represents 1;
$R_7$ is hydrogen;
Cy is $C_4$-$C_7$heterocycloalkyl, which is optionally substituted with one or two groups independently selected from methyl, methoxy, —C(O)—$R_{15}$ and —C(O)O—$R_{15}$;
X is $C_1$-$C_6$alkyl, which is optionally substituted with one $C_4$-$C_7$heterocycloalkyl group;
$R_{12}$ is selected from hydrogen, halo and methyl;
$R_{13}$ is selected from hydrogen, $C_1$-$C_3$alkyl, and —C(O)—$C_4$-$C_7$heterocycloalkyl; and
$R_{15}$ is $C_1$-$C_6$alkyl.

In one aspect of the invention, there is provided a compound of Formula (I), or a salt thereof, wherein:
$A_1$ is CH;
$A_2$ is CH;
$R_1$ is $C_4$-$C_7$heterocycloalkyl;
$L_1$ is —C(O)—;
$R_3$ is halo;
$R_4$ is hydrogen;
$R_2$ is $C_4$-$C_7$heterocycloalkyl; and
$R_{12}$ is hydrogen.

In one aspect of the invention, the compound of Formula (I) is selected from:
N-(3-(3-morpholinoimidazo[1,2-a]pyrimidin-7-yl)phenyl)pyrrolidine-1-carboxamide;
N-(3-(3-phenylimidazo[1,2-a]pyrimidin-7-yl)phenyl)pyrrolidine-1-carboxamide;
N-(4-fluoro-3-(3-phenylimidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)pyrrolidine-1-carboxamide;
N-(4-fluoro-3-(3-(piperidin-1-yl)imidazo[1,2-a]pyrimidin-7-yl)phenyl)pyrrolidine-1-carboxamide;
N-(3-(7-bromoimidazo[1,2-b][1,2,4]triazin-3-yl)-4-fluorophenyl)pyrrolidine-1-carboxamide;
N-(4-fluoro-3-(7-phenylimidazo[1,2-b][1,2,4]triazin-3-yl)phenyl)pyrrolidine-1-carboxamide;
N-(4-fluoro-3-(7-morpholinoimidazo[1,2-b][1,2,4]triazin-3-yl)phenyl)pyrrolidine-1-carboxamide;
N-(3-(7-morpholinoimidazo[1,2-b][1,2,4]triazin-3-yl)phenyl)pyrrolidine-1-carboxamide;
N-(3-(7-phenylimidazo[1,2-b][1,2,4]triazin-3-yl)phenyl)pyrrolidine-1-carboxamide;
N-(4-fluoro-3-(imidazo[1,2-b][1,2,4]triazin-3-yl)phenyl)pyrrolidine-1-carboxamide;
N-(4-fluoro-3-(5-methyl-3-morpholinoimidazo[1,2-a]pyrimidin-7-yl)phenyl)pyrrolidine-1-carboxamide;
N-(3-(5-ethyl-3-morpholinoimidazo[1,2-a]pyrimidin-7-yl)-4-fluorophenyl)pyrrolidine-1-carboxamide;
N-(3-(6-methyl-3-morpholinoimidazo[1,2-a]pyrimidin-7-yl)phenyl)pyrrolidine-1-carboxamide;
N-(4-fluoro-3-(6-methyl-3-morpholinoimidazo[1,2-a]pyrimidin-7-yl)phenyl)pyrrolidine-1-carboxamide;
N-(4-fluoro-3-(imidazo[1,2-a]pyrimidin-7-yl)phenyl)pyrrolidine-1-carboxamide;
N-(4-fluoro-3-(3-isobutylimidazo[1,2-a]pyrimidin-7-yl)phenyl)pyrrolidine-1-carboxamide;
N-(4-fluoro-3-(3-isopropylimidazo[1,2-a]pyrimidin-7-yl)phenyl)pyrrolidine-1-carboxamide;
N-(4-fluoro-3-(3-(tetrahydro-2H-pyran-4-yl)imidazo[1,2-a]pyrimidin-7-yl)phenyl)pyrrolidine-1-carboxamide;
N-(4-fluoro-3-(3-(morpholinomethyl)imidazo[1,2-a]pyrimidin-7-yl)phenyl)pyrrolidine-1-carboxamide;
N-(4-fluoro-3-(3-(4-(morpholinomethyl)phenyl)imidazo[1,2-a]pyrimidin-7-yl)phenyl)pyrrolidine-1-carboxamide;
N-(3-(3-(1,4-oxazepan-4-yl)imidazo[1,2-a]pyrimidin-7-yl)-4-fluorophenyl)pyrrolidine-1-carboxamide;
3-fluoro-N-(4-fluoro-3-(3-morpholinoimidazo[1,2-a]pyrimidin-7-yl)phenyl)pyrrolidine-1-carboxamide;
(R)-3-fluoro-N-(4-fluoro-3-(3-morpholinoimidazo[1,2-a]pyrimidin-7-yl)phenyl)pyrrolidine-1-carboxamide;
(S)-3-fluoro-N-(4-fluoro-3-(3-morpholinoimidazo[1,2-a]pyrimidin-7-yl)phenyl)pyrrolidine-1-carboxamide;
3,3-difluoro-N-(4-fluoro-3-(3-morpholinoimidazo[1,2-a]pyrimidin-7-yl)phenyl)azetidine-1-carboxamide;
3,3-difluoro-N-(4-fluoro-3-(3-morpholinoimidazo[1,2-a]pyrimidin-7-yl)phenyl)pyrrolidine-1-carboxamide;

N-(4-fluoro-3-(3-(pyridin-2-yl)imidazo[1,2-a]pyrimidin-7-yl)phenyl)pyrrolidine-1-carboxamide;
N-(4-fluoro-3-(3-(pyrazin-2-yl)imidazo[1,2-a]pyrimidin-7-yl)phenyl)pyrrolidine-1-carboxamide;
N-(4-fluoro-3-(3-(6-methoxypyridin-2-yl)imidazo[1,2-a]pyrimidin-7-yl)phenyl)pyrrolidine-1-carboxamide;
N-(4-fluoro-3-(3-(2-methylmorpholino)imidazo[1,2-a]pyrimidin-7-yl)phenyl)pyrrolidine-1-carboxamide;
N-(3-(3-(2,6-dimethylmorpholino)imidazo[1,2-a]pyrimidin-7-yl)-4-fluorophenyl)pyrrolidine-1-carboxamide;
N-(3-(3-((2S,6R)-2,6-dimethylmorpholino)imidazo[1,2-a]pyrimidin-7-yl)-4-fluorophenyl)pyrrolidine-1-carboxamide;
N-(4-fluoro-3-(3-(3-methylmorpholino)imidazo[1,2-a]pyrimidin-7-yl)phenyl)pyrrolidine-1-carboxamide;
N-(4-fluoro-3-(3-(piperazin-1-yl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)-2-methylpyrrolidine-1-carboxamide;
(R)—N-(4-fluoro-3-(3-morpholinoimidazo[1,2-a]pyrimidin-7-yl)phenyl)-2-methylpyrrolidine-1-carboxamide;
(S)—N-(4-fluoro-3-(3-morpholinoimidazo[1,2-a]pyrimidin-7-yl)phenyl)-2-methylpyrrolidine-1-carboxamide;
N-(4-fluoro-3-(3-morpholinoimidazo[1,2-a]pyrimidin-7-yl)phenyl)-3-methylpyrrolidine-1-carboxamide;
(R)—N-(4-fluoro-3-(3-morpholinoimidazo[1,2-a]pyrimidin-7-yl)phenyl)-3-methylpyrrolidine-1-carboxamide;
(S)—N-(4-fluoro-3-(3-morpholinoimidazo[1,2-a]pyrimidin-7-yl)phenyl)-3-methylpyrrolidine-1-carboxamide;
tert-butyl 4-(7-(2-fluoro-5-(pyrrolidine-1-carboxamido)phenyl)imidazo[1,2-a]pyrimidin-3-yl)piperazine-1-carboxylate;
N-(4-fluoro-3-(3-(4-methylpiperazin-1-yl)imidazo[1,2-a]pyrimidin-7-yl)phenyl)pyrrolidine-1-carboxamide;
N-(4-fluoro-3-(3-(6-methylpyridin-2-yl)imidazo[1,2-a]pyrimidin-7-yl)phenyl)pyrrolidine-1-carboxamide;
N-(4-fluoro-3-(3-(morpholin-3-yl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)-2,4-dimethyloxazole-5-carboxamide;
N-(4-fluoro-3-(3-(2-methylmorpholino)imidazo[1,2-a]pyrimidin-7-yl)phenyl)pyrrolidine-1-carboxamide;
(S)—N-(4-fluoro-3-(3-(2-methylmorpholino)imidazo[1,2-a]pyrimidin-7-yl)phenyl)pyrrolidine-1-carboxamide;
N-(3-(3-(2,2-dimethylmorpholino)imidazo[1,2-a]pyrimidin-7-yl)-4-fluorophenyl)pyrrolidine-1-carboxamide;
N-(3-(3-(3,3-dimethylmorpholino)imidazo[1,2-a]pyrimidin-7-yl)-4-fluorophenyl)pyrrolidine-1-carboxamide;
N-(4-fluoro-3-(3-(4-methylmorpholin-3-yl)imidazo[1,2-a]pyrimidin-7-yl)phenyl)pyrrolidine-1-carboxamide;
tert-butyl 3-(7-(2-fluoro-5-(pyrrolidine-1-carboxamido)phenyl)imidazo[1,2-a]pyrimidin-3-yl)morpholine-4-carboxylate;
N-(4-fluoro-3-(3-((tetrahydrofuran-2-yl)methyl)imidazo[1,2-a]pyrimidin-7-yl)phenyl)pyrrolidine-1-carboxamide;
N-(2,4-difluoro-5-(3-morpholinoimidazo[1,2-a]pyrimidin-7-yl)phenyl)pyrrolidine-1-carboxamide;
N-(4-fluoro-3-(3-(4-methoxypiperidin-1-yl)imidazo[1,2-a]pyrimidin-7-yl)phenyl)pyrrolidine-1-carboxamide;
N-(3-(3-(4-acetylpiperazin-1-yl)imidazo[1,2-a]pyrimidin-7-yl)-4-fluorophenyl)pyrrolidine-1-carboxamide;
N-(4-fluoro-3-(3-morpholinoimidazo[1,2-a]pyrimidin-7-yl)phenyl)-3-methylazetidine-1-carboxamide;
N-(4-fluoro-3-(5-(pyrrolidine-1-carbonyl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)azetidine-1-carboxamide;
N-(4-fluoro-3-(3-(3-oxopiperazin-1-yl)imidazo[1,2-a]pyrimidin-7-yl)phenyl)pyrrolidine-1-carboxamide;
N-(4-fluoro-3-(3-((tetrahydrofuran-3-yl)methyl)imidazo[1,2-a]pyrimidin-7-yl)phenyl)pyrrolidine-1-carboxamide;
N-(4-fluoro-3-(3-(6-fluoropyridin-2-yl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)tetrahydrofuran-3-carboxamide;
N-(4-fluoro-3-(3-morpholinoimidazo[1,2-a]pyrimidin-7-yl)phenyl)tetrahydrofuran-2-carboxamide; and
N-(3-(3-bromoimidazo[1,2-a]pyrimidin-7-yl)-4-fluorophenyl)pyrrolidine-1-carboxamide;
or a salt thereof.

In one aspect of the invention, the compound of Formula (I) is selected from:
N-(3-(3-morpholinoimidazo[1,2-a]pyrimidin-7-yl)phenyl)pyrrolidine-1-carboxamide;
N-(3-(3-phenylimidazo[1,2-a]pyrimidin-7-yl)phenyl)pyrrolidine-1-carboxamide;
N-(4-fluoro-3-(3-phenylimidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)pyrrolidine-1-carboxamide;
N-(4-fluoro-3-(3-(piperidin-1-yl)imidazo[1,2-a]pyrimidin-7-yl)phenyl)pyrrolidine-1-carboxamide;
N-(3-(7-bromoimidazo[1,2-b][1,2,4]triazin-3-yl)-4-fluorophenyl)pyrrolidine-1-carboxamide;
N-(4-fluoro-3-(7-phenylimidazo[1,2-b][1,2,4]triazin-3-yl)phenyl)pyrrolidine-1-carboxamide;
N-(4-fluoro-3-(7-morpholinoimidazo[1,2-b][1,2,4]triazin-3-yl)phenyl)pyrrolidine-1-carboxamide;
N-(3-(7-morpholinoimidazo[1,2-b][1,2,4]triazin-3-yl)phenyl)pyrrolidine-1-carboxamide;
N-(3-(7-phenylimidazo[1,2-b][1,2,4]triazin-3-yl)phenyl)pyrrolidine-1-carboxamide;
N-(4-fluoro-3-(imidazo[1,2-b][1,2,4]triazin-3-yl)phenyl)pyrrolidine-1-carboxamide;
N-(4-fluoro-3-(5-methyl-3-morpholinoimidazo[1,2-a]pyrimidin-7-yl)phenyl)pyrrolidine-1-carboxamide;
N-(3-(5-ethyl-3-morpholinoimidazo[1,2-a]pyrimidin-7-yl)-4-fluorophenyl)pyrrolidine-1-carboxamide;
N-(3-(6-methyl-3-morpholinoimidazo[1,2-a]pyrimidin-7-yl)phenyl)pyrrolidine-1-carboxamide;
N-(4-fluoro-3-(6-methyl-3-morpholinoimidazo[1,2-a]pyrimidin-7-yl)phenyl)pyrrolidine-1-carboxamide;
N-(4-fluoro-3-(imidazo[1,2-a]pyrimidin-7-yl)phenyl)pyrrolidine-1-carboxamide;
N-(4-fluoro-3-(3-isobutylimidazo[1,2-a]pyrimidin-7-yl)phenyl)pyrrolidine-1-carboxamide;
N-(4-fluoro-3-(3-isopropylimidazo[1,2-a]pyrimidin-7-yl)phenyl)pyrrolidine-1-carboxamide;
N-(4-fluoro-3-(3-(tetrahydro-2H-pyran-4-yl)imidazo[1,2-a]pyrimidin-7-yl)phenyl)pyrrolidine-1-carboxamide;
N-(4-fluoro-3-(3-(morpholinomethyl)imidazo[1,2-a]pyrimidin-7-yl)phenyl)pyrrolidine-1-carboxamide;
N-(4-fluoro-3-(3-(4-(morpholinomethyl)phenyl)imidazo[1,2-a]pyrimidin-7-yl)phenyl)pyrrolidine-1-carboxamide;
N-(3-(3-(1,4-oxazepan-4-yl)imidazo[1,2-a]pyrimidin-7-yl)-4-fluorophenyl)pyrrolidine-1-carboxamide;
3-fluoro-N-(4-fluoro-3-(3-morpholinoimidazo[1,2-a]pyrimidin-7-yl)phenyl)pyrrolidine-1-carboxamide;
(R)-3-fluoro-N-(4-fluoro-3-(3-morpholinoimidazo[1,2-a]pyrimidin-7-yl)phenyl)pyrrolidine-1-carboxamide;
3,3-difluoro-N-(4-fluoro-3-(3-morpholinoimidazo[1,2-a]pyrimidin-7-yl)phenyl)azetidine-1-carboxamide;
3,3-difluoro-N-(4-fluoro-3-(3-morpholinoimidazo[1,2-a]pyrimidin-7-yl)phenyl)pyrrolidine-1-carboxamide;

N-(4-fluoro-3-(3-(pyridin-2-yl)imidazo[1,2-a]pyrimidin-7-yl)phenyl)pyrrolidine-1-carboxamide;
N-(4-fluoro-3-(3-(pyrazin-2-yl)imidazo[1,2-a]pyrimidin-7-yl)phenyl)pyrrolidine-1-carboxamide;
N-(4-fluoro-3-(3-(6-methoxypyridin-2-yl)imidazo[1,2-a]pyrimidin-7-yl)phenyl)pyrrolidine-1-carboxamide;
N-(4-fluoro-3-(3-(2-methylmorpholino)imidazo[1,2-a]pyrimidin-7-yl)phenyl)pyrrolidine-1-carboxamide;
N-(3-(3-(2,6-dimethylmorpholino)imidazo[1,2-a]pyrimidin-7-yl)-4-fluorophenyl)pyrrolidine-1-carboxamide;
N-(3-(3-((2S,6R)-2,6-dimethylmorpholino)imidazo[1,2-a]pyrimidin-7-yl)-4-fluorophenyl)pyrrolidine-1-carboxamide;
N-(4-fluoro-3-(3-(3-methylmorpholino)imidazo[1,2-a]pyrimidin-7-yl)phenyl)pyrrolidine-1-carboxamide;
N-(4-fluoro-3-(3-(piperazin-1-yl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)-2-methylpyrrolidine-1-carboxamide;
(R)—N-(4-fluoro-3-(3-morpholinoimidazo[1,2-a]pyrimidin-7-yl)phenyl)-2-methylpyrrolidine-1-carboxamide;
N-(4-fluoro-3-(3-morpholinoimidazo[1,2-a]pyrimidin-7-yl)phenyl)-3-methylpyrrolidine-1-carboxamide;
(R)—N-(4-fluoro-3-(3-morpholinoimidazo[1,2-a]pyrimidin-7-yl)phenyl)-3-methylpyrrolidine-1-carboxamide;
(S)—N-(4-fluoro-3-(3-morpholinoimidazo[1,2-a]pyrimidin-7-yl)phenyl)-3-methylpyrrolidine-1-carboxamide;
tert-butyl 4-(7-(2-fluoro-5-(pyrrolidine-1-carboxamido)phenyl)imidazo[1,2-a]pyrimidin-3-yl)piperazine-1-carboxylate;
N-(4-fluoro-3-(3-(4-methylpiperazin-1-yl)imidazo[1,2-a]pyrimidin-7-yl)phenyl)pyrrolidine-1-carboxamide;
N-(4-fluoro-3-(3-(6-methylpyridin-2-yl)imidazo[1,2-a]pyrimidin-7-yl)phenyl)pyrrolidine-1-carboxamide;
N-(4-fluoro-3-(3-(morpholin-3-yl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)-2,4-dimethyloxazole-5-carboxamide;
N-(4-fluoro-3-(3-(2-methylmorpholino)imidazo[1,2-a]pyrimidin-7-yl)phenyl)pyrrolidine-1-carboxamide;
(S)—N-(4-fluoro-3-(3-(2-methylmorpholino)imidazo[1,2-a]pyrimidin-7-yl)phenyl)pyrrolidine-1-carboxamide;
N-(3-(3-(2,2-dimethylmorpholino)imidazo[1,2-a]pyrimidin-7-yl)-4-fluorophenyl)pyrrolidine-1-carboxamide;
N-(3-(3-(3,3-dimethylmorpholino)imidazo[1,2-a]pyrimidin-7-yl)-4-fluorophenyl)pyrrolidine-1-carboxamide;
N-(4-fluoro-3-(3-(4-methylmorpholin-3-yl)imidazo[1,2-a]pyrimidin-7-yl)phenyl)pyrrolidine-1-carboxamide;
tert-butyl 3-(7-(2-fluoro-5-(pyrrolidine-1-carboxamido)phenyl)imidazo[1,2-a]pyrimidin-3-yl)morpholine-4-carboxylate;
N-(4-fluoro-3-(3-((tetrahydrofuran-2-yl)methyl)imidazo[1,2-a]pyrimidin-7-yl)phenyl)pyrrolidine-1-carboxamide;
N-(2,4-difluoro-5-(3-morpholinoimidazo[1,2-a]pyrimidin-7-yl)phenyl)pyrrolidine-1-carboxamide;
N-(4-fluoro-3-(3-(4-methoxypiperidin-1-yl)imidazo[1,2-a]pyrimidin-7-yl)phenyl)pyrrolidine-1-carboxamide;
N-(3-(3-(4-acetylpiperazin-1-yl)imidazo[1,2-a]pyrimidin-7-yl)-4-fluorophenyl)pyrrolidine-1-carboxamide;
N-(4-fluoro-3-(3-morpholinoimidazo[1,2-a]pyrimidin-7-yl)phenyl)-3-methylazetidine-1-carboxamide;
N-(4-fluoro-3-(5-(pyrrolidine-1-carbonyl)imidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)azetidine-1-carboxamide; and
N-(4-fluoro-3-(3-(3-oxopiperazin-1-yl)imidazo[1,2-a]pyrimidin-7-yl)phenyl)pyrrolidine-1-carboxamide;
or a salt thereof.

In one aspect of the invention, the compound of Formula (I) is selected from:
N-(3-(3-morpholinoimidazo[1,2-a]pyrimidin-7-yl)phenyl)pyrrolidine-1-carboxamide;
N-(3-(3-phenylimidazo[1,2-a]pyrimidin-7-yl)phenyl)pyrrolidine-1-carboxamide;
N-(4-fluoro-3-(3-phenylimidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)pyrrolidine-1-carboxamide;
N-(4-fluoro-3-(3-(piperidin-1-yl)imidazo[1,2-a]pyrimidin-7-yl)phenyl)pyrrolidine-1-carboxamide;
N-(3-(7-bromoimidazo[1,2-b][1,2,4]triazin-3-yl)-4-fluorophenyl)pyrrolidine-1-carboxamide;
N-(4-fluoro-3-(7-phenylimidazo[1,2-b][1,2,4]triazin-3-yl)phenyl)pyrrolidine-1-carboxamide;
N-(4-fluoro-3-(7-morpholinoimidazo[1,2-b][1,2,4]triazin-3-yl)phenyl)pyrrolidine-1-carboxamide;
N-(3-(7-morpholinoimidazo[1,2-b][1,2,4]triazin-3-yl)phenyl)pyrrolidine-1-carboxamide;
and
N-(3-(7-phenylimidazo[1,2-b][1,2,4]triazin-3-yl)phenyl)pyrrolidine-1-carboxamide;
or a salt thereof.

In one aspect of the invention, the compound of Formula (I) is N-(4-fluoro-3-(3-morpholinoimidazo[1,2-a]pyrimidin-7-yl)phenyl)pyrrolidine-1-carboxamide or a salt thereof.

In one aspect of the invention, the compound of Formula (I) is N-(4-fluoro-3-(3-morpholinoimidazo[1,2-a]pyrimidin-7-yl)phenyl)pyrrolidine-1-carboxamide.

In one aspect of the invention, the compound of Formula (I) is

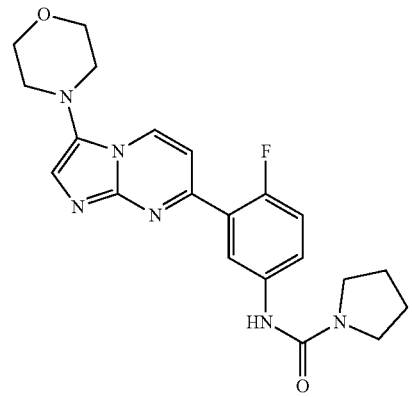 [SMILES: O=C(Nc1ccc(F)c(-c2ccn3c(N4CCOCC4)cnc3n2)c1)N1CCCC1]

or a salt thereof.

In one aspect of the invention, the compound of Formula (I) is

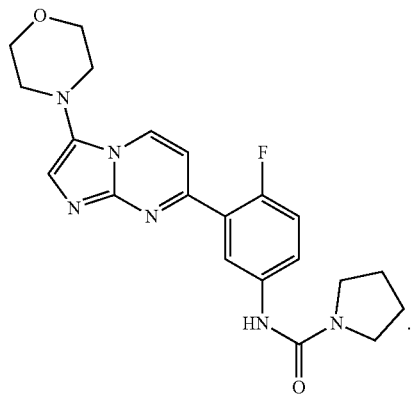 [SMILES: O=C(Nc1ccc(F)c(-c2ccn3c(N4CCOCC4)cnc3n2)c1)N1CCCC1]

In respect of Formula (IA), i one aspect of the invention, $A_2$ is N. In another aspect, $A_2$ is $CR_{13}$.

In respect of Formula (IA), in one aspect of the invention, $R_1$ is $C_4$-$C_6$heterocycloalkyl. In another aspect, $R_1$ is pyrrolidinyl.

In respect of Formula (IA), in one aspect of the invention, $L_1$ is selected from —C(O)— and —S(O)$_n$—; wherein n represents 2. In another aspect, $L_1$ is —C(O)—.

In respect of Formula (IA), in one aspect of the invention, $R_3$ is hydrogen or halo. In another aspect, $R_3$ is halo. In another aspect, $R_3$ is fluoro or chloro. In a further aspect, $R_3$ is fluoro. In a yet further aspect, $R_3$ is hydrogen. In a further aspect, $R_3$ is hydrogen or fluoro.

In respect of Formula (IA), in one aspect of the invention, $R_4$ is hydrogen.

In respect of Formula (IA), in one aspect of the invention, $R_2$ is hydrogen.

In respect of Formula (IA), in one aspect of the invention, $R_2$ is halo. In another aspect, $R_2$ is fluoro or chloro.

In respect of Formula (IA), in one aspect of the invention, $R_2$ is $NR_{5a}R_{5b}$.

In respect of Formula (IA), in one aspect of the invention, $R_2$ is Ar.

In respect of Formula (IA), in one aspect of the invention, Ar is selected from phenyl and $C_5$-$C_6$heteroaryl, each of which is optionally substituted with one group selected from $NR_{6a}R_{6b}$ and -$L_2$-$R_7$.

In respect of Formula (IA), in one aspect of the invention, Ar is selected from phenyl and $C_5$-$C_6$heteroaryl, each of which is optionally substituted with one group which is $NR_{6a}R_{6b}$.

In respect of Formula (IA), in one aspect of the invention, Ar is selected from phenyl and $C_5$-$C_6$heteroaryl, each of which is optionally substituted with one group which is -$L_2$-$R_7$.

In respect of Formula (IA), in one aspect of the invention, Ar is optionally substituted phenyl. In another aspect, Ar is unsubstituted phenyl.

In respect of Formula (IA), in one aspect of the invention, Ar is optionally substituted $C_5$-$C_6$heteroaryl. In one aspect, Ar is optionally substituted pyridyl. In another aspect, Ar is optionally substituted 2-pyridyl. In another aspect, Ar is optionally substituted 3-pyridyl. In another aspect, Ar is optionally substituted 4-pyridyl. In one aspect of the invention, Ar is unsubstituted $C_5$-$C_6$heteroaryl.

In respect of Formula (IA), in one aspect of the invention, $L_2$ is selected from a bond, —(CH$_2$)$_m$— and —O(CH$_2$)$_m$—, wherein m represents 1 to 4. In another aspect, $L_2$ is a bond. In another aspect, $L_2$ is —(CH$_2$)$_m$—. In a further aspect, $L_2$ is $C_2$-$C_4$alkenyl-. In one aspect, m represents 1 to 3.

In respect of Formula (IA), in one aspect of the invention, $R_7$ is selected from hydrogen, $C_4$-$C_7$heterocycloalkyl, and $C_1$-$C_6$alkoxy. In another aspect, $R_7$ is hydrogen. In another aspect, $R_7$ is $C_4$-$C_7$heterocycloalkyl, for example morpholinyl. In another aspect, $R_7$ is $C_1$-$C_6$alkoxy, for example methoxy.

In respect of Formula (IA), in one aspect of the invention, $R_2$ is Cy.

In respect of Formula (IA), in one aspect of the invention, Cy is selected from $C_4$-$C_7$heterocycloalkyl and $C_5$-$C_7$heterocycloalkenyl, each of which is optionally substituted with one to three $C_1$-$C_3$alkyl groups.

In respect of Formula (IA), in one aspect of the invention, Cy is selected from $C_4$-$C_7$heterocycloalkyl, and $C_5$-$C_7$heterocycloalkenyl, each of which is optionally substituted with one or two $C_1$-$C_3$alkyl groups, for example with one or two methyl groups.

In respect of Formula (IA), in one aspect of the invention, Cy is optionally substituted $C_4$-$C_7$heterocycloalkyl. In another aspect, Cy is unsubstituted $C_4$-$C_7$heterocycloalkyl. In one aspect, Cy is morpholinyl.

In respect of Formula (IA), in one aspect of the invention, Cy is optionally substituted $C_5$-$C_7$heterocycloalkenyl. In another aspect, Cy is unsubstituted $C_4$-$C_7$heterocycloalkenyl.

In respect of Formula (IA), in one aspect of the invention, $R_2$ is X.

In respect of Formula (IA), in one aspect of the invention, X is selected from $C_1$-$C_6$alkyl and $C_2$-$C_6$alkenyl, each of which is optionally substituted with one to three groups independently selected from hydroxy, methoxy, halo and $C_4$-$C_7$heterocycloalkyl, wherein $C_4$-$C_7$heterocycloalkyl is optionally substituted with one to three $C_1$-$C_3$alkyl groups. In another aspect, X is selected from $C_1$-$C_6$alkyl and $C_2$-$C_6$alkenyl, each of which is optionally substituted with one group selected from hydroxy, methoxy, halo and $C_4$-$C_7$heterocycloalkyl, wherein $C_4$-$C_7$heterocycloalkyl is optionally substituted with one to three $C_1$-$C_3$alkyl groups.

In respect of Formula (IA), in one aspect of the invention, X is optionally substituted $C_1$-$C_6$alkyl. In another aspect, X is $C_1$-$C_6$alkyl substituted with one hydroxy group. In another aspect, X is $C_1$-$C_6$alkyl substituted with one $C_4$-$C_7$heterocycloalkyl group which is optionally substituted with one to three $C_1$-$C_3$alkyl groups. In another aspect, X is —CH$_2$— substituted with one $C_4$-$C_7$heterocycloalkyl group which is optionally substituted with one to three $C_1$-$C_3$alkyl groups.

In respect of Formula (IA), in one aspect, X is —CH$_2$— substituted with one $C_4$-$C_7$heterocycloalkyl group selected from morpholinyl, piperazinyl and piperidinyl, each of which is optionally substituted with one to three $C_1$-$C_3$alkyl groups, for example a methyl group. In another aspect, X is unsubstituted $C_1$-$C_6$alkyl.

In respect of Formula (IA), in one aspect of the invention, X is optionally substituted $C_2$-$C_6$alkenyl. In another aspect, X is $C_2$-$C_6$alkenyl substituted with one hydroxy group. In another aspect, X is unsubstituted $C_2$-$C_6$alkenyl.

In respect of Formula (IA), in one aspect of the invention, $R_{5a}$ is selected from hydrogen and $C_1$-$C_6$alkyl.

In respect of Formula (IA), in one aspect of the invention, $R_{5b}$ is hydrogen.

In respect of Formula (IA), in one aspect of the invention, $R_{6a}$ and $R_{6b}$ are independently selected from $C_1$-$C_3$alkyl. In another aspect, $R_6$ and $R_{6b}$ are both methyl.

In respect of Formula (IA), in one aspect of the invention, $R_{8a}$ and $R_{8b}$ are independently selected from $C_1$-$C_6$alkyl.

In respect of Formula (IA), in one aspect of the invention, $R_9$ is $C_1$-$C_6$alkyl.

In respect of Formula (IA), in one aspect of the invention, $R_{10a}$ and $R_{10b}$ are independently selected from hydrogen and methyl.

In respect of Formula (IA), in one aspect of the invention, $R_{11a}$ and $R_{11b}$ are independently selected from hydrogen and methyl.

In respect of Formula (IA), in one aspect of the invention, $R_{12}$ is selected from hydrogen and methyl. In another aspect, $R_{12}$ is hydrogen.

In respect of Formula (IA), in one aspect of the invention, $R_{13}$ is selected from hydrogen, methyl and ethyl. In another aspect, $R_{13}$ is hydrogen.

In one aspect of the invention, the compound of Formula (I) or (IA) is selected from:

N-(3-(3-morpholinoimidazo[1,2-a]pyrimidin-7-yl)phenyl)pyrrolidine-1-carboxamide;

N-(3-(3-phenylimidazo[1,2-a]pyrimidin-7-yl)phenyl)pyrrolidine-1-carboxamide;
N-(4-fluoro-3-(3-phenylimidazo[1,2-a]pyrimidin-7-yl)phenyl)pyrrolidine-1-carboxamide;
N-(4-fluoro-3-(3-morpholinoimidazo[1,2-a]pyrimidin-7-yl)phenyl)pyrrolidine-1-carboxamide;
N-(4-fluoro-3-(3-(piperidin-1-yl)imidazo[1,2-a]pyrimidin-7-yl)phenyl)pyrrolidine-1-carboxamide;
N-(3-(7-bromoimidazo[1,2-b][1,2,4]triazin-3-yl)-4-fluorophenyl)pyrrolidine-1-carboxamide;
N-(4-fluoro-3-(7-phenylimidazo[1,2-b][1,2,4]triazin-3-yl)phenyl)pyrrolidine-1-carboxamide;
N-(4-fluoro-3-(7-morpholinoimidazo[1,2-b][1,2,4]triazin-3-yl)phenyl)pyrrolidine-1-carboxamide
N-(3-(7-morpholinoimidazo[1,2-b][1,2,4]triazin-3-yl)phenyl)pyrrolidine-1-carboxamide;
N-(3-(7-phenylimidazo[1,2-b][1,2,4]triazin-3-yl)phenyl)pyrrolidine-1-carboxamide;
N-(3-(3-morpholino-[1,2,4]triazolo[4,3-a]pyrimidin-7-yl)phenyl)pyrrolidine-1-carboxamide;
or a salt thereof.

Compound Preparation

A compound of Formula (I) or (IA) and salts thereof, may be prepared by the methodology described hereinafter, constituting further aspects of this invention.

The general procedures which can be used to synthesise a compound of Formula (I) or (IA) are summarised in reaction Schemes 1 to 3, and are illustrated in the Examples.

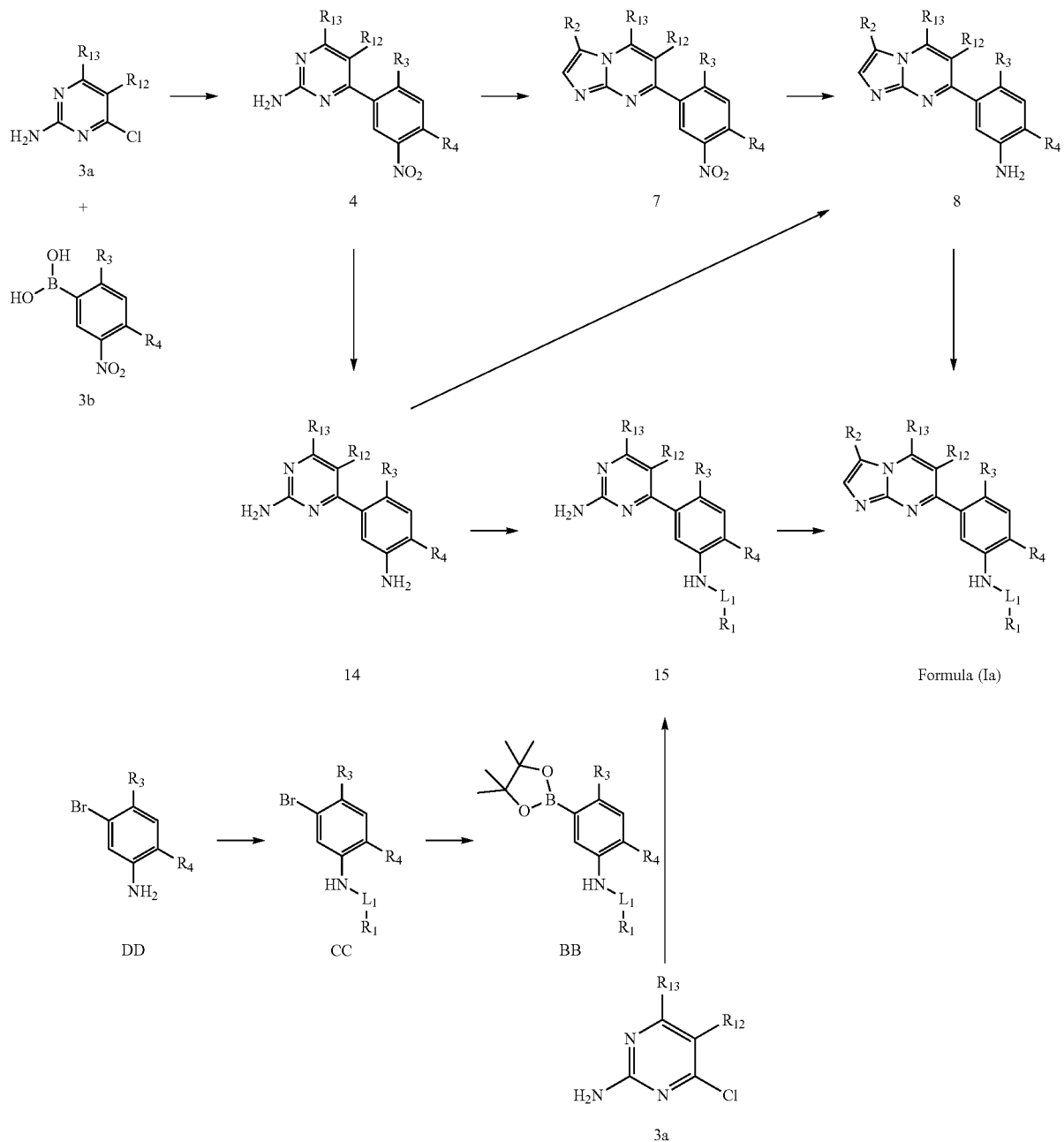

Scheme 1

Compounds of Formula (Ia), which are compounds of Formula (I) or (IA) wherein $A_1$ is CH and $A_2$ is $CR_{13}$, may be prepared according to the procedure in Scheme 1.

Compounds of Formula (Ia), wherein $R_2$ is Ar, $C_4$-$C_7$heterocycloalkyl, $C_5$-$C_7$heterocycloalkenyl, $NR_{5a}R_{5b}$ or X, may be obtained by reaction of Compounds of Formula (Ia), wherein $R_2$ is bromo, with $R_2$—Y, wherein $R_2$ is Ar, $C_4$-$C_7$heterocycloalkyl, $C_5$-$C_7$heterocycloalkenyl $NR_{5a}R_{5b}$ or X, and Y is hydrogen or a boronic acid or ester, for example tetrafluoroborate.

For example, when $R_2$—Y is morpholine, pyrrolidine or piperidine (Y is hydrogen), reaction may be carried out by means of sonication or under microwaves.

For example, when $R_2$—Y is $HNR_{5a}R_{5b}$, the reaction may be carried out using a coupling reaction in the presence of a palladium agent such as tris(dibenzylideneacetone)-dipalladium(0) and a suitable base, such as lithium bis(trimethylsilyl)amide and a suitable ligand, for example palladium(ii) phenethylamine chloride.

For example, when $R_2$—Y is X—H, reaction with compound (Ia), wherein $R_2$ is bromo, may be carried out by means of a coupling reaction, in the presence of a suitable palladium agent, such as palladium acetate.

In another alternative, Compounds of Formula (Ia) may be obtained by reacting Compounds of Formula 8, wherein $R_3$, $R_4$, $R_{12}$ and $R_{13}$ are as defined for Formula (I) or (IA), with $R_1(L_1)Cl$, wherein $L_1$ and $R_1$ are as defined for Formula (I) or (IA), in the presence of a suitable base, in a suitable solvent, such as DCM:pyridine, wherein pyridine is both a co-solvent and a base, or using a base such as $Et_3N$ in a suitable solvent, such as 1,2-dichloroethane.

For example, when $R_1(L_1)Cl$ is $R_1C(O)Cl$, wherein $R_1$ is as defined for Formula (I) or (IA), the reaction may be carried out in a suitable base such as dimethylaminopyridine in pyridine, in a suitable solvent such as DCM, at elevated temperature, or alternatively Compounds 8 may be reacted with triphosgene in a suitable solvent such as 1,2-dichloroethane, followed by reaction with $R_1$—H, for example pyrrolidine, in the presence of a suitable base such as $Et_3N$.

$R_1(L_1)Cl$ may either be commercially available or can be made using standard procedures, for example from $R_1C(O)OH$, which in turn is either commercially available or can be made using standard procedures.

Compounds of Formula 8 may be prepared from Compounds of Formula 7, wherein $R_2$ is selected from hydrogen, halo, Ar, Cy, $NR_{5a}R_{5b}$, $C_1$-$C_6$alkyl, or $C_1$-$C_6$alkoxy; $R_3$, $R_4$, $R_{12}$ and $R_{13}$ are as defined for Formula (I) or (IA), by reduction of the nitro group of Compound 7 to an amine group, using a suitable reducing agent. For example, Compound 7 may be reacted with iron in ammonium chloride in a suitable solvent such as EtOH and water, under elevated temperature.

Alternatively, Compounds of Formula 8 may be prepared by means of a cyclisation reaction between Compounds of Formula 14, wherein $R_1$, $R_3$, $R_4$, $R_{12}$ and $R_{13}$ are as defined for Formula (I) or (IA), and suitable reagents, in an analogous process to the preparation of Compounds of Formula 7 or Compounds of Formula (I) or (IA) from Compound 15.

Compounds of Formula 7 may be prepared by means of a cyclisation reaction between Compounds of Formula 4, wherein; $R_3$, $R_4$ $R_{12}$ and $R_{13}$ are as defined for Formula (I) or (IA), and suitable reagents. For example, when $R_2$ is Ar, the reagent may be $ArCH(Br)C(O)H$, wherein Ar is as defined for Formula (I) or (IA), in the presence of a suitable solvent such as DCE or acetonitrile. When $R_2$ is N-linkedCy the reagent may be [(N-linkedCy)(Bt)CH-]$_2$, wherein N-linkedCy is Cy as defined for Formula (I) or (IA) wherein Cy contains a nitrogen atom which is linked to the rest of the molecule, in the presence of a suitable catalyst such as an metal halide, for example zinc bromide.

Compounds of Formula 4 may be prepared by means of a coupling reaction between Compounds of Formula 3a, wherein $R_{12}$ is selected from hydrogen and methyl and $R_{13}$ is as defined for Formula (I) or (IA), and boronic acid Compounds of Formula 3b, wherein $R_3$ is selected from hydrogen, methyl, methoxy and cyano, and $R_4$ is selected from hydrogen, methyl, methoxy and cyano, in the presence of a suitable catalyst such as a palladium catalyst, for example $Pd(PPh_3)_4$ and a suitable base such as $NaHCO_3$, in a suitable solvent such as dioxane, under elevated temperature.

Compounds of Formula 3a and 3b may either be purchased, for example from ALDRICH, or can be made using standard procedures.

In a further alternative, Compounds of Formula (Ia) may be by means of a cyclisation reaction between Compounds of Formula 15, wherein $R_1$, $R_3$, $R_4$, $R_{12}$ and $R_{13}$ are as defined for Formula (I) or (IA), and suitable reagents. For example, when $R_2$ is Ar, the reagent may be $ArCH(Br)C(O)H$, wherein Ar is as defined for Formula (I) or (IA), in the presence of a suitable solvent such as DCE or acetonitrile. When $R_2$ is N-linkedCy, the reagent may be [(N-linkedCy)(Bt)CH-]$_2$, wherein N-linkedCy is Cy as defined for Formula (I) or (IA) wherein Cy contains a nitrogen atom which is linked to the rest of the molecule, in the presence of a suitable catalyst such as an metal halide, for example zinc bromide.

Compounds of Formula 15 may be obtained by reacting of Formula 14, wherein $R_3$, $R_4$, $R_{12}$ and $R_{13}$ are as defined for Formula (I) or (IA), with $R_1(L_1)Cl$, wherein $L_1$ and $R_1$ are as defined for Formula (I) or (IA), in the presence of a suitable base, in a suitable solvent, such as DCM:pyridine, wherein pyridine is both a co-solvent and a base, or using a base such as $Et_3N$ in a suitable solvent, such as 1,2-dichloroethane.

For example, when $R_1(L_1)Cl$ is $R_1C(O)Cl$, wherein $R_1$ is as defined for Formula (I) or (IA), the reaction may be carried out in a suitable base such as dimethylaminopyridine in pyridine, in a suitable solvent such as DCM, at elevated temperature, or alternatively Compounds 14 may be reacted with triphosgene in a suitable solvent such as 1,2-dichloroethane, followed by reaction with $R_1$—H, for example pyrrolidine, in the presence of a suitable base such as $Et_3N$.

$R_1(L_1)Cl$ may either be commercially available or can be made using standard procedures, for example from $R_1C(O)OH$, which in turn is either commercially available or can be made using standard procedures.

Compounds of Formula 14 may be obtained from Compounds of Formula 4, wherein $R_3$, $R_4$ $R_{12}$ and $R_{13}$ are as defined for Formula (I) or (IA), by reduction of the nitro group of Compound 4 to an amine group, using a suitable reducing agent. For example, Compound 4 may be reacted with iron in ammonium chloride in a suitable solvent such as a mixture of water, 1,4-dioxane and EtOH, under elevated temperature.

Alternatively, Compounds of Formula 15 may be obtained by means of a coupling reaction between Compounds of Formula 3a, wherein $R_{12}$ and $R_{13}$ are as defined for Formula (I), and boronate esters of Formula BB, wherein $R_3$, $R_4$, $L_1$, and $R_1$ are as defined for Formula (I), in the presence of a suitable catalyst such as a palladium catalyst, for example Pd(PPh$_3$)$_4$, and a suitable base such as Na$_2$CO$_3$, in a suitable solvent such as dioxane, under elevated temperature.

Compounds of Formula BB can be prepared by means of borylation procedures from Compounds of Formula CC, in the presence of a suitable catalyst such as a palladium catalyst, for example Pd$_2$(dba)$_3$, and a ligand such as XPhos, a suitable base such as KOAc, in a suitable solvent such as dioxane, under elevated temperature.

Compounds of Formula CC may be obtained from Compounds of Formula DD, wherein $R_3$ and $R_4$ are the same as defined for Formula (I), by means of standard urea preparation conditions, such as reaction with 1,1'-carbonyldiimidazole in the presence of a suitable base, such as DIPEA, using DCM as solvent, followed by reaction of the corresponding $R_1$, using a suitable solvent, such as DCM, for example at RT.

Compounds of Formula 3a may either be commercially available or can be made using standard procedures.

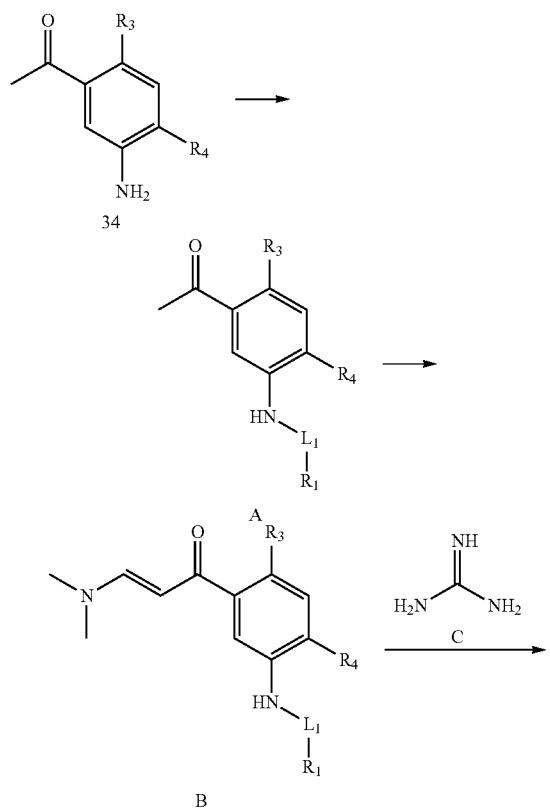

Scheme 1a

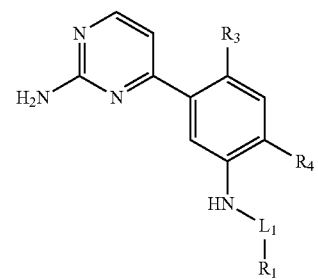

15

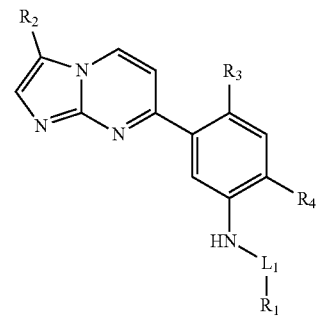

Formula I

Compounds of Formula 15 may alternatively be prepared by means of a cyclisation reaction between Compounds of Formula B, wherein $R_1$, $R_3$ and $R_4$ are as defined for Formula (I) or (IA), and compound of Formula C (guanidine carbonate), heating the mixture in the presence of a suitable base, e.g. MeONa, in a suitable solvent, e.g. MeOH. The Compound of Formula C (guanidine carbonate) may act as both reagent and base. Preferably, the guanidine carbonate (Formula C) acts as both reagent and base, the solvent is ethanol, and the reaction is heated to 80° C. overnight.

Compounds of Formula B may be prepared from Compounds of Formula A, wherein $R_1$, $R_3$ and $R_4$ are as defined for Formula (I) or (IA), by means of enamine formation reaction, e.g. using DMF-DMA as a source for N, N-dimethylformamide dimethyl acetal.

Compounds of Formula A may be obtained by means of standard urea preparation conditions from Compounds of Formula 34, wherein $R_3$ and $R_4$ are as defined for Formula (I) or (IA), such as reaction with 1,1'-carbonyldiimidazole in the presence of a suitable base such as DIPEA using DCM as solvent, followed by reaction of the corresponding $R_1$, using a suitable solvent, such as DCM for example at RT. Preferably, a compound of formula $R_1$—C(O)Cl is added to a cooled solution of the Compound of Formula 34 and DMAP in pyridine/DCM, and the reaction mixture is then heated to 50° C. overnight.

Scheme 2

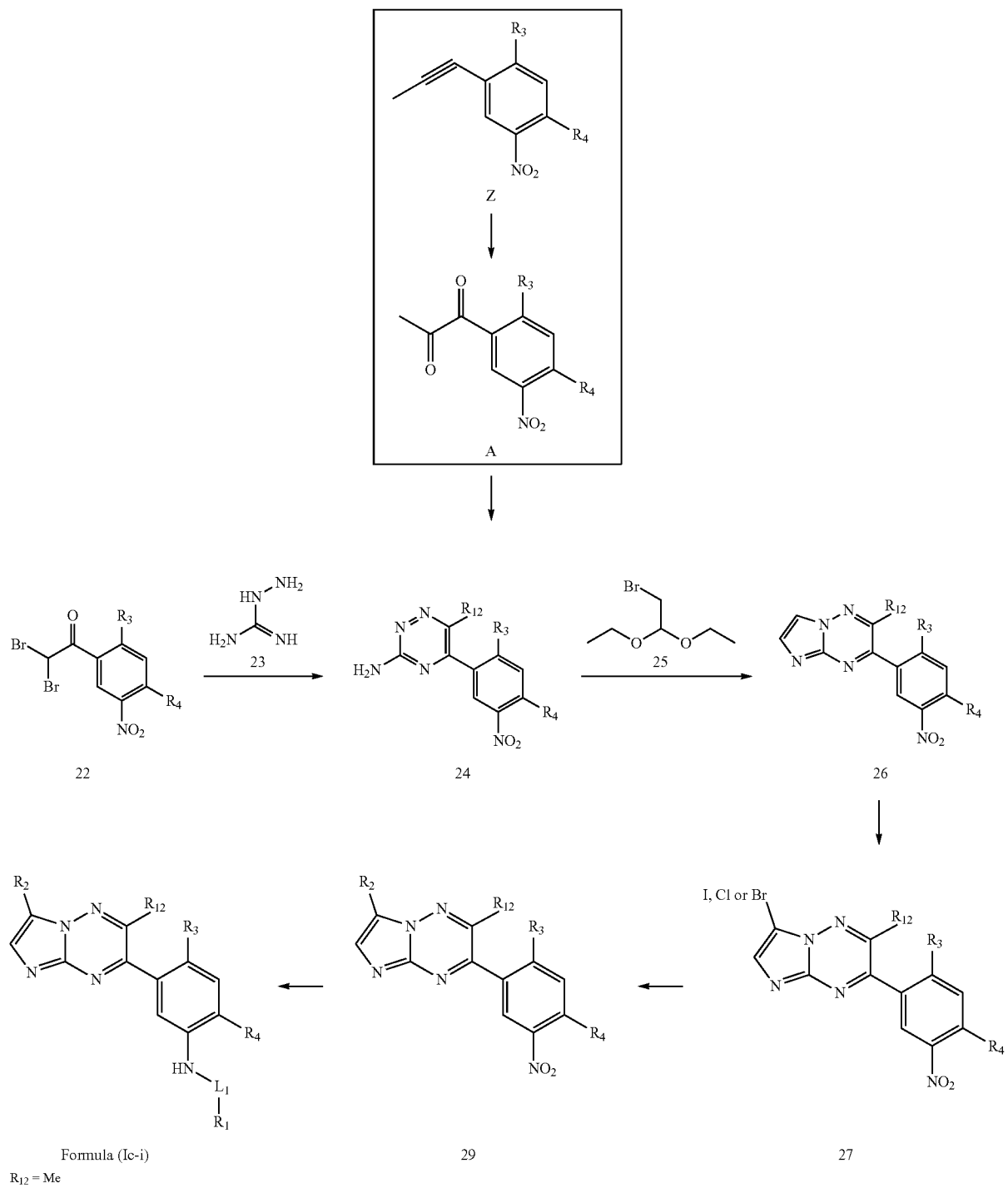

Compounds of Formula (Ic-i), which are compounds of Formula (I) or (IA) wherein $A_1$ is CH, $A_2$ is N, $R_2$ is Ar as defined for Formula (I) or (IA), $R_3$ and $R_4$ are independently selected from hydrogen, methyl, methoxy and cyano, $R_{12}$ is selected from hydrogen and methyl, and $R_{13}$ is as defined for Formula (I) or (IA), may be prepared according to the procedure in Scheme 2.

Compounds of Formula (Ic-i) may be obtained by reduction of the nitro group to an amine group of Compounds of Formula 29, wherein $R_3$ and $R_4$ are independently selected from hydrogen, methyl, methoxy and cyano and $R_{12}$ is selected from hydrogen and methyl, and Ar is as defined for Formula (I) or (IA), using a suitable reducing agent, followed by reaction with suitable reagents so as to introduce an $L_1$-$R_1$ group, wherein $L_1$ and $R_1$ are as defined for Formula (I) or (IA). For example, Compounds of Formula 29 may be reacted with iron in ammonium chloride in a suitable solvent such as water, under elevated temperature. This may be followed by reaction with $R_1(L_1)Cl$, wherein $L_1$ and $R_1$ are as defined for Formula (I) or (IA), in the presence of a suitable base, in a suitable solvent, such as DCM: pyridine, wherein pyridine is both a co-solvent and a base, or using a base such as $Et_3N$ in a suitable solvent, such as 1,2-dichloroethane.

For example, when $R_1(L_1)Cl$ is $R_1C(O)Cl$, wherein $R_1$ is as defined for Formula (I) or (IA), the reaction may be carried out in a suitable base such as dimethylaminepyrimidine in pyridine, in a suitable solvent such as DCM, at elevated temperature, or alternatively compounds may be reacted with triphosgene in a suitable solvent such as 1,2-dichloroethane, followed by reaction with $R_1$—H, for example pyrrolidine, in the presence of a suitable base such as $Et_3N$.

$R_1(L_1)Cl$ may either be commercially available or can be made using standard procedures, for example from $R_1C(O)OH$, which in turn is either commercially available or can be made using standard procedures.

Compounds of Formula 29 may be obtained from a coupling reaction between Compounds of Formula 27, wherein $R_3$ and $R_4$ are independently selected from hydrogen, methyl, methoxy and cyano and $R_{12}$ is selected from hydrogen and methyl, and compounds $R_2$—Y.

Compounds of Formula 29, wherein $R_2$ is Ar, $C_4$-$C_7$heterocycloalkyl, $C_5$-$C_7$heterocycloalkenyl, $NR_{5a}R_{5b}$ or X, may be obtained by reaction of Compounds of Formula 27, with $R_2$—Y, wherein $R_2$ is Ar, $C_4$-$C_7$heterocycloalkyl, $C_5$-$C_7$heterocycloalkenyl $NR_{5a}R_{5b}$ or X, and Y is hydrogen or a boronic acid or ester, for example tetrafluoroborate.

For example, when $R_2$—Y is Ar-boronic ester, the reaction may take place in the presence of a suitable catalyst, for example a palladium catalyst such as tetrakis (triphenylphosphine)palladium with a suitable base, such as sodium carbonate in a suitable solvent, such as DMF and water, under elevated temperature.

For example, when $R_2$—Y is morpholine, pyrrolidine or piperidine (Y is hydrogen), reaction may be carried out by means of sonication or under microwaves.

For example, when $R_2$—Y is $HNR_{5a}R_{5b}$, the reaction may be carried out using a coupling reaction in the presence of a palladium agent such as tris(dibenzylideneacetone)-dipalladium(0) and a suitable base, such as lithium bis(trimethylsilyl)amide and a suitable ligand, for example palladium(ii) phenethylamine chloride.

For example, when $R_2$—Y is X—H, reaction with Compounds of Formula 27 may be carried out by means of a coupling reaction, in the presence of a suitable palladium agent, such as palladium acetate.

Compounds of Formula 27 may be obtained from Compounds of Formula 26, wherein $R_3$ and $R_4$ are independently selected from hydrogen, methyl, methoxy and cyano and $R_{12}$ is selected from hydrogen and methyl, by treating Compounds of Formula 26 with a suitable brominating reagent such as bromine in acetic acid, in the presence of a catalyst such as sodium acetate, or similarly treating with a suitable chlorinating agent, or iodinating agent, as desired.

Compounds of Formula 26 may be prepared from Compounds of Formula 24, wherein $R_3$ and $R_4$ are independently selected from hydrogen, methyl, methoxy and cyano and $R_{12}$ is selected from hydrogen and methyl. Compounds of Formula 24 may be reacted with 2-bromo-1,1-diethoxyethane (Compound 25) in the presence of a suitable acid such as HBr, in a suitable solvent such as ethanol, under elevated temperature.

Compounds of Formula 24, wherein $R_{12}$ is hydrogen, may be obtained by a reaction between Compounds of Formula 22, wherein $R_3$ and $R_4$ are independently selected from hydrogen, methyl, methoxy and cyano, and Compound 23.

Compounds of Formula 22 may be commercially available or synthesised according to standard procedures. For example, Compounds of Formula 22, wherein $R_3$ or $R_4$ are selected from bromo, methyl, methoxy and cyano may be prepared from Compounds of Formula 22a, by a dibromination reaction according to K., Shoji et al. *Bull. Chem. Soc. Japan*, 1987, 60(7), 2667.

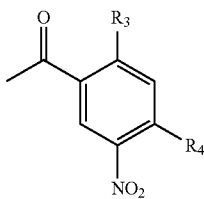

Compounds of Formula 24, wherein $R_{12}$ is methyl, may be prepared from Compounds of Formula A, wherein $R_3$ and $R_4$ are independently selected from hydrogen, methyl, methoxy and cyano. Compound 23 may be reacted with Compounds of Formula A in a suitable solvent, for example EtOH and water, for example as described by Jonge, I. de et al., Australian Journal of Chemistry, 1987, 40 (12), 1979-1988.

Compounds of Formula A may be prepared from Compounds of Formula Z, wherein $R_3$ and $R_4$ are independently selected from hydrogen, methyl, methoxy and cyano, for example by treating Compounds of Formula Z with sodium periodate, in the presence of a catalyst such as $C_{31}H_{29}Br_2N_3Ru*CH_2Cl_2$, in a suitable solvent such as and water and acetonitrile, for example as described in Bera, J. K. et al, Journal of the American Chemical Society, 2014, 136 (40), 13987-13990.

Compounds of Formula Z may be commercially available or prepared using standard procedures.

Scheme 3

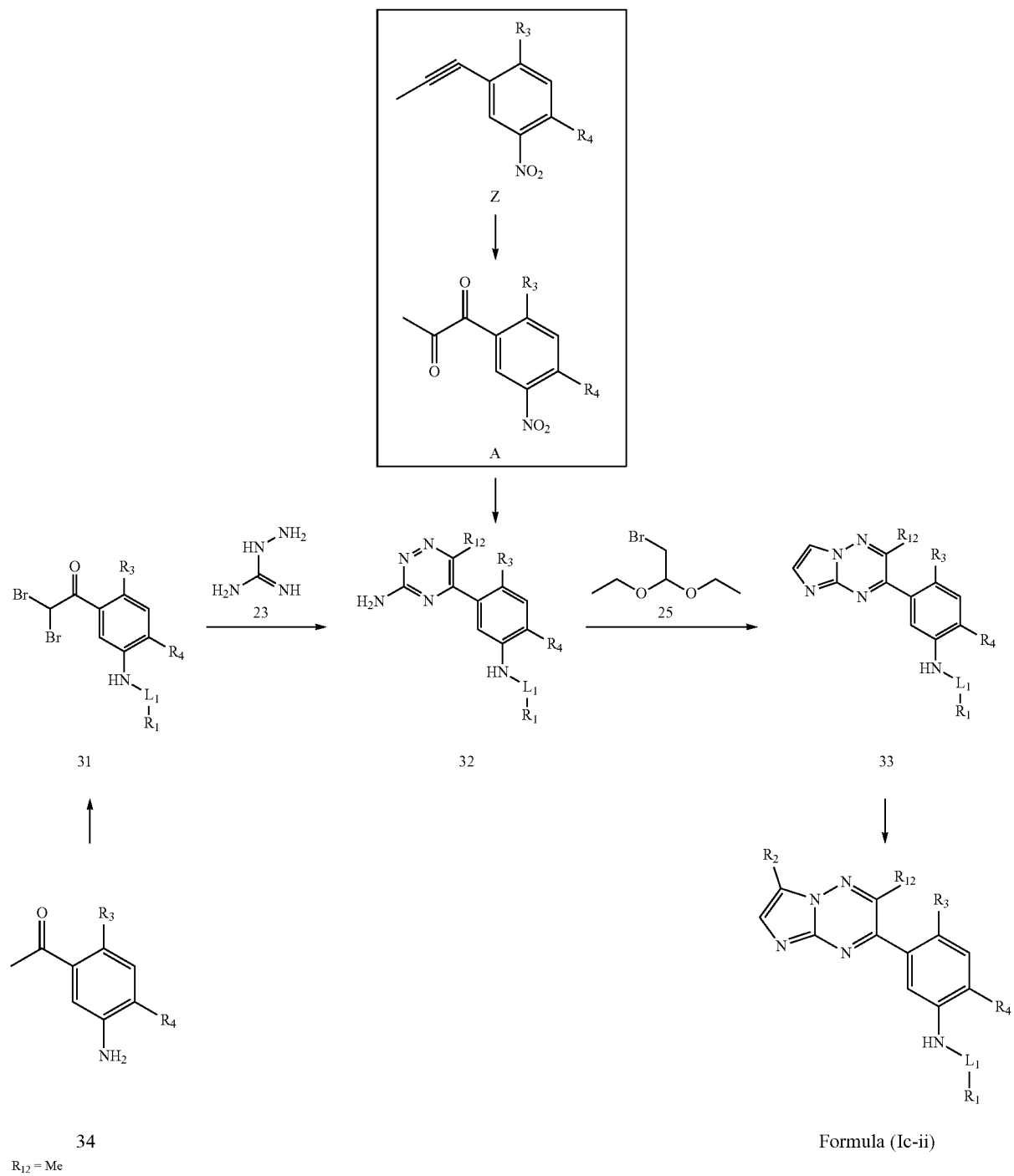

$R_{12}$ = Me

Compounds of Formula (Ic-ii), which are compounds of Formula (I) or (IA) wherein $A_1$ is CH, $A_2$ is N, and $R_2$, $R_3$, $R_4$ $R_{12}$ and $R_{13}$ are as defined for Formula (I) or (IA), may be prepared according to the procedure in Scheme 3.

It will be readily apparent to the skilled artisan that Scheme 3 depicts essentially the same synthetic steps to those in Scheme 2, in a different order, and that therefore similar reaction conditions may be used for each of the equivalent synthetic steps of Scheme 3 as outlined for Scheme 2.

Compounds of Formula 32, wherein $R_{12}$ is halo, may be prepared by a halogenation reaction of Compounds of Formula 32, wherein $R_{12}$ is hydrogen. For example, to prepare Compounds of Formula 32, wherein $R_{12}$ is Br, a bromination reaction may be carried out using a brominating agent, such as N-bromosuccinamide, in a suitable solvent, such as DMF.

Examples of protecting groups that may be employed in the synthetic routes described herein and the means for their removal can be found in T. W. Greene '*Protective Groups in*

*Organic Synthesis'*, 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively.

Conventional methods of isolation, for example extraction from or into aqueous or non-aqueous solvents may be used. Conventional methods of drying organic solvents, solutions, or extracts, such as shaking with anhydrous magnesium sulphate, or anhydrous sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times temperatures may typically be determined by reaction-monitoring techniques, for example thin-layer chromatography and LC-MS.

Individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

Methods of Use

It will be appreciated by those skilled in the art that references herein to treatment refer to the treatment of established conditions. However, the compounds of Formula (I) or (IA) and pharmaceutically acceptable salts thereof may, depending on the condition, also be useful in the prevention (prophlyaxis) of certain diseases. Thus, in one embodiment, there is provided the treatment or prevention of a disease. In another embodiment, there is provided the treatment of a disease. In a further embodiment, there is provided the prevention of a disease.

There is thus provided as a further aspect of the invention a compound of Formula (I) or (IA), or a pharmaceutically acceptable salt thereof, for use in therapy.

It will be appreciated that, when a compound of Formula (I) or (IA) or a pharmaceutically acceptable salt thereof is used in therapy, it is used as an active therapeutic agent.

There is also therefore provided a compound of Formula (I) or (IA), or a pharmaceutically acceptable salt thereof, for use in the treatment or prevention of a parasitic disease, for example Chagas disease, Human African Trypanosomiasis, Animal African trypanosomiasis or leishmaniasis, particularly visceral leishmaniasis. There is further provided a compound of Formula (I) or (IA), or a pharmaceutically acceptable salt thereof, for use in the treatment or prevention of Chagas disease. There is also provided a compound of Formula (I) or (IA) or a pharmaceutically acceptable salt thereof, for use in the treatment of leishmaniasis. There is also provided a compound of Formula (I) or (IA), or a pharmaceutically acceptable salt thereof, for use in the treatment or prevention of visceral leishmaniasis. There is also provided a compound of Formula (I) or (IA), or a pharmaceutically acceptable salt thereof, for use in the treatment or prevention of Human African Trypanosomiasis.

There is further provided the use of a compound of Formula (I) or (IA), or a pharmaceutically acceptable salt thereof, in the manufacture of a medicament for the treatment or prevention of a parasitic disease, for example Chagas disease, Human African Trypanosomiasis, Animal African trypanosomiasis or leishmaniasis, particularly visceral leishmaniasis. There is also provided the use of a compound of Formula (I) or (IA), or a pharmaceutically acceptable salt thereof, in the manufacture of a medicament for the treatment or prevention of leishmaniasis. There is further provided the use of a compound of Formula (I) or (IA), or a pharmaceutically acceptable salt thereof, in the manufacture of a medicament for the treatment or prevention of visceral leishmaniasis. There is also provided the use of a compound of Formula (I) or (IA), or a pharmaceutically acceptable salt thereof, in the manufacture of a medicament for the treatment or prevention of Chagas disease. There is further provided the use of a compound of Formula (I) or (IA), or a pharmaceutically acceptable salt thereof, in the manufacture of a medicament for the treatment or prevention of Human African Trypanosomiasis.

There is further provided a method of treatment or prevention of a parasitic disease, for example Chagas disease, Human African Trypanosomiasis, Animal African trypanosomiasis or leishmaniasis, particularly visceral leishmaniasis, which method comprises administering to a human subject in need thereof, a therapeutically effective amount of a compound of Formula (I) or (IA), or a pharmaceutically acceptable salt thereof. There is also provided a method of treatment or prevention of leishmaniasis, which method comprises administering to a human subject in need thereof, a therapeutically effective amount of a compound of Formula (I) or (IA), or a pharmaceutically acceptable salt thereof. There is further provided a method of treatment or prevention of visceral leishmaniasis, which method comprises administering to a human subject in need thereof, a therapeutically effective amount of a compound of Formula (I) or (IA), or a pharmaceutically acceptable salt thereof. There is also provided a method of treatment or prevention of Chagas disease, which method comprises administering to a human subject in need thereof, a therapeutically effective amount of a compound of Formula (I) or (IA), or a pharmaceutically acceptable salt thereof. There is further provided a method of treatment or prevention of a Human African Trypanosomiasis, which method comprises administering to a human subject in need thereof, a therapeutically effective amount of a compound of Formula (I) or (IA), or a pharmaceutically acceptable salt thereof.

There is also therefore provided N-(4-fluoro-3-(3-morpholinoimidazo[1,2-a]pyrimidin-7-yl)phenyl)pyrrolidine-1-carboxamide, or a pharmaceutically acceptable salt thereof, for use in the treatment or prevention of a parasitic disease, for example Chagas disease, Human African Trypanosomiasis, Animal African trypanosomiasis or leishmaniasis, particularly visceral leishmaniasis. There is further provided N-(4-fluoro-3-(3-morpholinoimidazo[1,2-a]pyrimidin-7-yl)phenyl)pyrrolidine-1-carboxamide, or a pharmaceutically acceptable salt thereof, for use in the treatment or prevention of Chagas disease. There is further provided N-(4-fluoro-3-(3-morpholinoimidazo[1,2-a]pyrimidin-7-yl)phenyl)pyrrolidine-1-carboxamide, or a pharmaceutically acceptable salt thereof, for use in the treatment or prevention of Human African Trypanosomiasis. There is further provided N-(4-fluoro-3-(3-morpholinoimidazo[1,2-a]pyrimidin-7-yl)phenyl)pyrrolidine-1-carboxamide, or a pharmaceutically acceptable salt thereof, for use in the treatment or prevention of leishmaniasis. There is further provided N-(4-fluoro-3-(3-morpholinoimidazo[1,2-a]pyrimidin-7-yl)phenyl)pyrrolidine-1-carboxamide, or a pharmaceutically acceptable salt thereof, for use in the treatment or prevention of visceral leishmaniasis.

There is further provided the use of N-(4-fluoro-3-(3-morpholinoimidazo[1,2-a]pyrimidin-7-yl)phenyl)pyrrolidine-1-carboxamide, or a pharmaceutically acceptable salt thereof, in the manufacture of a medicament for the treatment or prevention of a parasitic disease, for example Chagas disease, Human African Trypanosomiasis, Animal African trypanosomiasis or leishmaniasis, particularly visceral leishmaniasis. There is further provided the use of N-(4-fluoro-3-(3-morpholinoimidazo[1,2-a]pyrimidin-7-yl)phenyl)pyrrolidine-1-carboxamide, or a pharmaceutically acceptable salt thereof, in the manufacture of a medicament for the treatment or prevention of Chagas disease. There is further provided the use of N-(4-fluoro-3-(3-morpholinoimidazo[1,2-a]pyrimidin-7-yl)phenyl)pyrrolidine-1-carboxamide, or a pharmaceutically acceptable salt thereof, in the manufacture of a medicament for the treatment or prevention of Human African Trypanosomiasis. There is further provided the use of N-(4-fluoro-3-(3-morpholinoimidazo[1,2-a]pyrimidin-7-yl)phenyl)pyrrolidine-1-carboxamide, or a pharmaceutically acceptable salt thereof, in the manufacture of a medicament for the treatment or prevention of leishmaniasis. There is further provided the use of N-(4-fluoro-3-(3-morpholinoimidazo[1,2-a]pyrimidin-7-yl)phenyl)pyrrolidine-1-carboxamide, or a pharmaceutically acceptable salt thereof, in the manufacture of a medicament for the treatment or prevention of visceral leishmaniasis.

There is further provided a method of treatment or prevention of a parasitic disease, for example Chagas disease, Human African Trypanosomiasis, Animal African trypanosomiasis or leishmaniasis, particularly visceral leishmaniasis, which method comprises administering to a human subject in need thereof, a therapeutically effective amount of N-(4-fluoro-3-(3-morpholinoimidazo[1,2-a]pyrimidin-7-yl)phenyl)pyrrolidine-1-carboxamide, or a pharmaceutically acceptable salt thereof. There is further provided a method of treatment or prevention of Chagas disease, which method comprises administering to a human subject in need thereof, a therapeutically effective amount of N-(4-fluoro-3-(3-morpholinoimidazo[1,2-a]pyrimidin-7-yl)phenyl)pyrrolidine-1-carboxamide, or a pharmaceutically acceptable salt thereof. There is further provided a method of treatment or prevention of Human African Trypanosomiasis which method comprises administering to a human subject in need thereof, a therapeutically effective amount of N-(4-fluoro-3-(3-morpholinoimidazo[1,2-a]pyrimidin-7-yl)phenyl)pyrrolidine-1-carboxamide, or a pharmaceutically acceptable salt thereof. There is further provided a method of treatment or prevention of leishmaniasis, which method comprises administering to a human subject in need thereof, a therapeutically effective amount of N-(4-fluoro-3-(3-morpholinoimidazo[1,2-a]pyrimidin-7-yl)phenyl)pyrrolidine-1-carboxamide, or a pharmaceutically acceptable salt thereof. There is further provided a method of treatment or prevention of visceral leishmaniasis, which method comprises administering to a human subject in need thereof, a therapeutically effective amount of N-(4-fluoro-3-(3-morpholinoimidazo[1,2-a]pyrimidin-7-yl)phenyl)pyrrolidine-1-carboxamide, or a pharmaceutically acceptable salt thereof.

Compositions and Formulations

While it is possible that, for use in the methods of the invention, a compound of Formula (I) or (IA) or a pharmaceutically acceptable salt thereof may be administered as the bulk substance, it is usually preferable to present the active ingredient in a pharmaceutical formulation, for example, wherein the agent is in admixture with at least one pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise, in addition to the carrier, any suitable binder(s), lubricant(s), suspending agent(s), coating agent(s), and/or solubilizing agent(s).

The phrase "pharmaceutically acceptable", as used herein, refers to salts, molecular entities and other ingredients of compositions that are generally physiologically tolerable and do not typically produce untoward reactions when administered to a mammal (e.g., human).

Suitably, as used herein, the term "pharmaceutically acceptable" means approved by a regulatory agency of the Federal or a state government for use in mammals, and more particularly in humans, or listed in the U.S. Pharmacopoeia or other generally recognized texts, for example the International Union of Pure and Applied Chemistry (IUPAC) Handbook of Pharmaceutical Salts, 2011 Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine, by analogy with formulation of anti-bacterials, such as anti-tubercular agents, or formulation of antimalarial agents.

The compounds of the invention will normally, but not necessarily, be formulated into pharmaceutical compositions prior to administration to a patient. In one aspect, the invention is directed to a pharmaceutical composition comprising a compound of Formula (I) or (IA), or a pharmaceutically acceptable salt thereof. In another aspect the invention is directed to a pharmaceutical composition comprising a compound of Formula (I) or (IA), or a pharmaceutically acceptable salt thereof, together with at least one pharmaceutically acceptable carrier. The carrier must be "acceptable" in the sense of being compatible with the other ingredients of the formulation and not deleterious to the recipient thereof.

A therapeutically effective amount of the compound of the present invention can be determined by methods known in the art. The therapeutically effective quantities will depend on the age and on the general physiological condition of the subject, the route of administration and the pharmaceutical formulation used. The therapeutic doses will generally be between about 1 and 2000 mg/day, for example between about 500 and 2000 mg/day. The daily dose as employed for human treatment will range from 1 to 2000 mg, which may be administered in one or two daily doses, for example, depending on the route of administration and the condition of the subject. When the composition comprises dosage units, each unit will contain 1 mg to 2 g of active ingredient. When the dosage form is a tablet, the total weight of the tablet is suitably 1000 mg or lower.

In general, a suitable dose for an animal will be in the range of from about 0.01 to about 50 15 mg/kg of body weight per day, The compound is conveniently administered in unit dosage form; for example containing 0.01 to 50 mg/kg of active ingredient. These dosages are based on an average cow having a weight of about 20 kg to 1500 kg, and more particularly 600 kg to 800 kg.

The present invention is further related to a pharmaceutical composition comprising a compound of Formula (I) or (IA), or a pharmaceutically acceptable salt thereof.

The present invention is further related to a pharmaceutical composition for the treatment of a parasitic disease, for example Chagas disease, Human African Trypanosomiasis, Animal African trypanosomiasis or leishmaniasis, particularly visceral leishmaniasis, comprising a compound of Formula (I) or (IA) or a pharmaceutically acceptable salt thereof.

The present invention is yet further related to a pharmaceutical composition comprising a compound of Formula (I) or (IA), or a pharmaceutically acceptable salt thereof together with at least one pharmaceutically acceptable carrier.

The present invention is even further related to a pharmaceutical composition comprising a) a compound of Formula (I) or (IA) or a pharmaceutically acceptable salt thereof, and b) a pharmaceutically acceptable carrier.

In one embodiment, there is provided a pharmaceutical composition comprising a) N-(4-fluoro-3-(3-morpholinoimidazo[1,2-a]pyrimidin-7-yl)phenyl)pyrrolidine-1-carboxamide or a pharmaceutical acceptable salt thereof, and b) a pharmaceutically acceptable carrier.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more (at least one) pharmaceutically acceptable carriers or excipients. In one aspect, the pharmaceutical composition is formulated for oral administration.

The pharmaceutical compositions of the invention include those in a form adapted for oral use in mammals including humans.

The pharmaceutical compositions of the invention include those in a form adapted for oral use and may be used for the treatment of a parasitic disease, for example Chagas disease, Human African Trypanosomiasis, Animal African trypanosomiasis or leishmaniasis, particularly visceral leishmaniasis, in mammals including humans.

The compound of the invention can be administered for immediate-, delayed-, modified-, sustained-, pulsed- or controlled-release applications.

The composition may be formulated for administration by any convenient route. For the treatment of a parasitic disease, for example Chagas disease, Human African Trypanosomiasis, Animal African trypanosomiasis or leishmaniasis, particularly visceral leishmaniasis, the compositions may be in the form of tablets, capsules, powders, granules, lozenges, aerosols or liquid preparations, for oral use.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

A compound of Formula (I) or (IA), or a pharmaceutically acceptable salt thereof, may be the sole therapeutic agent in the compositions of the invention, or it may be present in the formulation in combination with one or more (at least one) additional therapeutic agents.

The invention thus provides in a further aspect, a combination comprising (a) a compound of Formula (I) or (IA), or a pharmaceutically acceptable salt thereof, and (b) at least one additional therapeutic agent. The combination optionally further comprises at least one pharmaceutically acceptable carrier. In one aspect of the invention there is provided a pharmaceutical composition comprising a compound of Formula (I) or (IA), or a pharmaceutically acceptable salt thereof, together with at least one pharmaceutically acceptable carrier and one or more (at least one) additional therapeutic agents.

Examples of such one or more (at least one) additional therapeutic agents are anti-*leishmania* agents, including, but not limited to, miltefosine, paromomycin, sodium stibugluconate, meglumine antimoniate, amphotericin B deoxycholate or liposomal amphotericin B. In one aspect of the invention for oral treatment the additional therapeutic agent is miltefosine. Such chemotherapy is determined by the judgment of the treating physician using preferred drug combinations. In addition to the aforementioned, future anti-*leishmania* therapeutic agents emerging from clinical studies may also be employed as the one or more (at least one) additional therapeutic agents in a combination with a compound of Formula (I) or (IA).

In another aspect, the invention provides a combination comprising a compound of Formula (I) or (IA) or a pharmaceutically acceptable salt thereof, together with one or more (at least one) additional therapeutic agents, such as an anti-parasitic agent, an anti-AIDS or anti-HIV agent, or an anti-TB agent.

In a further aspect, the one or more (at least one) additional therapeutic agent is, for example, an agent useful for the treatment of a parasitic disease in a mammal, a therapeutic vaccine, an anti-TB agent or an agent for the treatment of HIV/AIDS.

The compounds of Formula (I) or (IA), or a pharmaceutically acceptable salt thereof, and further therapeutic agent(s) may be employed in combination by administration simultaneously in a unitary pharmaceutical composition including both agents. Alternatively, the combination may be administered separately in separate pharmaceutical compositions, each including one of the agents in a sequential manner wherein, for example, a compound of Formula (I) or (IA) or a pharmaceutically acceptable salt thereof is administered first and the other agent second and vice versa. Such sequential administration may be close in time (e.g. simultaneously) or remote in time. For example, administration of the other agent several minutes to several dozen minutes after the administration of the first agent, and administration of the other agent several hours to several days after the administration of the first agent are within the scope of the invention, wherein the lapse of time is not limited. For example, one agent may be administered once a day, and the other agent may be administered 2 or 3 times a day, or one agent may be administered once a week, and the other agent may be administered once a day.

When administration is sequential, either the compound of the present invention or one or more (at least one) additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

During a treatment regime, it will be appreciated that administration of each agent of the combination may be repeated one or more (at least one) times.

Furthermore, the agents may be administered in the same or different dosage forms, e.g. one agent may be administered topically and the other compound may be administered orally. Suitably, both agents are administered orally.

The combinations may be presented as a combination kit. By the term "combination kit" "or kit of parts" as used herein is meant the pharmaceutical composition or compositions that are used to administer the combination according to the invention. When the agents of the combination are administered simultaneously, the combination kit can contain the agents in a single pharmaceutical composition, such as a tablet, or in separate pharmaceutical compositions. When the agents are not administered simultaneously, the combination kit will contain each agent in separate pharmaceutical compositions either in a single package or in separate pharmaceutical compositions in separate packages. The combination kit can also be provided with instructions, such as dosage and administration instructions. Such dosage and administration instructions can be of the kind that are provided to a doctor, for example by a drug product label, or they can be of the kind that are provided by a doctor, such as instructions to a patient.

In one aspect, the one or more (at least one) additional therapeutic agent is a therapeutic vaccine. A compound of Formula (I) or (IA), or a pharmaceutically acceptable salt thereof, may thus be administered in conjunction with vaccination against parasitic infection. Existing veterinary vaccines for leishmaniasis include CaniLeish and Leishmune.

A compound of Formula (I) or (IA), or a pharmaceutically acceptable salt thereof, may be either i) administered to an individual who has previously been vaccinated against parasitic infection; ii) administered to an individual who is subsequently vaccinated against parasitic infection; or iii) may be co-administered with a vaccine against parasitic infection, either by administering the compound of the invention and the vaccine together in the same dosage form or co-administering the compound of the invention and the vaccine in separate dosage forms.

When a compound of Formula (I) or (IA), or a pharmaceutically acceptable salt thereof is used in combination with one or more (at least one) additional therapeutic agents, the dose of the compound or agent may differ from that when the compound or agent is used alone. Appropriate doses will be readily appreciated by those skilled in the art. It will be appreciated that the amount of a compound of the invention and the one or more (at least one) additional therapeutic agents required for use in treatment will vary with the nature of the condition being treated and the age and the condition of the patient and will be ultimately at the discretion of the attendant physician or veterinarian.

Abbreviations

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

AcOEt Ethyl acetate
AIDS Acquired Immune Deficiency Syndrome
approx. approximately
Bt 1, 2, 3-Benzotriazole
$CDCl_3$ Deuterated chloroform
CLND ChemiLuminescent Nitrogen Detection
$CO_2$ Carbon dioxide
Cy Cyclohexanes
DAPI 4',6-Diamidino-2-phenylindole
DAST Diethylaminosulfur trifluoride
DCE 1,2-dichloroethane
DCM Dichloromethane
DIPEA Diisopropylethylamine
DMAP 4-Dimethylaminopyridine
DME 1,2-Dimethoxyethane
DMEM Dulbecco's Modified Eagle Medium
DMF N,N-Dimethylformamide
DMSO Dimethylsulfoxide
DMSO-$d_6$ Deuterated dimethylsulfoxide
$Et_2O$ Diethyl ether
EtOAc Ethyl acetate
EtOH Ethanol
FBS fetal bovine serum
g grams
GFP Green Fluorescent Protein
h hours
$H_2O$ Water
HCl hydrochloric acid
HEPES 2-[4-(2-hydroxyethyl)piperazin-1-yl]ethanesulfonic acid
HIV Human Immunodeficiency Virus
HPLC high performance liquid chromatography
Hz hertz
KOH potassium
L liters
LCMS liquid chromatography/mass spectrometry
M Molar
MeCN acetonitrile MEM 2-methoxyethoxy methyl
MeOH Methanol
min Minutes
mL Milliliter
mmol Millimole
nM Millimolar
μM Micromolar
MS Mass spectrum
N Normal concentration
NaOH Sodium hydroxide
NMR Nuclear Magnetic Resonance spectroscopy
PBS Phosphate buffered saline
PBS-A Bovine serum albumin
Pd(dppf)C$_2$.DCM [1,1'-Bis(diphenylphosphino)ferrocene]dichloropalladium(II), complex with dichloromethane
PMA Phorbol 12-myristate 13-acetate
RB Round-bottomed
RPMI Roswell Park Memorial Institute
rt/RT room temperature
SM starting material
SNAP Biotage® Flash chromatography cartridges
THF Tetrahydrofuran
THP Tetrahydropyranyl
THP-1 human acute monocytic leukemia cell line
TLC Thin layer chromatography
UPLC Ultra-Performance Liquid Chromatography
XPhos 2-Dicyclohexylphosphino-2',4',6'-triisopropylbiphenyl
Xantphos 4,5-Bis(diphenylphosphino)-9,9-dimethylxanthene

EXAMPLES

The following Examples illustrate the invention, as guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (ppm) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Reactions involving metal hydrides (including sodium hydride) and organo-metallic reagents are carried out under argon or nitrogen unless otherwise specified.

In the following Intermediates and Examples, where the relative stereochemistry of the compound has been identified, this is indicated both in the name and structure of the compound.

In certain of the following Intermediates and Examples, starting materials are identified by reference to other Intermediate or Example numbers. This does not signify that the actual material (or "batch") obtained from any particular Intermediate or Example was necessarily used in a subsequent step exemplified herein, but is used as a short-hand means of denoting the relevant compound name.

The names of the intermediates and examples have been obtained using the compound naming program within "ChemBioDraw Ultra v12" or "ACD Name Pro 6.02".

INTERMEDIATES

Intermediate 1: 1,2-bis(1H-benzo[d][1,2,3]triazol-1-yl)-1,2-dimorpholinoethane

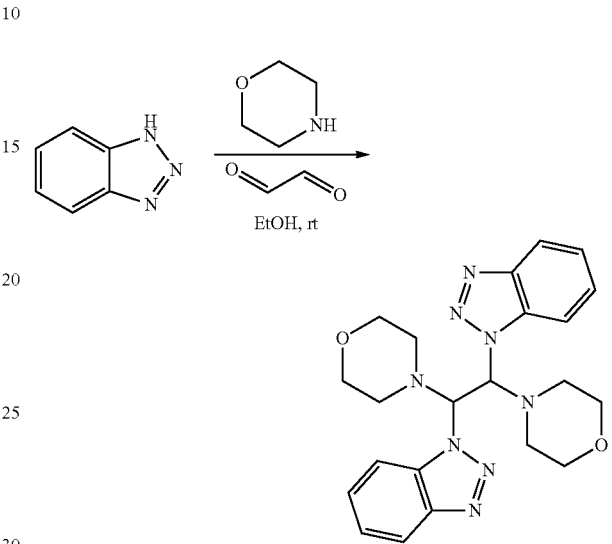

Benzotriazole (3.5 g, 29.4 mmol) and morpholine (2.57 ml, 29.4 mmol) were stirred in ethanol (50 mL) at 20 C for 5 min. Glyoxal (2.13 g, 14.7 mmol) was added to the reaction mixture and the stirring was continued overnight at the same temperature. The solid was filtered and washed with ethanol to obtain 4.13 g of desired product (65% yield) $^1$H NMR (400 MHz, DMSO-d$_6$): δ 8.43 (1H, d), 8.14 (2H, m), 7.64 (1H, m), 7.48 (2H, m), 7.25 (2H, m), 6.99 (1H, s, b), 3.66 (3H, m), 3.32 (1H, s, b), 3.11 (2H, s), 2.85 (5H, m), 2.56 (4H, s, b).

Intermediate 2: 2-bromo-2-phenylacetaldehyde

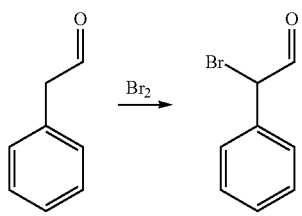

To a solution of phenylacetaldehyde (1 g, 8.3 mmol) in DCM (3 mL) was added dropwise a solution of bromine (1.3 g, 8.3 mmol) in DCM (3 mL) at −10 C over 30 minutes. The resulting solution was allowed to warm up to rt and stirred at 50° C. overnight. Aq. NaHCO$_3$ solution was added to the cooled mixture and the solution was extracted with DCM. The organic layer was dried (Na$_2$SO$_4$), filtered and evaporated under reduced pressure to afford crude product (1.8 g) as a green liquid.
$^1$H NMR (400 MHz, CDCl$_3$): δ 9.59 (1H, d), 7.44 (5H, m), 5.28 (1H, d).

Intermediate 4: 4-(3-nitrophenyl)pyrimidin-2-amine

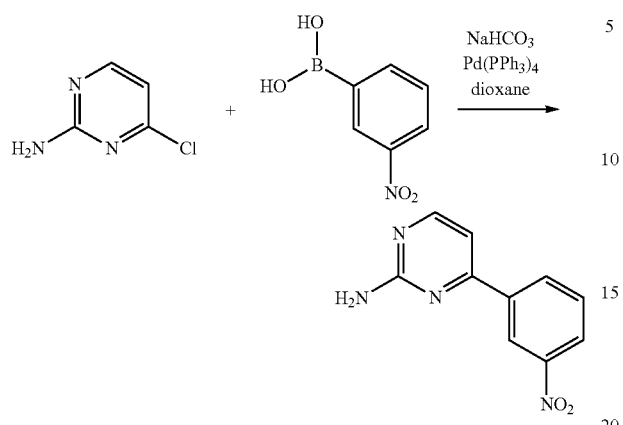

A stirred solution of 2-amino-4-chloropyrimidine (Intermediate 3, ALDRICH, 1.0 g, 7.75 mmol) and 3-nitrophenylboronic acid (ALDRICH, 1.2 g, 7.75 mmol) in 1,4-dioxane (50 mL) and saturated $NaHCO_3$ (12.5 mL) was degassed for 10 minutes with nitrogen. $Pd(PPh_3)_4$ (ALDRICH, 0.447 g, 0.38 mmol) was then added, and the reaction was heated at 95° C. overnight. The reaction was allowed to cool to room temperature and then poured onto water and EtOAc.

The organic layer was separated, dried ($Na_2SO_4$), filtered and evaporated under reduced pressure. Flash chromatography of the residue (SNAP 55 KP-NH, 100% DCM) afforded the title compound (1.5 g, 93% yield) as a yellow solid.

$^1H$ NMR (400 MHz, DMSO-$d_6$): δ 8.92 (1H, m), 8.51 (1H, dt), 8.41 (1H, d), 8.36 (1H, ddd), 7.81 (1H, t), 7.29 (1H, d), 6.87 (2H, s, b).

m/z=217 (M+H)

Intermediate 5: 4-(2-fluoro-5-nitrophenyl)pyrimidin-2-amine

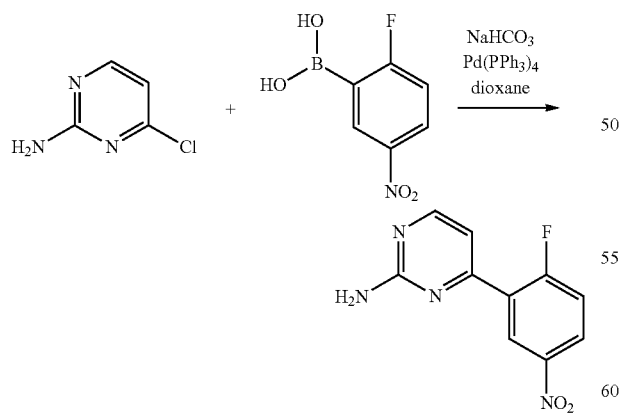

A stirred solution of 2-amino-4-chloropyrimidine (ALDRICH, 2.0 g, 15.43 mmol) and 2-fluoro-5-nitrophenyl) boronic acid (ALFA AESAR, 2.8 g, 15.43 mmol) in 1,4-Dioxane (100 mL) and saturated $NaHCO_3$ (25 mL) was degassed for 10 minutes with nitrogen. $Pd(PPh_3)_4$ (ALDRICH, 0.891 g, 0.77 mmol) was then added, and the reaction was heated at 95° C. overnight. The reaction was allowed to cool to room temperature and then poured onto water and EtOAc. The organic layer was separated, dried ($Na_2SO_4$), filtered and evaporated under reduced pressure. Flash chromatography of the residue (SNAP 55 KP-NH, 100% DCM) afforded the title compound (2.4 g, 66% yield) as a yellow solid.

m/z=235 (M+H)

Intermediate 6: 7-(2-fluoro-5-nitrophenyl)-3-phenylimidazo[1,2-a]pyrimidine

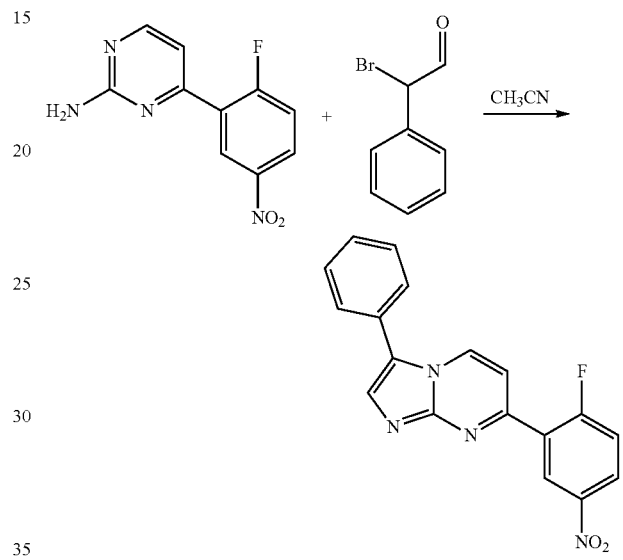

To a stirred solution of 4-(2-fluoro-5-nitrophenyl)pyrimidin-2-amine (Intermediate 5, 0.5 g, 2.3 mmol) in DCE (20 mL) was added 2-bromo-2-phenylacetaldehyde (Intermediate 2, 2.3 mmol). The resulting reaction mixture was stirred at reflux overnight. The mixture was evaporated under reduced pressure.

Chromatography of the residue (SNAP KP-Si 50 g, 100% DCM) afforded the title compound (0.4 g) with low purity degree (45% by UPLC). The impure product was chromatographed on NH-modified silica gel (SNAP 28 g, Cy/DCM, 95:5-0:100) to give the title compound as an orange solid (0.105 g, 13% yield).

$^1H$ NMR (400 MHz, DMSO-$d_6$): δ 9.20 (1H, d), 8.96 (1H, dd), 8.48 (1H, m), 8.16 (1H, s), 7.77 (3H, m), 7.61 (3H, m), 7.51 (1H, m).

m/z=335 (M+H)

Intermediate 7: 7-(3-nitrophenyl)-3-phenylimidazo[1,2-a]pyrimidine

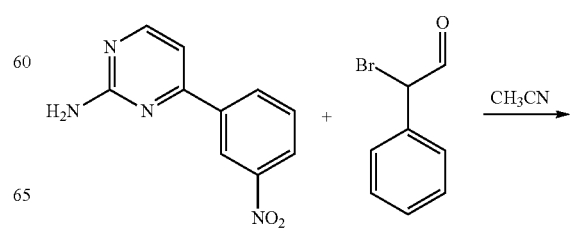

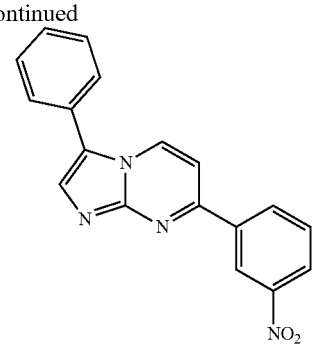

To a stirred suspension of 4-(3-nitrophenyl)pyrimidin-2-amine (Intermediate 4, 0.500 g, 2.31 mmol) in CH$_3$CN (20 mL) was added 2-bromo-2-phenylacetaldehyde (Intermediate 2, 2.31 mmol). The resulting reaction mixture was stirred at reflux for 3 h. UPLC check showed the reaction was at ~40% conversion. Further 2-bromo-2-phenylacetaldehyde (2.31 mmol) was added and the mixture was stirred at reflux overnight. UPLC check showed the reaction was at ~40% conversion. The mixture was evaporated under reduced pressure. The residue was chromatographed on NH-modified silica gel (SNAP 55 g) eluting with DCM to give the title compound as an orange solid (0.165 g, 22% yield).

$^1$H NMR (400 MHz, DMSO-d$_6$): δ 9.17 (1H, d), 9.06 (1H, m), 8.73 (1H, m), 8.41 (1H, m), 8.10 (1H, s), 7.90 (2H, m), 7.78 (2H, m), 7.61 (2H, m), 7.50 (1H, m).

m/z=317 (M+H)

Intermediate 8: 3-(3-phenylimidazo[1,2-a]pyrimidin-7-yl)aniline

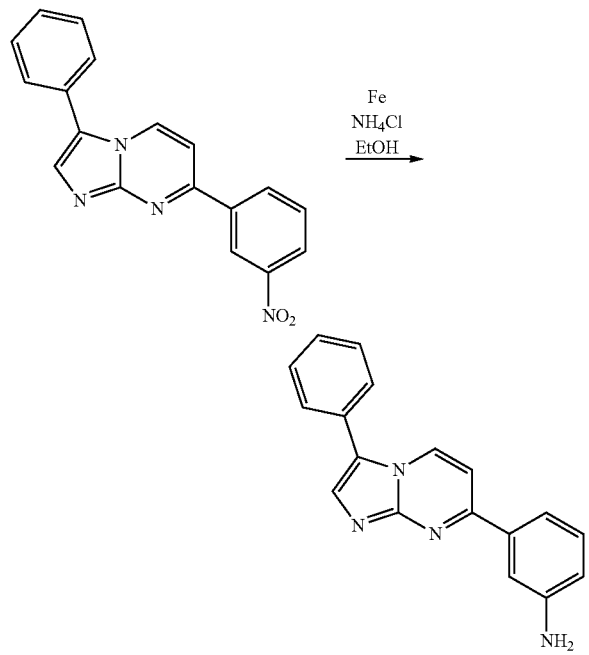

To a solution of 7-(3-nitrophenyl)-3-phenylimidazo[1,2-a]pyrimidine (Intermediate 7, 0.165 g, 0.52 mmol) in EtOH (3 mL), iron (ALDRICH, 0.232 g, 4.16 mmol) was added followed by a solution of ammonium chloride (0.111 g, 2.08 mmol) in water (1 mL). The reaction mixture was allowed to warm up to 75° C. and stirred at this temperature for 3 h. The reaction mixture was allowed to cool to rt and passed through a phase separator. Solvents were removed under reduced pressure to afford the desired compound as a yellow solid (0.13, 87% yield).

$^1$H NMR (400 MHz, DMSO-d$_6$): δ 9.03 (1H, d), 7.99 (1H, s), 7.73 (2H, m), 7.53 (4H, m), 7.36 (1H, m), 7.21 (2H, m), 6.76 (1H, m) 5.37 (2H, s, b)

m/z=287 (M+H)

Intermediate 9: 4-fluoro-3-(3-phenylimidazo[1,2-a]pyrimidin-7-yl)aniline

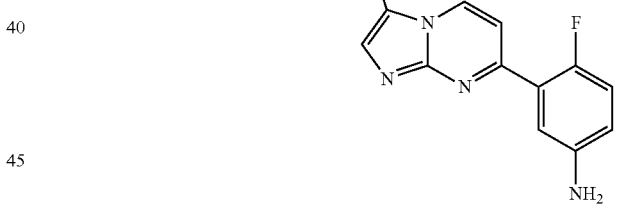

To a solution of 7-(2-fluoro-5-nitrophenyl)-3-phenylimidazo[1,2-a]pyrimidine (Intermediate 6, 0.105 g, 0.31 mmol) in ethanol (2.5 mL), iron (ALDRICH) was added followed by a solution of ammonium chloride (0.066 g, 1.24 mmol) in water (0.75 mL). The reaction mixture was allowed to warm up to 75° C. and stirred at this temperature for 1 h. UPLC check showed the reaction was complete. The reaction mixture was allowed to cool to rt and DCM and water were added. The mixture was passed through a phase separator and the organic portion was evaporated under reduced pressure to give the crude product (0.086 g, 91% yield) that was used directly in the next step.

$^1$H NMR (400 MHz, DMSO-d$_6$): δ 8.03 (1H, s), 7.76 (2H, m), 7.59 (2H, t), 7.48 (2H, m), 7.36 (1H, m), 7.06 (1H, m), 6.74 (1H, m), 5.25 (2H, s, b)

m/z=305 (M+H)

Intermediate 10: 4-(7-(2-fluoro-5-nitrophenyl)imidazo[1,2-a]pyrimidin-3-yl)morpholine

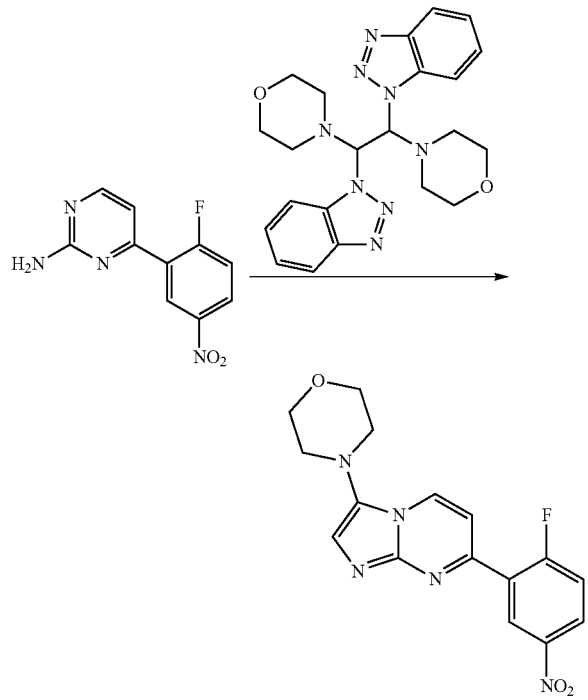

A mixture of 4-(2-fluoro-5-nitrophenyl)pyrimidin-2-amine (Intermediate 5, 0.5 g, 2.13 mmol), 1,2-bis(1H-benzo[d][1,2,3]triazol-1-yl)-1,2-dimorpholinoethane (Intermediate 1, 0.927 g, 2.13 mmol) and Zinc bromide (ALDRICH, 0.095 g, 0.42 mmol) was reflux in 1,2-dichloroethane overnight. The reaction mixture was then cooled to rt. KOH (0.12 g) was added to the solution and stirred for 30 minutes. Then, the solid was filtered out and washed with DCM. Solvents were removed under reduced pressure. Flash chromatography of the residue (SNAP KP-Si 50 g, Cy/DCM, 100:0-0:100) afforded the title compound (0.08 g, 10% yield).

$^1$H NMR (400 MHz, DMSO-d$_6$): δ 8.90 (1H, dd), 8.85 (1H, d), 8.45 (1H, m), 7.73 (1H, m), 7.61 (2H, m), 3.85 (4H, m), 3.07 (4H, m).

m/z=344 (M+H)

Intermediate 11: 4-fluoro-3-(3-morpholinoimidazo[1,2-a]pyrimidin-7-yl)aniline

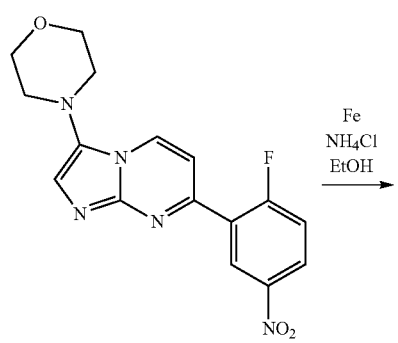

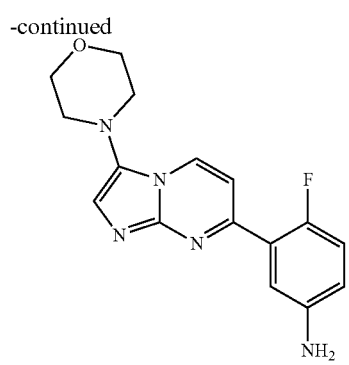

To a solution of 4-(7-(2-fluoro-5-nitrophenyl)imidazo[1,2-a]pyrimidin-3-yl)morpholine (Intermediate 10, 0.080 g, 0.23 mmol) in ethanol (2.0 mL), iron (ALDRICH, 0.104 g, 1.8 mmol) was added followed by a solution of ammonium chloride (0.049 g, 0.92 mmol) in water (0.5 mL). The reaction mixture was allowed to warm up to 75° C. and stirred at this temperature for 1 h. UPLC check showed the reaction was complete. The reaction mixture was allowed to cool to rt and DCM and water were added. The mixture was passed through a phase separator and the organic portion was evaporated under reduced pressure to give crude desired product (0.080 g) that was used directly in the next step.

m/z=314 (M+H)

Intermediate 12: 4-(7-(3-nitrophenyl)imidazo[1,2-a]pyrimidin-3-yl)morpholine

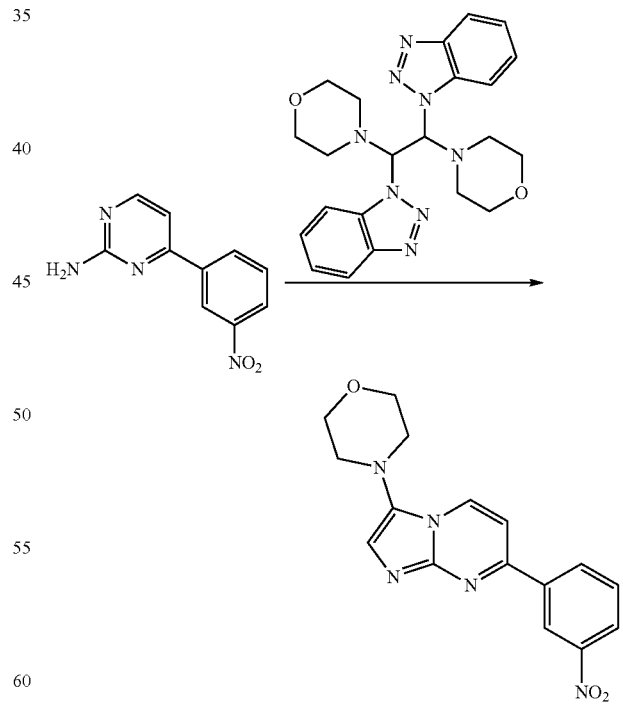

4-(3-Nitrophenyl)pyrimidin-2-amine (Intermediate 4, 0.1 g), 1,2-bis(1H-benzo[d][1,2,3]triazol-1-yl)-1,2-dimorpholinoethane (Intermediate 1, 0.2 g) and Zinc bromide (ALDRICH, 0.01 g) were suspended in 1,2-dichloroethane (3 mL) and mixture was shaken at 100° C. for 3 hours.

Mixture was washed with water, organic phase was dried and evaporated.

Crude was purified by KP-NH column eluting with cyclohexane/AcOEt 1:1, affording the desired compound as an orange solid (0.07 g).

$^1$H NMR (400 MHz, CDCl$_3$): δ 8.99 (1H, m), 8.65 (1H, m), 8.43 (1H, d), 8.37 (1H, m), 7.73 (1H, t), 7.58 (1H, s), 7.46 (1H, d), 3.96 (4H, m), 3.13 (4H, m).

Intermediate 13: 3-(3-morpholinoimidazo[1,2-a]pyrimidin-7-yl)aniline

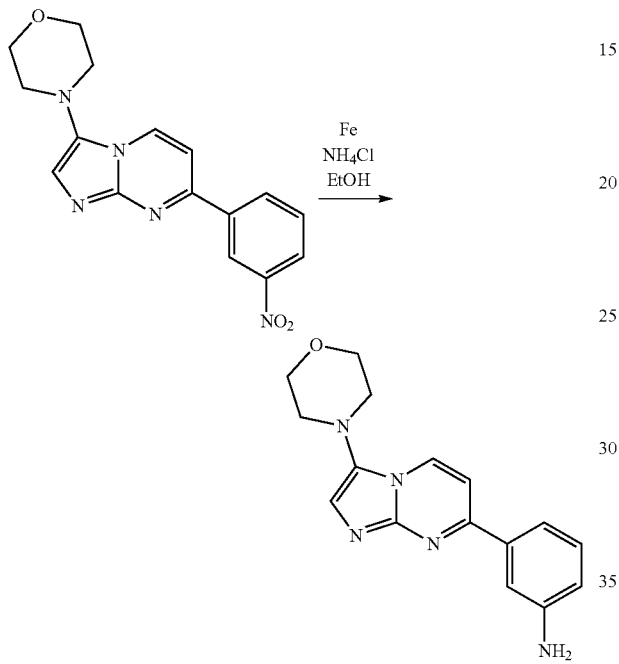

To a solution of 4-(7-(3-nitrophenyl)imidazo[1,2-a]pyrimidin-3-yl)morpholine (Intermediate 12, 0.07 g) in EtOH (5 mL), iron (ALDRICH, 0.092 g) was added followed by a sat.sol of NH$_4$Cl (2 mL), then mixture was refluxed for 1 h. After cooling to rt, the mixture was filtered over a Celite pad washing with MeOH; volatiles were evaporated and residue was diluted with AcOEt and washed with water. Organic phases were separated, dried and evaporated, affording the desired compound as a yellow solid (0.04 g) that was used for next step without further purification.

$^1$H NMR (400 MHz, CDCl$_3$): δ 8.31 (1H, d), 7.67 (1H, m), 7.48 (1H, s), 7.46 (1H, m), 7.35 (1H, d), 7.29 (1H, m), 6.83 (1H, m), 3.93 (4H, m), 3.10 (4H, m).

m/z=296 (M+H)

Intermediate 14: 4-(5-amino-2-fluorophenyl)pyrimidin-2-amine

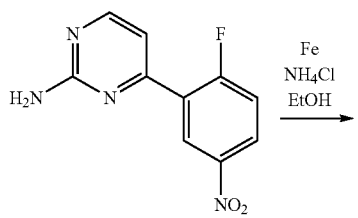

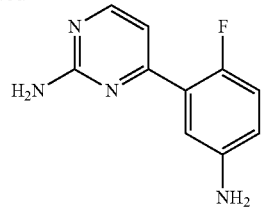

A solution of ammonium chloride (3.29 g) in water (100 mL) was added to a stirred suspension of iron powder (ALDRICH, 4.40 g) and 4-(2-fluoro-5-nitrophenyl)pyrimidin-2-amine (Intermediate 5, 4.01 g) in ethanol (150 ml) and 1,4-dioxane (150 mL) at room temperature. The resulting mixture was heated to 50° C. for 3 hours. The reaction mixture was cooled to room temperature, diluted with EtOAc (300 ml) and filtered through a short plug of Celite washing with abundant EtOAc. The filtrate was partially evaporated to remove the organic solvents then the residue was diluted with water (100 mL) and the pH adjusted to pH8 with sodium bicarbonate solution. The mixture was extracted with dichloromethane. The combined organic phases were filtered through a hydrophobic frit (Phase Separator) and evaporated under reduced pressure. The residue was chromatographed on NH-modified silica gel (SNAP 375) eluting with EtOAc to give the desired product (3.05 g) as a pale yellow solid.

Intermediate 15: N-(3-(2-aminopyrimidin-4-yl)-4-fluorophenyl)pyrrolidine-1-carboxamide

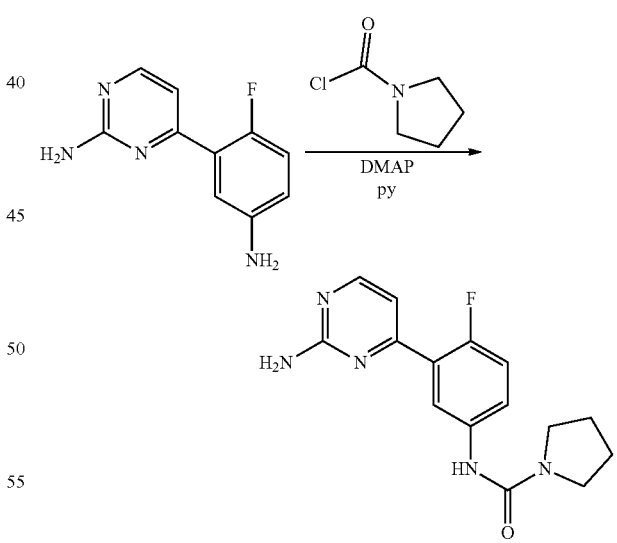

Pyrrolidine-1-carbonyl chloride (ALDRICH, 1.91 ml) was added to a stirred suspension of 4-(5-amino-2-fluorophenyl)pyrimidin-2-amine (Intermediate 14, 3.53 g) and dimethylaminepyrimidine (0.106 g) in pyridine (10 mL) and dichloromethane (100 mL) at room temperature and the resulting mixture was heated to reflux overnight. The reaction mixture was transferred to a screw-topped round bottom flask, where it was sealed and heated to 55° C. for another 24 hours. The reaction mixture was quenched with water (200 mL), the pH was adjusted to pH 7 and the mixture was extracted with dichloromethane (4×250 mL). The combined organic phases were washed with brine (100 mL), filtered through a hydrophobic frit (Phase Separator) and evaporated under reduced pressure. The residue was chromatographed on silica gel (SNAP340) eluting with a gradient of 30-100% solvent mixture A in cyclohexane, where solvent mixture A is MeOH/EtOAc 5:95, to give the desired product (2.05 g) as a white solid.

Alternatively, Intermediate 15 may be prepared by the following reaction:

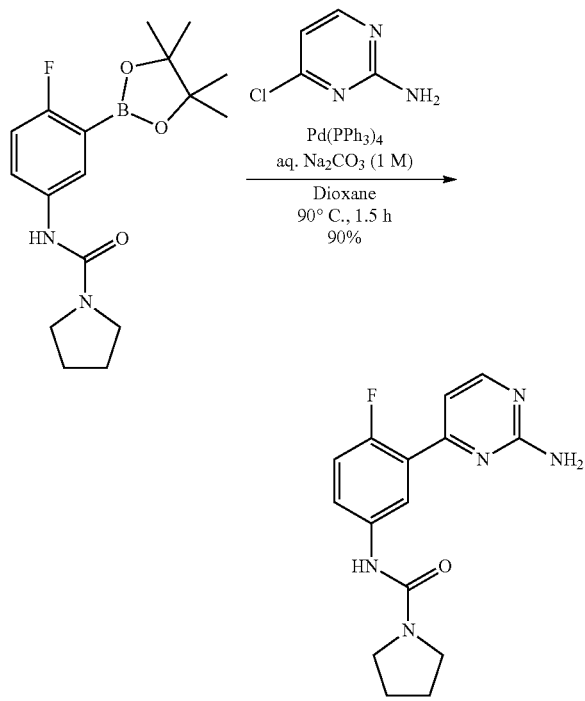

A mixture of 4-chloropyrimidin-2-amine (1.5 g, 11.58 mmol), N-(4-fluoro-3-(4,4,5,5-tetra methyl-1,3,2-dioxaborolan-2-yl)phenyl)pyrrolidine-1-carboxamide (Intermediate 17, 5.52 g, 16.52 mmol) and 1 N aqueous NaHCO₃ (23.16 mL, 23.16 mmol) in 1,4-dioxane (57.9 mL) was degassed by nitrogen. Tetrakis(triphenylphosphine)Palladium (0) (1.338 g, 1.158 mmol) was added and the resulting mixture was heated at 90° C. for 1.5 h.

The reaction was filtered through a celite pad and eluted with dichloromethane (10×35 mL). The filtrate was washed with water (150 mL), the aqueous layer extracted with dichloromethane (2×50 mL) and the organic layers were combined, dried with anhydrous Na₂SO₄, filtered and concentrated to an orange semi-solid. The residue was precipitated with diethyl ether and the resulting solid was triturated with 10% EtAcO/Et₂O, 1:3 EtAcO/Et₂O and 50% EtAcO/Et₂O to give the desired product as a pale brown solid (3.52 g).

$^1$H NMR (400 MHz, DMSO-d₆): δ 8.3-8.30 (m, 2H), 8.04 (dd, J=7.1, 2.8 Hz, 1H), 7.66-7.62 (m, 1H), 7.18 (dd, J=11.1, 8.8 Hz, 1H), 6.90 (dd, J=5.1, 2.5 Hz, 1H), 6.68 (br s, 2H), 3.38-3.34 (m, 4H), 1.87-1.83 (m, 4H).

m/z=302 (M+H)

Intermediate 16: N-(3-bromo-4-fluorophenyl)pyrrolidine-1-carboxamide

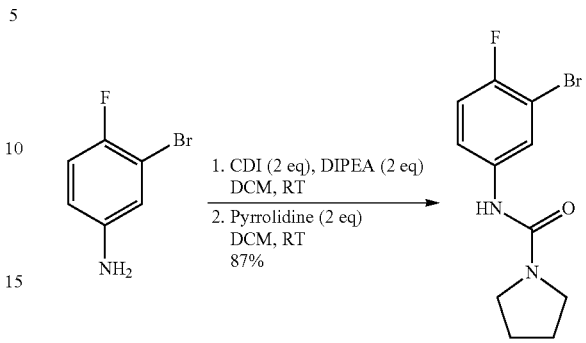

To a solution of 3-bromo-4-fluoroaniline (5 g, 26.3 mmol) in dichloromethane (150 mL), N,N-diisopropylethylamine (9.19 mL, 52.6 mmol) and 1,1'-carbonyldiimidazole (8.53 g, 52.6 mmol) were added. The resulting solution was stirred at room temperature overnight. Pyrrolidine (4.40 mL, 52.6 mmol) was added and the reaction was stirred at room temperature over 2 h. Water (slightly acidified) was added and the layers were separated. The aqueous layer was extracted with dichloromethane (60 mL). The organic layers were combined, dried with anhydrous Na₂SO₄, filtered and concentrated. The residue was triturated with diethyl ether to give the desired product (6.57 g, white solid).

$^1$H NMR (400 MHz, DMSO-d₆): δ 8.28 (br s, 1H), 7.93-7.71 (m, 1H), 7.53-7.49 (m, 1H), 7.24 (, t, J=8.8 Hz, 1H), 3.36-3.32 (m, 4H), 1.86-1.83 (m, 4H).

Intermediate 17. N-(4-fluoro-3-(4,4,5,5-tetramethyl-1,3,2-dioxaborolan-2-yl)phenyl)pyrrolidine-1-carboxamide

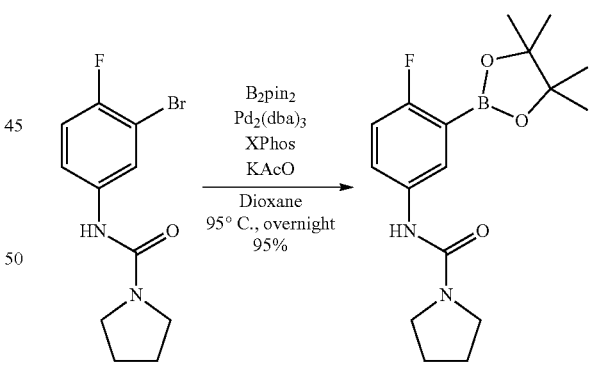

A suspension of N-(3-bromo-4-fluorophenyl)pyrrolidine-1-carboxamide (Intermediate 16, 5 g, 17.41 mmol), bis(pinacolato)diboron (6.63 g, 26.1 mmol) and potassium acetate (4.27 g, 43.5 mmol) in 1,4-Dioxane (62.4 mL) was degassed. Xphos (0.697 g, 1.463 mmol) and Pd₂(dba)₃ (0.399 g, 0.435 mmol) were then added. Following two cycles of vaccum/nitrogen, the suspension was heated at 90° C. overnight. The reaction was filtered through a celite pad, eluted with dichloromethane, and the filtrate concentrated in vacuo to give a red solid (12.6 g). The residue was triturated with diethyl ether (3×10 mL) to give the desired product as a cream solid (5.52 g).

¹H NMR (400 MHz, DMSO-d₆): δ 8.19 (br s, 1H), 7.75-7.70 (m, 2H), 7.02-6.97 (m, 1H), 3.36-3.33 (m, 4H), 1.85-1.82 (m, 4H), 1.29 (br s, 12H).
m/z=335 (M+H)

Intermediate 24.
5-(3-nitrophenyl)-1,2,4-triazin-3-amine

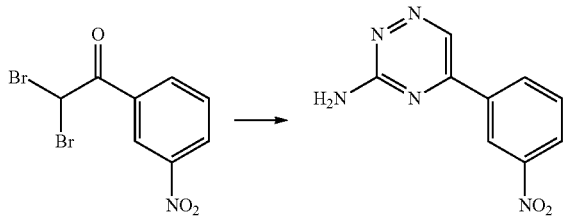 [SMILES: O=C(c1cccc([N+](=O)[O-])c1)C(Br)Br ; Nc1nncc(-c2cccc([N+](=O)[O-])c2)n1]

Prepared according to the method of Kim, Junwon et al., (Med. Chem. Lett., 2012, 3(8), 678-682) from 2,2-dibromo-1-(3-nitrophenyl)ethanone (5.50 g, 17.0 mmol, prepared by dibromination of commercially available 3-nitrophenylethanone according to K., Shoji et al. *Bull. Chem. Soc. Japan*, 1987, 60(7), 2667), THF (100 mL), morpholine (6.23 g, 71.5 mmol) and 1-aminoguanidine hydrogen carbonate (ALFA AESAR, 2.3 g, 17.0 mmol) to give 5-(3-nitrophenyl)-1,2,4-triazin-3-amine (2.11 g, 54% yield) as a white powder.

¹H NMR (500 MHz, DMSO-d₆): δ 9.39 (1H, s), 8.99 (1H, s), 8.62 (1H, d, J=7.9 Hz), 8.44 (1H, d, J=8.3 Hz), 7.88 (1H, t, J=7.8 Hz), 7.46 (2H, s br).

Intermediate 26. 3-(3-nitrophenyl)imidazo[1,2-b][1,2,4]triazine

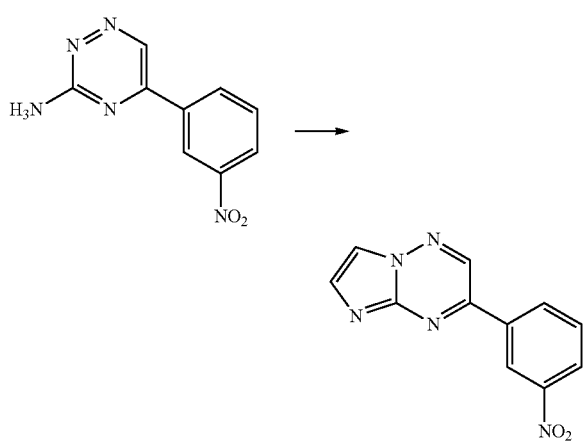

A stirred solution of 2-bromo-1,1-diethoxy-ethane (ALDRICH, 5.60 g, 28.4 mmol) in HBr (48% aqueous, 0.50 mL) and ethanol (20 mL) was stirred at 90° C. for 1 h, cooled, diluted with Ethanol (10 ml) and basified by careful addition of solid NaHCO₃. The mixture was filtered, washed with ethanol (10 mL), 5-(3-nitrophenyl)-1,2,4-triazin-3-amine (Intermediate 24, 1.30 g, 5.7 mmol) added to the filtrate and the solution stirred overnight at 100° C. The reaction was cooled, the solvent concentrated in vacuo and crude material partitioned between water (50 mL) and EtOAc (50 mL). The organic phase was washed with brine (10 mL), filtered through a phase separator containing MgSO₄ and concentrated in vacuo. Diethylether was added and resulting solid collected, washed with diethylether and dried under vacuum to give 3-(3-nitrophenyl)imidazo[1,2-b][1,2,4]triazine (1.33 g, 97% yield) as a tan powder.

¹H NMR (500 MHz, DMSO-d₆): δ 9.56 (1H, s), 9.01 (1H, s), 8.74 (1H, d, J=7.8 Hz), 8.47 (1H, s), 8.43 (1H, d, J=8.1 Hz), 8.10 (1H, s), 7.91 (1H, t, J=7.9 Hz).

Intermediate 27. 7-bromo-3-(3-nitrophenyl)imidazo[1,2-b][1,2,4]triazine

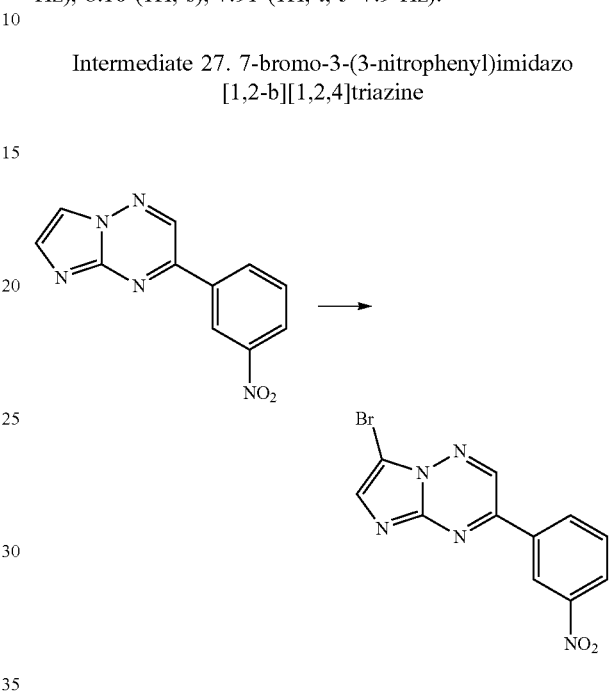

A stirred solution of 3-(3-nitrophenyl)imidazo[1,2-b][1,2,4]triazine (Intermediate 26, 1.32 g, 5.5 mmol) in acetic acid (10 mL) at rt was treated with sodium acetate (6.73 g, 8.2 mmol) followed by bromine (0.962 g, 6.0 mmol) and stirred for 1 hour. The reaction mixture was then added dropwise to a stirred mixture of saturated aqueous NaHCO₃ (20 mL) and EtOAc (20 mL) and the resulting solid collected, washed with water, EtOAc and dried under vacuum to give 7-bromo-3-(3-nitrophenyl)imidazo[1,2-b][1,2,4]triazine (1.2 g, 65% yield) as a tan powder.

¹H NMR (500 MHz, DMSO-d₆): δ 9.68 (1H, s), 9.08 (1H, s), 8.76 (1H, d, J=7.8 Hz), 8.45 (1H, d, J=8.1 Hz), 8.24 (1H, s), 7.93 (1H, t, J=7.9 Hz).

Intermediate 29. 3-(3-nitrophenyl)-7-phenylimidazo[1,2-b][1,2,4]triazine

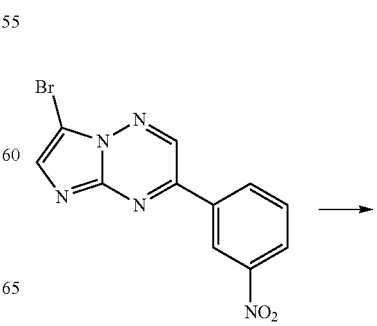

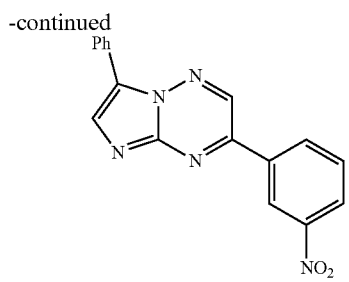

A solution of 7-bromo-3-(3-nitrophenyl)imidazo[1,2-b][1,2,4]triazine (Intermediate 27, 0.2 g, 0.59 mmol), 4,4,5,5-tetramethyl-2-phenyl-1,3,2-dioxaborolane (ALDRICH, 0.242 g, 1.19 mmol), tetrakis (triphenylphosphine)palladium (ALDRICH, 0.069 g, 0.06 mmol) and sodium carbonate (0.188 g, 1.78 mmol) in DMF (3 mL) and water (1 mL) was stirred overnight at 80° C. in a sealed tube. The reaction mixture was then poured onto a well stirred mixture of water (10 mL) and EtOAc (10 mL) and the resulting solid collected, washed with water, EtOAc and dried in vacuo to give 3-(3-nitrophenyl)-7-phenyl-imidazo[1,2-b][1,2,4]triazine (0.18 g, 91% yield) as a tan powder.

$^1$H NMR (500 MHz, DMSO-d$_6$): δ 9.67 (1H, s), 9.10 (1H, s), 8.78 (1H, d, J=7.9 Hz), 8.65 (1H, s), 8.44 (1H, d, J=8.2 Hz), 8.21 (2H, d, J=7.7 Hz), 7.94 (1H, t, J=8.1 Hz), 7.60 (2H, t, J=8.0 Hz), 7.47 (1H, t, J=7.1 Hz).

Intermediate 30: 4-(3-(3-nitrophenyl)imidazo[1,2-b][1,2,4]triazin-7-yl)morpholine

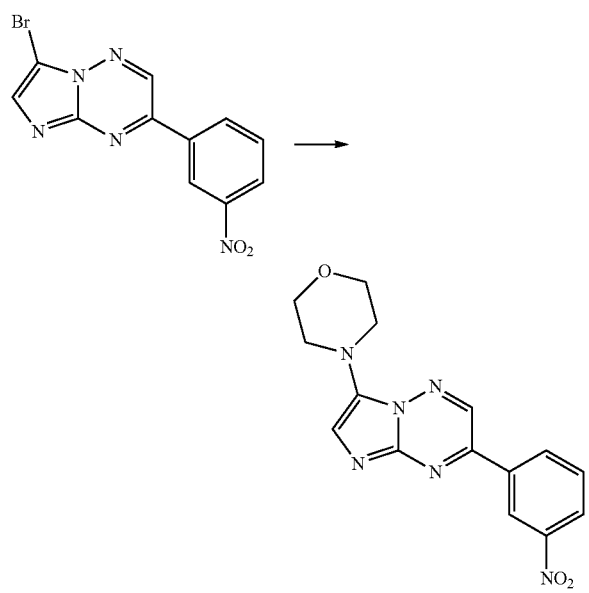

A solution of 7-bromo-3-(3-nitrophenyl)imidazo[1,2-b][1,2,4]triazine (Intermediate 27, 0.4 g, 1.25 mmol), morpholine (ALDRICH, 0.544 g, 6.25 mmol), caesium carbonate (ADLRICH, 0.814 g, 2.5 mmol), tris(dibenzylideneacetone)dipalladium(0) (ALDRICH, 0.057 g, 0.063 mmol) and Xantphos (ALDRICH, 0.072 g, 0.13 mmol) in 1,4-dioxane (5 mL) was heated with stirring in a microwave at 150° C. for 2 h. The reaction mixture was then poured into EtOAc (10 mL) and water (10 mL), the organic phase was separated, washed with brine (10 mL), dried (MgSO$_4$) and evaporated. Chromatography (SiO$_2$, 100% EtOAc) gave 4-[3-(3-nitrophenyl)imidazo[1,2-b][1,2,4]triazin-7-yl]morpholine (0.075 g, 18% yield) as a yellow powder.

$^1$H NMR (500 MHz, DMSO-d$_6$): δ 9.45 (1H, s), 9.01 (1H, s), 8.69 (1H, d, J=8.0 Hz), 8.39 (1H, d, J=8.0 Hz), 7.89 (1H, t, J=8.8 Hz), 7.72 (1H, s), 3.84 (4H, s br), 3.28 (4H, s br).

Intermediate 31. N-[3-(2,2-dibromoacetyl)-4-fluorophenyl]pyrrolidine-1-carboxamide

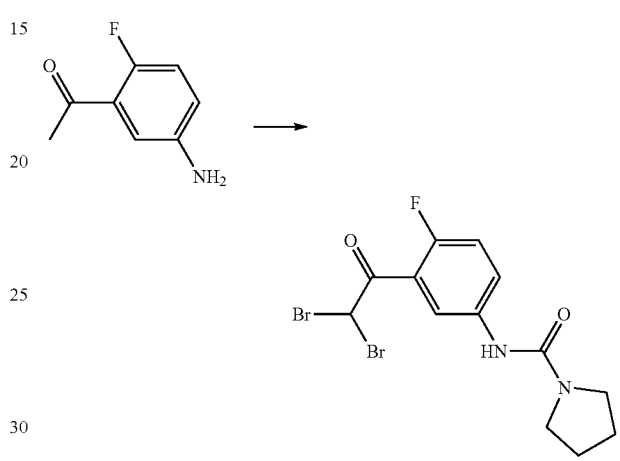

A stirred solution of 1-(5-amino-2-fluoro-phenyl)ethanone (APOLLO, 10.0 g, 65.3 mmol) and DMAP (0.4 g, 3.3 mmol) in pyridine (100 mL) and DCM (400 mL) at rt was treated dropwise with pyrrolidine-1-carbonyl chloride (ALDRICH, 13.08 g, 97.9 mmol). The reaction was stirred at 50° C. for 72 h until TLC (hexane/EtOAc 1:1) revealed reaction had gone to completion. The reaction was then concentrated in vacuo, the residual thick oil diluted with DCM (400 mL), washed with brine (200 mL) then 1M hydrochloric acid (200 mL) and the organic phase dried (MgSO$_4$), concentrated in vacuo to give a powder which was triturated with 1:1 EtOAc:Et$_2$O (200 mL), stirred at rt for 12 h then collected by filtration and dried to give N-(3-acetyl-4-fluoro-phenyl)pyrrolidine-1-carboxamide (13.55 g, 82% yield) as a faintly lilac powder.

$^1$H NMR (500 MHz, DMSO-d$_6$): δ 8.37 (1H, s), 7.94 (1H, dd, J=6.7 Hz, 2.8 Hz), 7.85-7.81 (1H, m), 7.23 (1H, dd, J=10.9 Hz, 9.0 Hz), 3.38-3.34 (4H, m), 2.56 (3H, d, J=4.6 Hz), 1.88-1.83 (4H, m).

To a solution of N-(3-acetyl-4-fluoro-phenyl)pyrrolidine-1-carboxamide (1.70 g, 6.45 mmol) in THF (50 mL) was then added trimethylphenylammonium tribromide (ALDRICH, 9.70 g, 25.8 mmol) in portions, the reaction stirred at rt for 10 min then the reaction warmed to 60° C. and stirred for 12 h. The reaction mixture was then filtered to remove solid, the solvent removed in vacuo and the residue chromatographed (SiO$_2$, 5-90% EtOAc/heptane) to give N-[3-(2,2-dibromoacetyl)-4-fluoro-phenyl]pyrrolidine-1-carboxamide (1.26 g, 46% yield) as a light brown solid.

$^1$H NMR (500 MHz, CDCl$_3$): δ 8.07-8.03 (1H, m), 7.71-7.67 (1H, m), 7.15 (1H, t, J=10.0 Hz), 6.89-6.86 (1H, m), 6.43 (1H, s), 3.50 (4H, s), 2.05 (4H, s).

Intermediate 32. N-(3-(3-amino-1,2,4-triazin-5-yl)-4-fluorophenyl)pyrrolidine-1-carboxamide

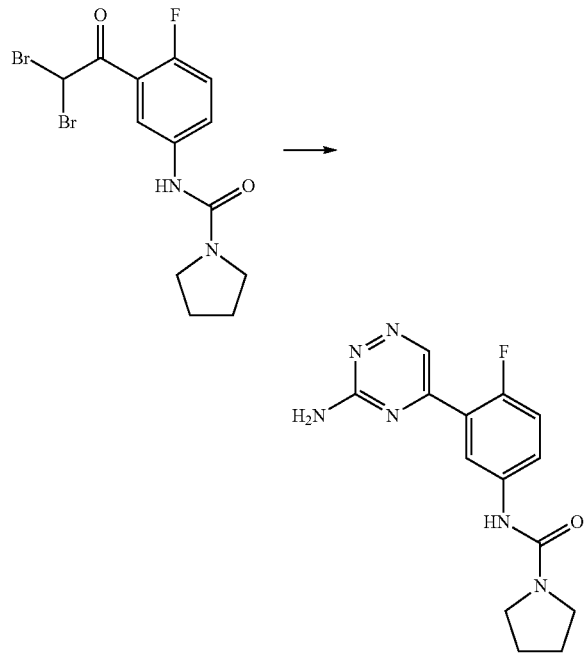

Prepared according to the method of Intermediate 24, 3-(3-nitrophenyl)imidazo[1,2-b][1,2,4]triazine from N-[3-(2,2-dibromoacetyl)-4-fluoro-phenyl]pyrrolidine-1-carboxamide (intermediate 31, 1.47 g, 3.60 mmol), morpholine (ALDRICH, 1.32 g, 15.13 mmol) and 1-aminoguanidine hydrogen carbonate (ALFA AESAR, 0.487 g, 3.60 mmol) in acetic acid (44 mg, 0.74 mmol) to give N-[3-(3-amino-1,2,4-triazin-5-yl)-4-fluoro-phenyl]pyrrolidine-1-carboxamide (0.295 g, 26% yield) as a pale yellow powder.

$^1$H NMR (500 MHz, DMSO-d$_6$): δ 8.93 (1H, s), 8.40 (1H, s), 8.12 (1H, d, J=6.3 Hz), 7.76-7.70 (1H, m), 7.32 (2H, s br), 7.28 (1H, t, J=10.0 Hz), 3.38 (4H, s), 1.87 (4H, s).

EXAMPLES

Example 1: N-(3-(3-morpholinoimidazo[1,2-a]pyrimidin-7-yl)phenyl)pyrrolidine-1-carboxamide

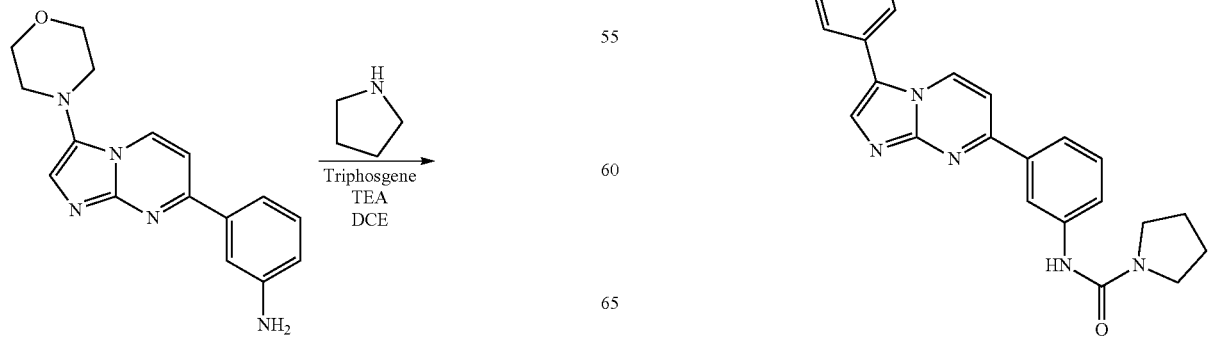

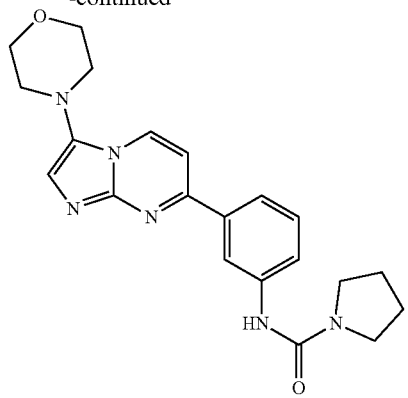

Triphosgene (ALDRICH, 0.163 g, 0.55 mmol) was added to a stirred suspension of 3-(3-morpholinoimidazo[1,2-a]pyrimidin-7-yl)aniline (Intermediate 13, 0.04 g) in 1,2-dichloroethane (3 mL) at room temperature. The mixture was stirred for 5 minutes. Triethylamine (ALDRICH, 0.03 mL) was added at 0° C. and the mixture was stirred at rt for 30 minutes. Pyrrolidine (ALDRICH, 0.124 mL) was added and the mixture was stirred for 1 hour. The mixture was diluted with DCM, water was added and stirring was continued for 5 min. The phases were separated and the organic phase was dried and evaporated. Crude product was purified by KP-NH column eluting with AcOEt 100%, affording the desired compound as a yellow solid (0.030 g).

$^1$H NMR (400 MHz, CDCl$_3$): δ 8.47 (1H, m), 8.22 (1H, s, b), 7.81 (2H, m), 7.48 (3H, m), 7.19 (1H, m), 3.95 (4H, m), 3.59 (4H, m), 3.13 (4H, m), 2.03 (4H, m).

m/z=393 (M+H)

Example 2: N-(3-(3-phenylimidazo[1,2-a]pyrimidin-7-yl)phenyl)pyrrolidine-1-carboxamide

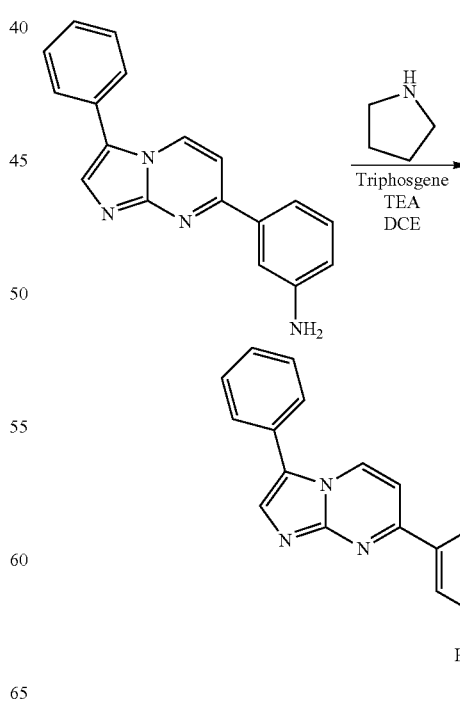

Triphosgene (ALDRICH, 0.025 g, 0.086 mmol) was added to a stirred solution of 3-(3-phenylimidazo[1,2-a]pyrimidin-7-yl)aniline (Intermediate 8, 0.07 g, 0.24 mmol) in 1,2-dichloroethane (1 ml) at room temperature. The mixture was stirred for 5 minutes during which time a precipitate formed. The mixture was cooled down to 0° C. and triethylamine (ALDRICH, 0.066 mL) was added; the mixture was stirred at rt for 30 minutes. Further triethylamine (0.006 mL) and pyrrolidine (ALDRICH, 0.020 mL) were added and the mixture was stirred for 1 hour. UPLC check showed the reaction was complete. Water was added and the mixture was extracted with DCM. The organic phase was evaporated under reduced pressure. Chromatography of the residue (SNAP Cartridge, KP-NH, 12 g, DCM/MeOH, 100:0-95:5) afforded the title compound as a yellow solid (0.035 g, 38% yield).

$^1$H NMR (400 MHz, DMSO-$d_6$): δ 9.08 (1H, d), 8.43 (2H, d), 8.00 (1H, s), 7.76 (4H, m), 7.61 (3H, m), 7.44 (2H, m), 3.42 (4H, m), 1.88 (4H, m)

m/z=384 (M+H)

Example 3: N-(4-fluoro-3-(3-phenylimidazo[1,2-a]pyrimidin-7-yl)phenyl)pyrrolidine-1-carboxamide

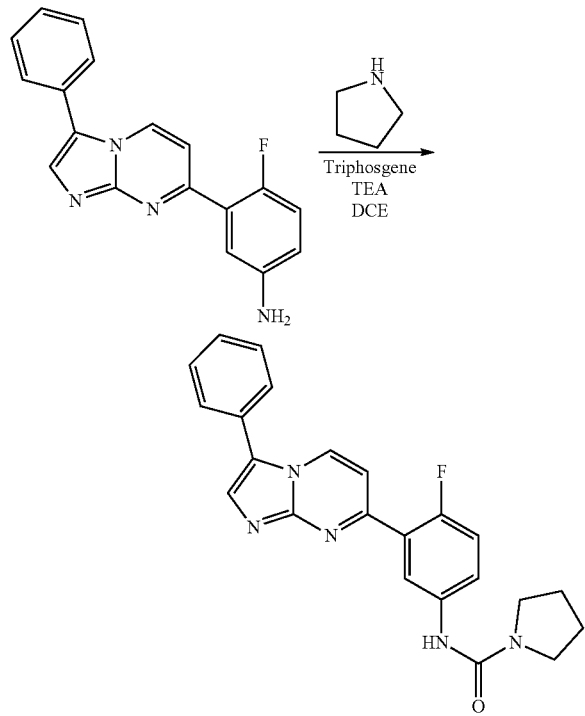

Triphosgene (ALDRICH, 0.029 g, 0.10 mmol) was added to a stirred solution of 4-fluoro-3-(3-phenylimidazo[1,2-a]pyrimidin-7-yl)aniline (Intermediate 9, 0.086 g, 0.28 mmol) in 1,2-dichloroethane (6 ml) at room temperature. The mixture was stirred for 5 minutes during which time a precipitate formed. The mixture was cooled down to 0° C. and triethylamine (ALDRICH, 0.078 mL) was added; the mixture was stirred at rt for 30 minute. Further triethylamine (0.008 mL) and pyrrolidine (ALDRICH, 0.023 mL) were added and the mixture was stirred for 1 hour. UPLC check showed the reaction was complete. Water was added and the mixture was extracted with DCM. The organic phase was evaporated under reduced pressure. Chromatography of the residue (SNAP Cartridge, KP-NH, 12 g, DCM) afforded the title compound as a yellow solid (0.050 g). NMR showed the presence of DCM. The compound was dissolved in MeOH and the solution was evaporated under reduced pressure affording the desired compound (0.048 g, 42% yield).

$^1$H NMR (400 MHz, DMSO-$d_6$): δ 9.10 (1H, d), 8.45 (1H, s), 8.29 (1H, dd), 8.07 (1H, s), 7.82 (1H, m), 7.77 (2H, m), 7.60 (2H, m), 7.50 (2H, m), 7.29 (1H, m), 3.41 (4H, m), 1.88 (4H, m).

m/z=402 (M+H)

Example 4: N-(4-fluoro-3-(3-morpholinoimidazo[1,2-a]pyrimidin-7-yl)phenyl)pyrrolidine-1-carboxamide

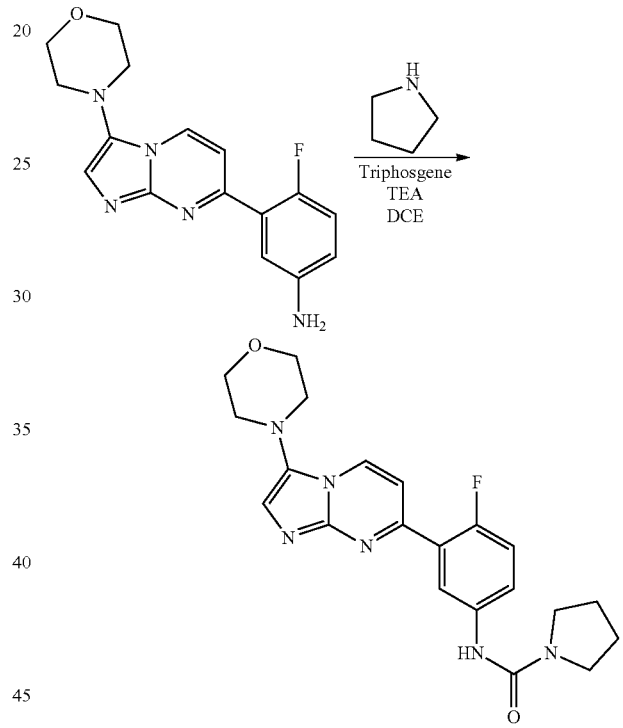

Triphosgene (ALDRICH, 0.087 g, 0.29 mmol) was added to a stirred solution of 4-fluoro-3-(3-morpholinoimidazo[1,2-a]pyrimidin-7-yl)aniline (Intermediate 11, 0.260 g, 0.83 mmol) in 1,2-dichloroethane (17 mL) at room temperature. The mixture was stirred for 5 minutes during which time a precipitate formed. The mixture was cooled down to 0° C. and triethylamine (0.23 mL, 1.66 mmol) was added; the mixture was stirred at rt for 30 minute. Further triethylamine (0.023 mL) and pyrrolidine (ALDRICH, 0.069 mL, 0.83 mmol) were added and the mixture was stirred for 1 hour. UPLC check showed the reaction was complete. Water was added and the mixture was extracted with DCM. The organic phase was evaporated under reduced pressure. Chromatography of the residue (SNAP Cartridge, KP-NH, 28 g DCM/MeOH 95:5) afforded the title compound as a yellow solid. NMR showed the presence of DCM. The product was dissolved in MeOH and the solution was evaporated under reduced pressure affording the desired compound as a yellow solid (0.070 g, 42% yield).

$^1$H NMR (500 MHz, DMSO-d$_6$) δ ppm 1.83-1.91 (m, 4H), 3.01-3.07 (m, 4H), 3.36-3.41 (m, 4H), 3.79-3.83 (m, 4H), 7.25 (dd, J=11.53, 9.06 Hz, 1H), 7.41 (dd, J=7.40, 2.20 Hz, 1H), 7.51 (s, 1H), 7.75-7.80 (m, 1H), 8.20 (dd, J=7.14, 2.74 Hz, 1H), 8.41 (s, 1H), 8.75 (d, J=7.41 Hz, 1H)

m/z=411 (M+H)

Example 5: N-(4-fluoro-3-(3-(piperidin-1-yl)imidazo[1,2-a]pyrimidin-7-yl)phenyl)pyrrolidine-1-carboxamide

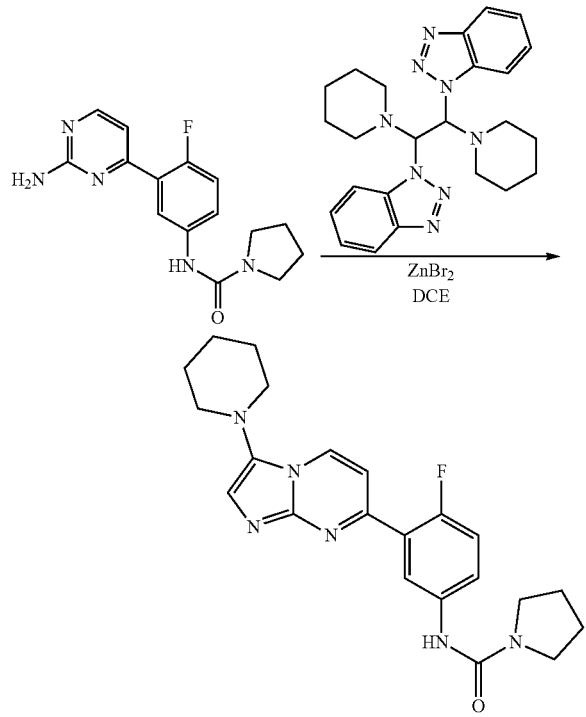

N-[3-(2-Aminopyrimidin-4-yl)-4-fluorophenyl]pyrrolidine-1-carboxamide (Intermediate 15, 0.2 g) was added to a stirred suspension of 1-[2-(1H-1,2,3-benzotriazol-1-yl)-1,2-bis(piperidin-1-yl)ethyl]-1H-1,2,3-benzotriazole (prepared using similar procedures as for Intermediate 1, 0.567 g) in 1,2-dichloroethane (13 mL) at room temperature. Zinc bromide (0.148 g) was added and the mixture was warmed to 70° C. for 4 hours during which time a precipitate formed.

The reaction mixture was cooled to room temperature, diluted with dichloromethane and washed with water. The phases were separated and the aqueous phase was extracted further with dichloromethane. The combined organic phases were dried (Na$_2$SO$_4$), filtered and evaporated under reduced pressure. Flash chromatography of the residue (SNAP KP-NH, DCM-MeOH, 100:0-95:5) and further purification by preparative HPLC afforded the desired product (21 mg, 9%) as a yellow solid $^1$H NMR (400 MHz, CDCl$_3$): δ 8.63 (d, 1H), 8.44-8.4 (br s, 1H), 8.24-8.2 (dd, 1H), 7.82-7.76 (m, 1H), 7.45-7.4 (dd, 2H), 7.3-7.22 (m, 1H), 3.44-3.37 (m, 4H), 3.1-2.9 (m, 4H), 1.92-1.84 (m, 4H), 1.78-1.71 (br, 4H), 1.65-1.58 (br, 2H).

m/z=408 (M+H)

Example 6. N-(3-(7-bromoimidazo[1,2-b][1,2,4]triazin-3-yl)-4-fluorophenyl)pyrrolidine-1-carboxamide

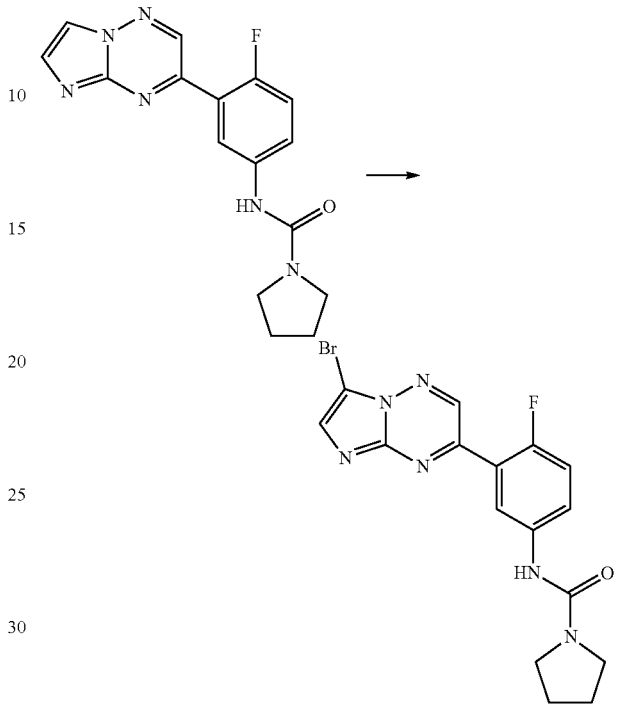

Prepared according to the method of Intermediate 27, 7-bromo-3-(3-nitrophenyl)imidazo[1,2-b][1,2,4]triazine from N-[4-fluoro-3-(7-morpholinoimidazo[1,2-b][1,2,4]triazin-3-yl)phenyl]pyrrolidine-1-carboxamide (Example 11, 0.085 g, 0.26 mmol) in acetic acid (1 mL), sodium acetate (0.032 g, 0.39 mmol) and bromine (0.046 g, 0.29 mmol) to give the desired product (0.058 g, 49% yield) as a pale yellow powder.

$^1$H NMR (400 MHz, DMSO-d$_6$): δ 9.17 (s, 1H), 8.48 (s, 1H), 8.29 (m, 1H), 8.21 (s, 1H), 7.85 (m, 1H), 7.34 (dd, 1H), 3.41 (m, 4H), 1.87 (m, 4H).

m/z=405 (M+H)

Example 7: N-(4-fluoro-3-(7-phenylimidazo[1,2-b][1,2,4]triazin-3-yl)phenyl)pyrrolidine-1-carboxamide

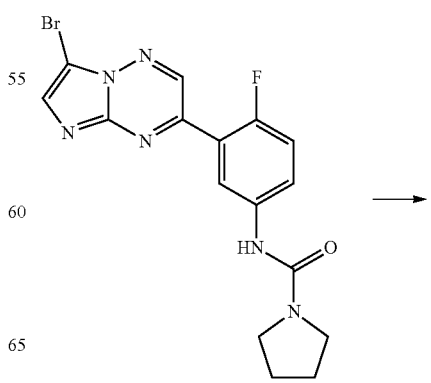

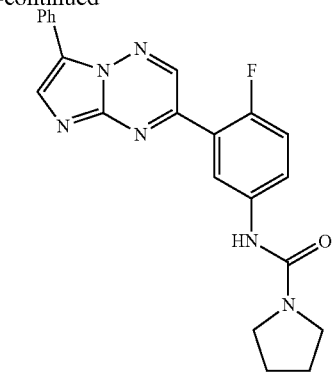

Prepared according to the method of Intermediate 29, 3-(3-nitrophenyl)-7-phenylimidazo[1,2-b][1,2,4]triazine from N-[3-(7-bromoimidazo[1,2-b][1,2,4]triazin-3-yl)-4-fluoro-phenyl]pyrrolidine-1-carboxamide (Example 6, 0.03 g, 0.074 mmol), 4,4,5,5-tetramethyl-2-phenyl-1,3,2-dioxaborolane (ALDRICH, 0.03 g, 0.15 mmol), sodium carbonate (0.024 g, 0.22 mmol) and tetrakis (triphenylphosphine) palladium (ALDRICH, 0.0017 g, 0.0015 mmol) in DMF (1.5 mL) and water (0.5 mL) at 80° C. to give the desired product (0.012 g, 38% yield) as a pale yellow powder.

$^1$H NMR (400 MHz, DMSO-$d_6$): δ 9.16 (s, 1H), 8.61 (s, 1H), 8.48 (s, 1H), 8.34 (d, 1H), 8.22 (m, 2H), 7.86 (m, 1H), 7.59 (m, 2H), 7.45 (dd, 1H), 7.34 (dd, 1H), 3.41 (m, 4H), 1.88 (m, 4H). m/z=403 (M+H)

Example 8: N-(4-fluoro-3-(7-morpholinoimidazo[1,2-b][1,2,4]triazin-3-yl)phenyl)pyrrolidine-1-carboxamide

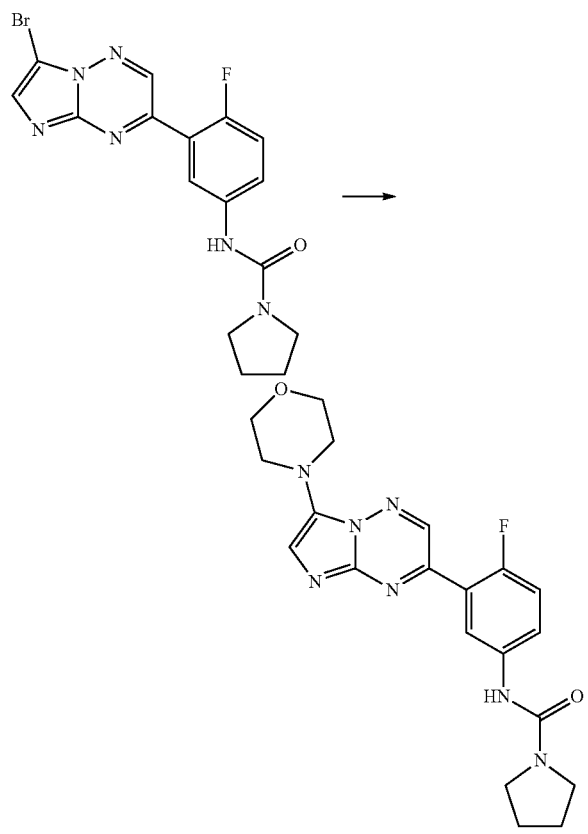

Prepared according to the method of Intermediate 30, 4-(3-(3-nitrophenyl)imidazo[1,2-b][1,2,4]triazin-7-yl)morpholine from N-[3-(7-bromoimidazo[1,2-b][1,2,4]triazin-3-yl)-4-fluoro-phenyl]pyrrolidine-1-carboxamide (Example 6, 0.126 g, 0.28 mmol), morpholine (ALDRICH, 0.122 g, 1.4 mmol), caesium carbonate (0.182 g, 0.56 mmol), tris(dibenzylideneacetone)dipalladium(0) (ALDRICH, 0.013 g, 0.014 mmol) and Xantphos (ALDRICH, 0.016 g, 0.028 mmol) in 1,4-Dioxane (3 mL) to give the desired product (0.015 g, 12% yield) as a pale yellow powder.

$^1$H NMR (400 MHz, DMSO-$d_6$): δ 8.97 (s, 1H), 8.44 (s, 1H), 8.24 (m, 1H), 7.81 (m, 1H), 7.67 (s, 1H), 7.30 (dd, 1H), 3.83 (m, 4H), 3.39 (m, 4H), 3.29 (m, 4H), 1.87 (m, 4H). m/z=412 (M+H)

Example 9: N-(3-(7-morpholinoimidazo[1,2-b][1,2,4]triazin-3-yl)phenyl)pyrrolidine-1-carboxamide

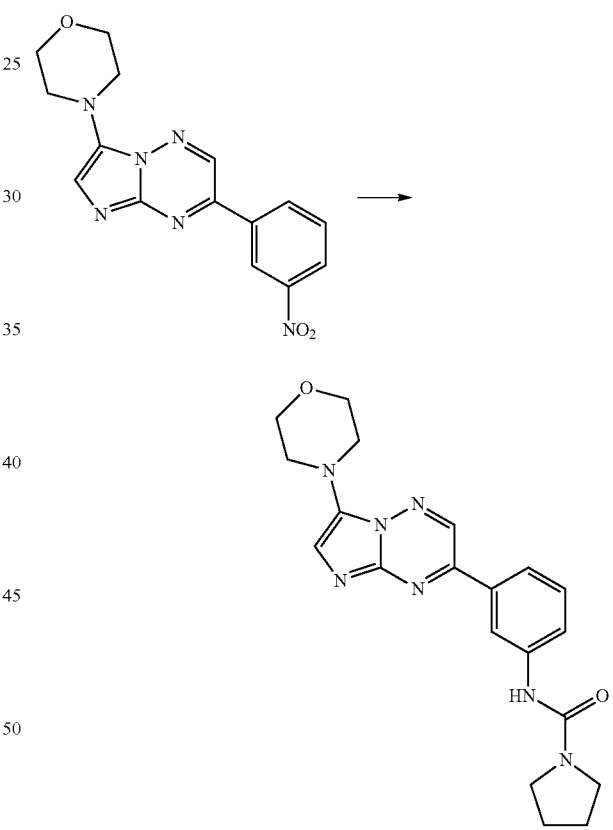

Prepared according to the method of Example 10 from 4-[3-(3-nitrophenyl)imidazo[1,2-b][1,2,4]triazin-7-yl]morpholine (Intermediate 30, 0.06 g, 0.18 mmol), iron powder (ALDRICH, 0.041 g, 0.74 mmol), ammonium chloride (0.039 g, 0.74 mmol), pyrrolidine-1-carbonyl chloride (ALDRICH, 0.049 g, 0.37 mmol) and DMAP (0.002 g) to give the desired product (0.010 g, 13% yield) as a pale yellow powder.

$^1$H NMR (400 MHz, DMSO-$d_6$): δ 9.21 (s, 1H), 8.41 (m, 2H), 7.79 (m, 2H), 7.58 (s, 1H), 7.44 (m, 2H), 3.83 (m, 4H), 3.41 (m, 4H), 3.27 (m, 4H), 1.88 (m, 4H). m/z=394 (M+H)

Example 10. N-(3-(7-phenylimidazo[1,2-b][1,2,4]triazin-3-yl)phenyl)pyrrolidine-1-carboxamide Example 11 N-(4-fluoro-3-(imidazo[1,2-b][1,2,4]triazin-3-yl)phenyl)pyrrolidine-1-carboxamide

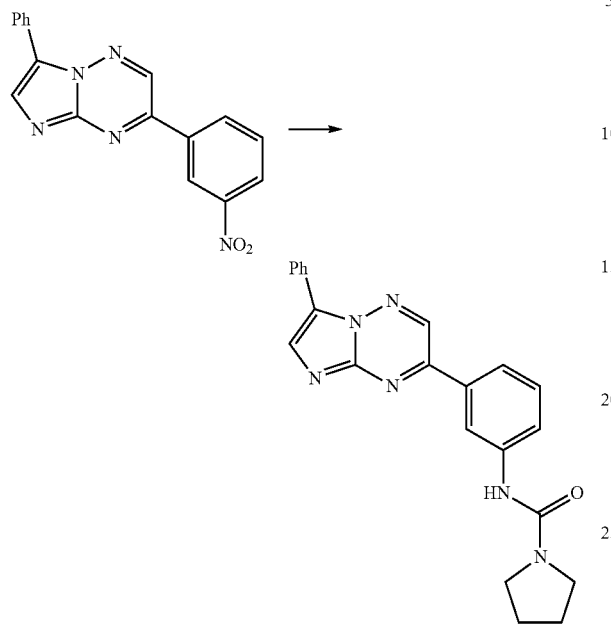

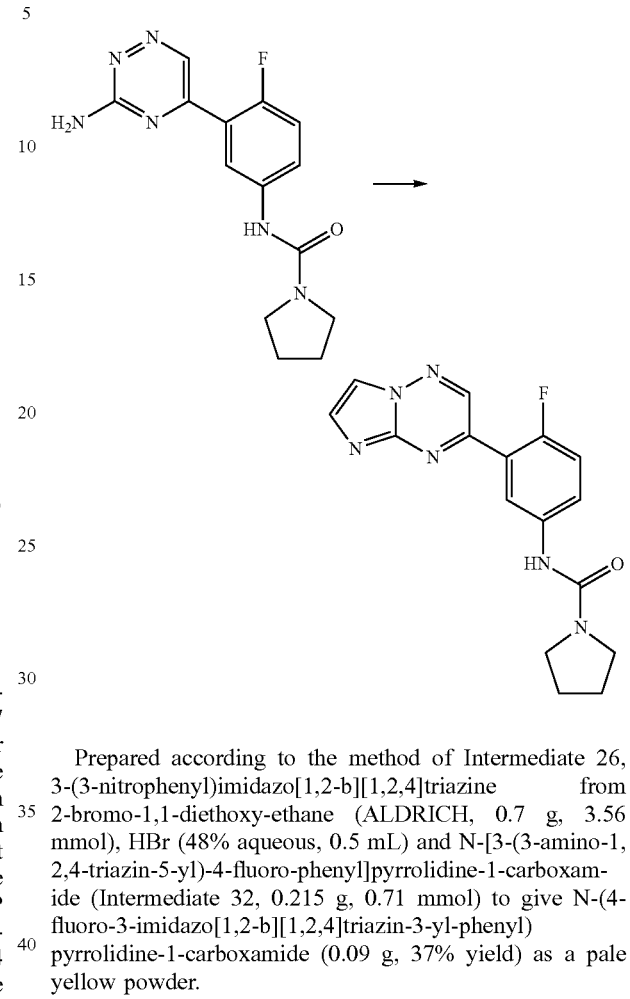

To a stirred solution of 3-(3-nitrophenyl)-7-phenyl-imidazo[1,2-b][1,2,4]triazine (Intermediate 29, 0.15 g, 0.47 mmol) in ethanol (3 me) was added a slurry of iron powder (ALDRICH, 0.106 g, 1.9 mmol) and ammonium chloride (0.025 g, 0.47 mmol) in water (0.5 mL) and the reaction heated to 80° C. for 2 h. The reaction mixture was then filtered through celite, the celite washed copiously with hot methanol, and the filtrate concentrated in vacuo. The residue was dissolved in DCM (3 mL) and pyridine (1 mL), DMAP (6 mg) added and the solution treated dropwise with pyrrolidine-1-carbonyl chloride (ALDRICH, 0.126 g, 0.94 mmol). The reaction was heated at 60° C. in a sealed tube overnight then concentrated in vacuo and the residue chromatographed (SiO$_2$, 100% EtOAc) to give the desired product (0.036 g, 19% yield) as a pale brown powder.

$^1$H NMR (400 MHz, DMSO-d$_6$): δ 9.41 (s, 1H), 8.51 (m, 2H), 8.45 (s, 1H), 8.18 (m, 2H), 7.87 (m, 2H), 7.57 (dd, 2H), 7.47 (m, 2H), 3.43 (m, 4H), 1.19 (m, 4H).

m/z=385 (M+H)

Prepared according to the method of Intermediate 26, 3-(3-nitrophenyl)imidazo[1,2-b][1,2,4]triazine from 2-bromo-1,1-diethoxy-ethane (ALDRICH, 0.7 g, 3.56 mmol), HBr (48% aqueous, 0.5 mL) and N-[3-(3-amino-1,2,4-triazin-5-yl)-4-fluoro-phenyl]pyrrolidine-1-carboxamide (Intermediate 32, 0.215 g, 0.71 mmol) to give N-(4-fluoro-3-imidazo[1,2-b][1,2,4]triazin-3-yl-phenyl)pyrrolidine-1-carboxamide (0.09 g, 37% yield) as a pale yellow powder.

$^1$H NMR (400 MHz, CDCl$_3$): δ 9.0 (s, 1H), 8.47 (m, 2H), 8.28 (d, 1H), 8.07 (s, 1H), 7.85 (m, 1H), 7.33 (dd, 1H), 3.41 (m, 4H), 1.87 (m, 4H).

m/z=326 (M+H)

The following Examples were made according to procedures analogous to those described above.

| Example | Structure / Chemical name | Physical data ($^1$H NMR or MS) |
|---|---|---|
| 12 | N-(4-fluoro-3-(5-methyl-3-morpholinoimidazo[1,2-a]pyrimidin-7-yl)phenyl)pyrrolidine-1-carboxamide | $^1$H NMR (400 MHz, DMSO-d$^6$) δ 8.48 (s, 1H), 8.37 (dd, J = 7.0, 2.7 Hz, 1H), 8.28 (s, 1H), 7.84-7.67 (m, 2H), 7.36 (dd, J = 11.1, 9.1 Hz, 1H), 3.88 (d, J = 11.3 Hz, 2H), 3.66 (t, J = 10.5 Hz, 2H), 3.39 (t, J = 6.6 Hz, 5H), 3.29-3.12 (m, 5H), 3.12-2.67 (m, 3H), 3.07-2.98 (m, 2H), 2.56-2.46 (m, 17H), 1.88 (t, J = 6.5 Hz, 4H), m/z = 424 (M + H) |

-continued

| Example | Structure Chemical name | Physical data ($^1$H NMR or MS) |
|---|---|---|
| 13 | 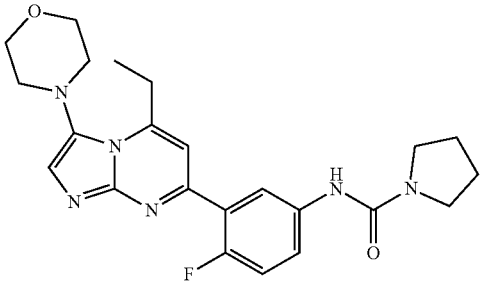<br>N-(3-(5-ethyl-3-morpholinoimidazo[1,2-a]pyrimidin-7-yl)-4-fluorophenyl)pyrrolidine-1-carboxamide | $^1$H NMR (400 MHz, DMSO-$d_6$) δ 8.41 (s, 1H), 8.18 (dd, J = 6.9, 2.8 Hz, 1H), 7.82-7.67 (m, 2H), 7.34-7.14 (m, 2H), 3.87 (d, J = 10.8 Hz, 2H), 3.64 (dd, J = 11.3, 9.2 Hz, 3H), 3.39 (t, J = 6.8 Hz, 6H), 3.14-2.96 (m, 4H), 1.87 (t, J = 6.6 Hz, 4H), 1.34 (t, J = 7.3 Hz, 3H). m/z = 439 (M + H) |
| 14 | 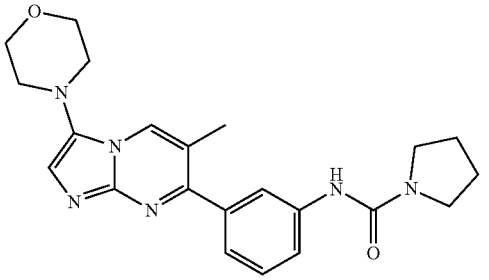<br>N-(3-(6-methyl-3-morpholinoimidazo[1,2-a]pyrimidin-7-yl)phenyl)pyrrolidine-1-carboxamide | $^1$H NMR (400 MHz, DMSO-$d_6$) δ 9.08 (s, 1H), 8.40 (s, 1H), 8.03 (d, J = 5.7 Hz, 2H), 7.68 (d, J = 8.1 Hz, 1H), 7.45 (t, J = 7.9 Hz, 1H), 7.29 (d, J = 7.9 Hz, 1H), 3.90-3.78 (m, 4H), 3.39 (t, J = 6.6 Hz, 4H), 3.19-3.02 (m, 4H), 2.56-2.52 (m, 3H), 1.87 (t, J = 6.6 Hz, 4H). m/z = 407 (M + H). |
| 15 | 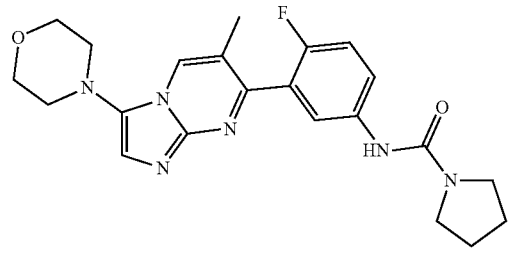<br>N-(4-fluoro-3-(6-methyl-3-morpholinoimidazo[1,2-a]pyrimidin-7-yl)phenyl)pyrrolidine-1-carboxamide | $^1$H NMR (400 MHz, DMSO-$d_6$) δ 8.61 (s, 1H), 8.32 (s, 1H), 7.67 (ddd, J = 9.1, 5.3, 2.7 Hz, 2H), 7.45 (s, 1H), 7.24 (t, J = 9.2 Hz, 1H), 3.93-3.73 (m, 4H), 3.37 (t, J = 6.6 Hz, 4H), 3.12-2.95 (m, 4H), 2.21 (s, 3H), 1.86 (t, J = 6.6 Hz, 4H). m/z = 425 (M + H) |
| 16 | 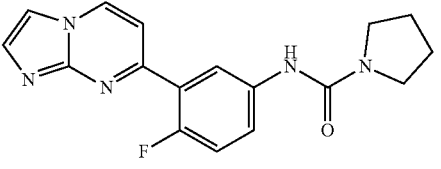<br>N-(4-fluoro-3-(imidazo[1,2-a]pyrimidin-7-yl)phenyl)pyrrolidine-1-carboxamide | $^1$H NMR (400 MHz, DMSO-$d_6$) δ 9.05 (d, J = 7.1 Hz, 1H), 8.43 (s, 1H), 8.23 (dd, J = 7.1, 2.7 Hz, 1H), 7.99 (d, J = 1.3 Hz, 1H), 7.89-7.71 (m, 2H), 7.46 (dd, J = 7.1, 2.0 Hz, 1H), 7.27 (dd, J = 11.3, 9.0 Hz, 1H), 3.35 (s, 4H), 1.87 (t, J = 6.6 Hz, 4H). m/z = 326 (M + H) |
| 17 | 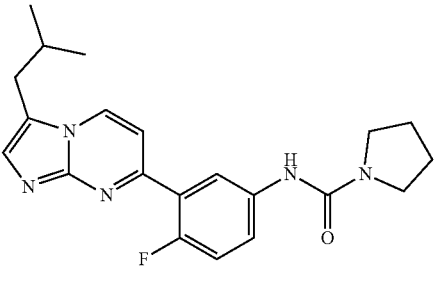<br>N-(4-fluoro-3-(3-isobutylimidazo[1,2-a]pyrimidin-7-yl)phenyl)pyrrolidine-1-carboxamide | $^1$H NMR (400 MHz, DMSO-$d_6$) δ 9.37 (d, J = 7.2 Hz, 1H), 8.49 (s, 1H), 8.43 (dd, J = 7.0, 2.7 Hz, 1H), 8.16 (s, 1H), 7.94 (d, J = 6.2 Hz, 1H), 7.76-7.69 (m, 1H), 7.38 (dd, J = 11.2, 9.1 Hz, 1H), 3.40 (t, J = 6.6 Hz, 4H), 2.89 (d, J = 7.1 Hz, 2H), 2.07 (dt, J = 13.5, 6.7 Hz, 1H), 1.88 (t, J = 6.5 Hz, 4H), 1.00 (d, J = 6.6 Hz, 6H). m/z = 382 (M + H) |

| Example | Structure Chemical name | Physical data (¹H NMR or MS) |
|---|---|---|
| 18 | 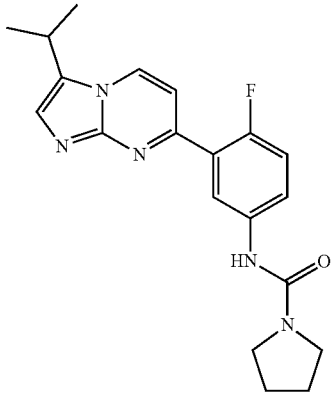<br>N-(4-fluoro-3-(3-isopropylimidazo[1,2-a]pyrimidin-7-yl)phenyl)pyrrolidine-1-carboxamide | ¹H NMR (400 MHz, DMSO-$d_6$) δ 9.37 (d, J = 7.3 Hz, 1H), 8.48 (s, 1H), 8.43 (dd, J = 7.1, 2.8 Hz, 1H), 8.16 (s, 1H), 7.96 (d, J = 6.4 Hz, 1H), 7.83-7.64 (m, 1H), 7.38 (dd, J = 11.3, 9.1 Hz, 1H), 3.50-3.43 (m, 1H), 3.40 (t, J = 6.7 Hz, 4H), 1.88 (t, J = 6.6 Hz, 4H), 1.38 (d, J = 6.8 Hz, 6H). m/z = 368 (M + H). |
| 19 | 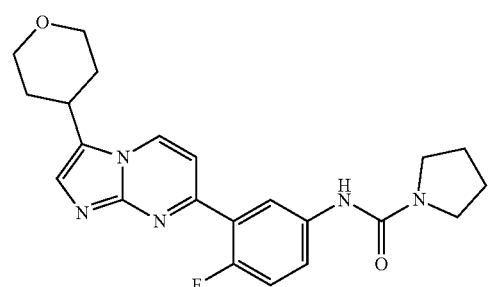<br>N-(4-fluoro-3-(3-(tetrahydro-2H-pyran-4-yl)imidazo[1,2-a]pyrimidin-7-yl)phenyl)pyrrolidine-1-carboxamide | ¹H NMR (400 MHz, DMSO-$d_6$) δ 9.46 (d, J = 7.3 Hz, 1H), 8.49 (s, 1H), 8.39 (dt, J = 18.4, 9.2 Hz, 1H), 8.22-8.08 (m, 1H), 7.94 (d, J = 7.1 Hz, 1H), 7.84-7.69 (m, 1H), 7.35 (dt, J = 36.1, 18.0 Hz, 1H), 4.00 (d, J = 11.1 Hz, 2H), 3.55 (t, J = 10.9 Hz, 2H), 3.51-3.42 (m, 1H), 3.40 (t, J = 6.6 Hz, 4H), 1.98 (d, J = 13.4 Hz, 2H), 1.88 (t, J = 6.5 Hz, 4H), 1.75 (ddd, J = 16.2, 12.4, 4.3 Hz, 2H). m/z = 410 (M + H) |
| 20 | 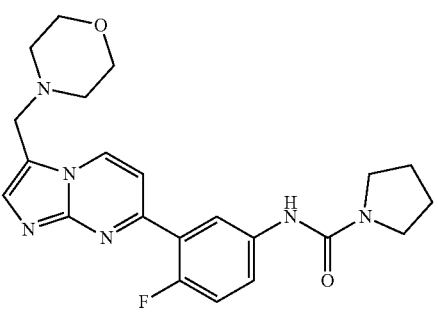<br>N-(4-fluoro-3-(3-(morpholinomethyl)imidazo[1,2-a]pyrimidin-7-yl)phenyl)pyrrolidine-1-carboxamide | ¹H NMR (400 MHz, CDCl₃) δ 8.80 (d, J = 7.2 Hz, 1H), 8.05 (s, 2H), 7.87 (s, 1H), 7.58 (t, J = 11.2 Hz, 1H), 7.19-7.07 (m, 1H), 6.71 (s, 1H), 3.88 (s, 2H), 3.70 (s, 4H), 3.50 (d, J = 6.2 Hz, 4H), 2.49 (s, 4H), 2.09-1.84 (m, 4H). m/z = 425 (M + H) |

| Example | Structure Chemical name | Physical data ($^1$H NMR or MS) |
|---|---|---|
| 21 | 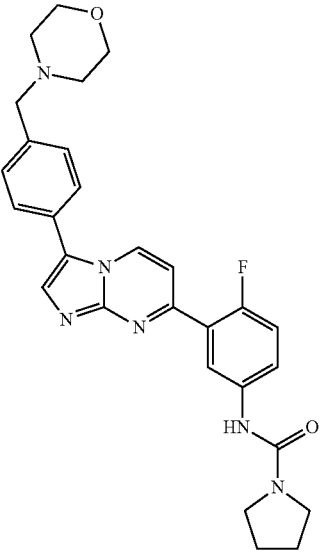<br>N-(4-fluoro-3-(3-(4-(morpholinomethyl)phenyl)imidazo[1,2-a]pyrimidin-7-yl)phenyl)pyrrolidine-1-carboxamide | $^1$H NMR (400 MHz, DMSO-$d_6$) δ 9.11 (d, J = 7.3 Hz, 1H), 8.46 (s, 1H), 8.29 (d, J = 4.7 Hz, 1H), 8.14 (s, 1H), 8.05 (s, 1H), 7.80 (s, 1H), 7.72 (d, J = 8.0 Hz, 1H), 7.52 (d, J = 8.3 Hz, 2H), 7.35-7.20 (m, 1H), 3.59 (d, J = 19.0 Hz, 4H), 3.40 (m, 4H), 2.42 (s, 2H), 1.88 (m, 4H), 1.25 (s, 2H), 0.87 (t, J = 6.7 Hz, 2H). m/z = 501 (M + H) |
| 22 | 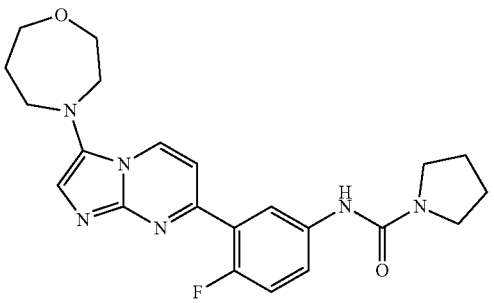<br>N-(3-(3-(1,4-oxazepan-4-yl)imidazo[1,2-a]pyrimidin-7-yl)-4-fluorophenyl)pyrrolidine-1-carboxamide | 1H NMR (400 MHz, DMSO-$d_6$): δ 8.66 (d, 1H), 8.42 (s, 1H), 8.22 (m, 1H), 7.78 (m, 1H), 7.53 (s, 1H), 7.43 (dd, 1H), 7.25 (dd, 1H), 3.85 (m, 4H), 3.38 (m, 4H), 3.30 (m, 4H), 1.98 (m, 2H), 1.87 (m, 4H). m/z = 425 (M + H) |
| 23 | 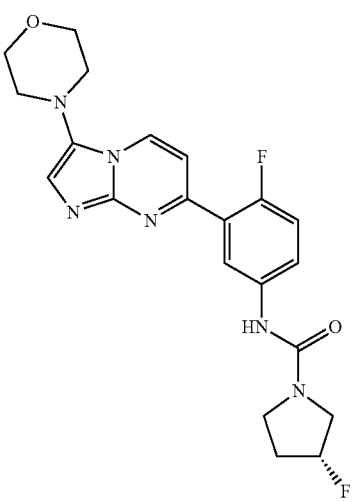<br>(R)-3-fluoro-N-(4-fluoro-3-(3-morpholinoimidazo[1,2-a]pyrimidin-7-yl)phenyl)pyrrolidine-1-carboxamide | $^1$H NMR (400 MHz, DMSO-$d_6$) δ 9.14 (d, J = 7.2 Hz, 1H), 8.62 (s, 1H), 8.38 (dd, J = 7.0, 2.7 Hz, 1H), 7.99 (s, 1H), 7.85 (d, J = 7.4 Hz, 1H), 7.80-7.68 (m, 1H), 7.38 (dd, J = 11.3, 9.0 Hz, 1H), 5.39 (d, J = 53.3 Hz, 1H), 3.95-3.80 (m, 4H), 3.80-3.64 (m, 4H), 3.18-3.01 (m, 4H), 2.30-1.96 (m, 2H). m/z = 428 (M + H) |

| Example | Structure Chemical name | Physical data (¹H NMR or MS) |
|---|---|---|
| 23a | 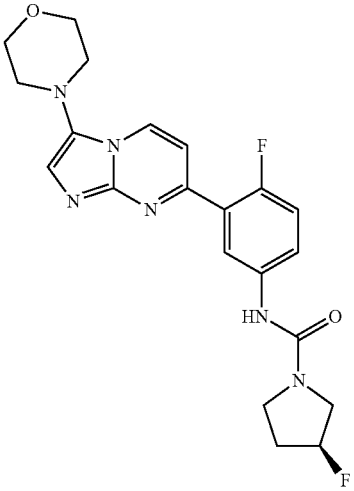<br>(S)-3-fluoro-N-(4-fluoro-3-(3-morpholinoimidazo[1,2-a]pyrimidin-7-yl)phenyl)pyrrolidine-1-carboxamide | ¹H NMR (400 MHz, DMSO-d₆) δ 9.22 (d, J = 7.2 Hz, 1H), 8.79-8.55 (m, 1H), 8.52-8.32 (m, 1H), 8.07 (d, J = 21.2 Hz, 1H), 7.96 (t, J = 18.4 Hz, 1H), 7.85-7.64 (m, 1H), 7.52-7.27 (m, 1H), 5.39 (d, J = 53.2 Hz, 1H), 3.82 (dd, J = 19.0, 14.2 Hz, 4H), 3.75-3.39 (m, 4H), 3.21-3.00 (m, 4H), 2.30-1.99 (m, 2H). m/z = 429 (M + H) |
| 24 | 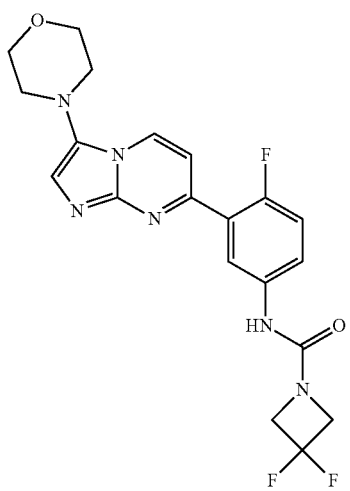<br>3,3-difluoro-N-(4-fluoro-3-(3-morpholinoimidazo[1,2-a]pyrimidin-7-yl)phenyl)azetidine-1-carboxamide | ¹H NMR (400 MHz, MeOD) δ 9.09 (dd, J = 24.7, 14.1 Hz, 1H), 8.47 (dt, J = 25.9, 12.9 Hz, 1H), 8.24-8.00 (m, 1H), 8.00 (s, 1H), 7.81-7.57 (m, 1H), 7.32 (dd, J = 11.3, 9.0 Hz, 1H), 4.62-4.27 (m, 4H), 4.10-3.85 (m, 4H), 3.21 (dd, J = 15.8, 11.1 Hz, 4H). m/z = 432 (M + H) |

| Example | Structure Chemical name | Physical data (¹H NMR or MS) |
|---|---|---|
| 25 | 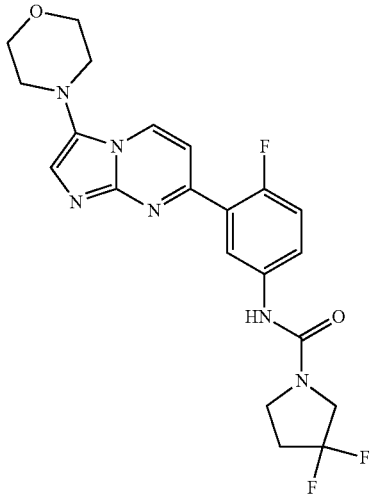<br>3,3-difluoro-N-(4-fluoro-3-(3-morpholinoimidazo[1,2-a]pyrimidin-7-yl)phenyl)pyrrolidine-1-carboxamide | ¹H NMR (400 MHz, MeOD) δ 9.13 (d, J = 7.3 Hz, 1H), 8.47 (dd, J = 6.9, 2.8 Hz, 1H), 8.10 (d, J = 7.2 Hz, 1H), 7.93 (s, 1H), 7.76-7.58 (m, 1H), 7.33 (dd, J = 11.3, 9.0 Hz, 1H), 3.99-3.93 (m, 3H), 3.87 (t, J = 12.9 Hz, 1H), 3.76 (t, J = 7.4 Hz, 1H), 3.19 (dd, J = 14.7, 10.1 Hz, 4H), 2.61-2.42 (m, 2H). m/z = 446 (M + H) |
| 26 | 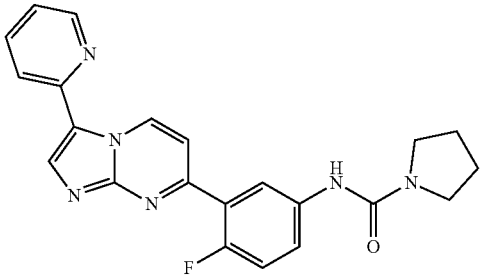<br>N-(4-fluoro-3-(3-(pyridin-2-yl)imidazo[1,2-a]pyrimidin-7-yl)phenyl)pyrrolidine-1-carboxamide | ¹H NMR (400 MHz, MeOD) δ 10.41 (d, J = 7.3 Hz, 1H), 8.92 (s, 1H), 8.70 (d, J = 4.7 Hz, 1H), 8.29 (s, 1H), 7.82 (dt, J = 14.5, 7.8 Hz, 3H), 7.40 (s, 1H), 7.37-7.25 (m, 1H), 7.25-7.03 (m, 1H), 3.28 (s, 4H), 1.91 (s, 4H). m/z = 403 (M + H) |
| 27 | 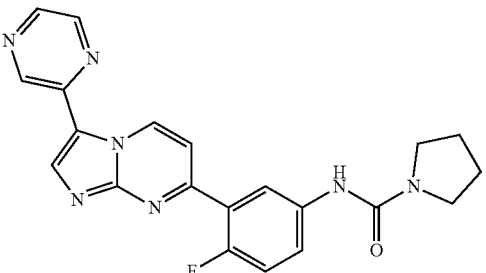<br>N-(4-fluoro-3-(3-(pyrazin-2-yl)imidazo[1,2-a]pyrimidin-7-yl)phenyl)pyrrolidine-1-carboxamide | ¹H NMR (400 MHz, CDCl₃) δ 10.13 (d, J = 7.4 Hz, 1H), 9.16 (s, 1H), 8.66-8.60 (m, 1H), 8.57 (s, 1H), 8.49 (d, J = 2.6 Hz, 1H), 8.20-8.13 (m, 1H), 8.09 (dd, J = 6.5, 2.7 Hz, 1H), 7.79 (d, J = 7.3 Hz, 1H), 7.16 (dd, J = 11.4, 9.1 Hz, 1H), 6.65 (s, 1H), 3.53 (t, J = 6.6 Hz, 4H), 2.01 (d, J = 6.3 Hz, 4H). m/z = 404 (M + H) |

| Example | Structure Chemical name | Physical data (¹H NMR or MS) |
|---|---|---|
| 28 | 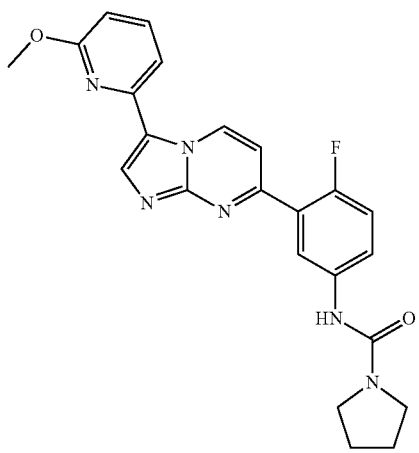<br>N-(4-fluoro-3-(3-(6-methoxypyridin-2-yl)imidazo[1,2-a]pyrimidin-7-yl)phenyl)pyrrolidine-1-carboxamide hydrochloride | 1H NMR (400 MHz, DMSO-$d_6$): δ 10.20 (d, J = 7.1 Hz, 1H), 8.72 (br s, 1H), 8.46 (s, 1H), 8.38-8.35 (m, 1H), 7.87 (t, J = 7.8 Hz, 1H), 7.82-7.79 (m, 2H), 7.69 (d, J = 7.3 Hz, 1H), 7.34-7.29 (m, 1H), 6.82 (d, J = 8.1 Hz, 1H), 4.06 (s, 3H), 2.69-2.65 (m, 2H), 2.35-2.31 (m, 2H), 1.91-1.84 (m, 4H). m/z = 433 (M + H) |
| 29 | 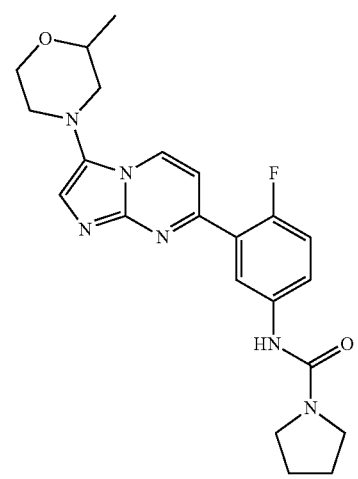<br>N-(4-fluoro-3-(3-(2-methylmorpholino)imidazo[1,2-a]pyrimidin-7-yl)phenyl)pyrrolidine-1-carboxamide | ¹H NMR (400 MHz, DMSO-$d_6$): δ 9.14 (d, J = 7.1 Hz, 1H), 8.49 (s, 1H), 8.39 (dd, J = 7.1, 2.7 Hz, 1H), 7.99 (s, 1H), 7.85 (d, J = 7.0 Hz, 1H), 7.80-7.70 (m, 1H), 7.36 (dd, J = 11.2, 9.1 Hz, 1H), 3.94 (d, J = 9.8 Hz, 1H), 3.81 (dd, J = 17.7, 8.9 Hz, 2H), 3.39 (t, J = 6.6 Hz, 4H), 3.20 (dd, J = 25.4, 11.6 Hz, 2H), 2.93 (td, J = 11.5, 3.1 Hz, 1H), 2.64 (dd, J = 20.1, 9.9 Hz, 1H), 1.87 (t, J = 6.5 Hz, 4H), 1.13 (dd, J = 14.1, 6.3 Hz, 3H). m/z = 425 (M + H) |

| Example | Structure Chemical name | Physical data (¹H NMR or MS) |
|---|---|---|
| 30 | 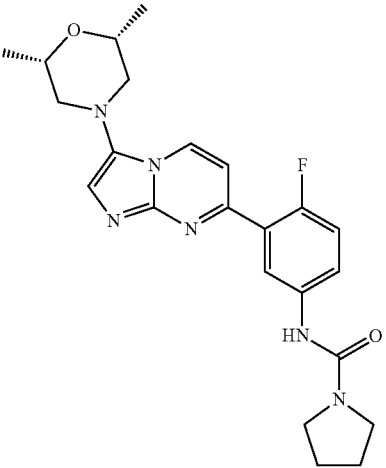<br>N-(3-(3-((2S,6R)-2,6-dimethylmorpholino)imidazo[1,2-a]pyrimidin-7-yl)-4-fluorophenyl)pyrrolidine-1-carboxamide | ¹H NMR (400 MHz, MeOD) δ 9.11 (d, J = 7.3 Hz, 1H), 8.47 (dd, J = 6.9, 2.8 Hz, 1H), 8.09 (d, J = 6.7 Hz, 1H), 7.90 (s, 1H), 7.72-7.57 (m, 1H), 7.42-7.23 (m, 1H), 4.14-3.88 (m, 2H), 3.51 (t, J = 6.7 Hz, 4H), 3.27 (d, J = 10.7 Hz, 2H), 2.72-2.65 (m, 2H), 2.01 (s, 4H), 1.25 (t, J = 5.3 Hz, 6H). m/z = 439 (M + H) |
| 31 | 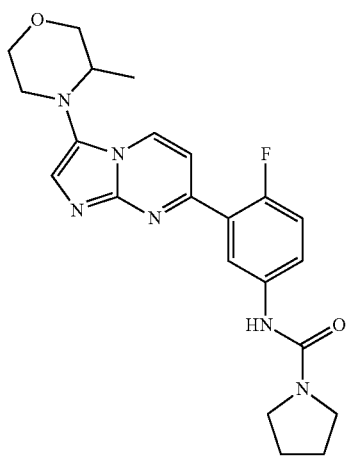<br>N-(4-fluoro-3-(3-(3-methylmorpholino)imidazo[1,2-a]pyrimidin-7-yl)phenyl)pyrrolidine-1-carboxamide | ¹H NMR (400 MHz, MeOD) δ 9.17 (d, J = 7.2 Hz, 1H), 8.47 (dd, J = 6.9, 2.8 Hz, 1H), 8.18-8.02 (m, 2H), 7.71-7.55 (m, 1H), 7.31 (dd, J = 11.4, 9.0 Hz, 1H), 4.06-3.81 (m, 4H), 3.63-3.43 (m, 4H), 3.43-3.37 (m, 1H), 3.31-3.21 (m, 1H), 3.21-3.07 (m, 1H), 2.01 (d, J = 6.6 Hz, 4H), 0.98 (t, J = 17.7 Hz, 3H). m/z = 425 (M + H) |

| Example | Structure Chemical name | Physical data (¹H NMR or MS) |
|---|---|---|
| 32 | 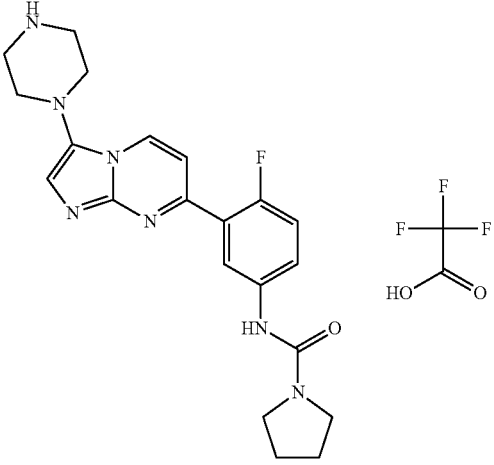<br>N-(4-fluoro-3-(3-(piperazin-1-yl)imidazo[1,2-a]pyrimidin-7-yl)phenyl)pyrrolidine-1-carboxamide 2,2,2-trifluoroacetate | ¹H NMR (400 MHz, DMSO-$d_6$) δ 9.11 (d, J = 7.1 Hz, 1H), 8.90 (s, 2H), 8.47 (s, 1H), 8.37 (dd, J = 7.0, 2.6 Hz, 1H), 8.01 (s, 1H), 7.92-7.64 (m, 2H), 7.35 (dd, J = 11.2, 9.1 Hz, 1H), 3.49-3.31 (m, 8H), 3.31 (s, 4H), 1.88 (t, J = 6.6 Hz, 4H). m/z = 410 (M + H). |
| 33 | 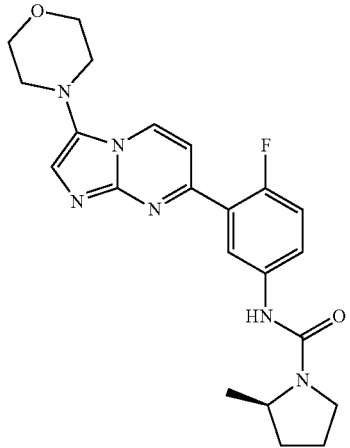<br>(R)-N-(4-fluoro-3-(3-morpholinoimidazo[1,2-a]pyrimidin-7-yl)phenyl)-2-methylpyrrolidine-1-carboxamide | ¹H NMR (400 MHz, MeOD) δ 9.12 (d, J = 7.3 Hz, 1H), 8.47 (dd, J = 6.9, 2.8 Hz, 1H), 8.09 (d, J = 6.6 Hz, 1H), 7.92 (s, 1H), 7.63 (ddd, J = 8.9, 4.3, 2.9 Hz, 1H), 7.31 (dd, J = 11.3, 8.9 Hz, 1H), 4.25-4.09 (m, 1H), 4.08-3.87 (m, 4H), 3.68-3.52 (m, 1H), 3.48 (dd, J = 17.5, 7.8 Hz, 1H), 3.19 (dd, J = 14.6, 10.0 Hz, 4H), 2.20-2.03 (m, 2H), 2.03 (s, 1H), 1.72 (s, 1H), 1.29 (t, J = 11.5 Hz, 3H). m/z 425 (M + H) |

| Example | Structure Chemical name | Physical data (¹H NMR or MS) |
|---|---|---|
| 33a | 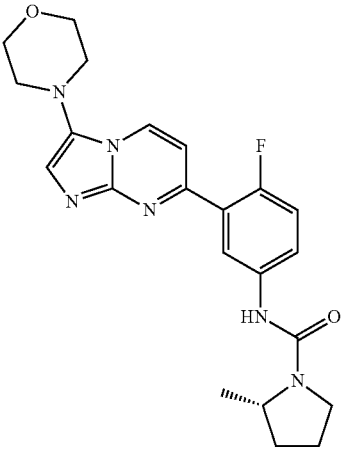<br>(S)-N-(4-fluoro-3-(3-morpholinoimidazo[1,2-a]pyrimidin-7-yl)phenyl)-2-methylpyrrolidine-1-carboxamide | ¹H NMR (400 MHz, MeOD) δ 9.11 (d, J = 7.3 Hz, 1H), 8.46 (dd, J = 6.9, 2.8 Hz, 1H), 8.08 (d, J = 7.0 Hz, 1H), 7.91 (s, 1H), 7.70-7.55 (m, 1H), 7.31 (dd, J = 11.4, 9.0 Hz, 1H), 4.24-4.07 (m, 1H), 4.03-3.86 (m, 4H), 3.69-3.54 (m, 1H), 3.48 (dd, J = 17.6, 7.7 Hz, 1H), 3.26-3.11 (m, 4H), 2.11 (dd, J = 7.0, 3.6 Hz, 2H), 2.06-1.93 (m, 1H), 1.71 (s, 1H), 1.29 (t, J = 11.4 Hz, 3H). m/z = 425 (M + H). |
| 34 | 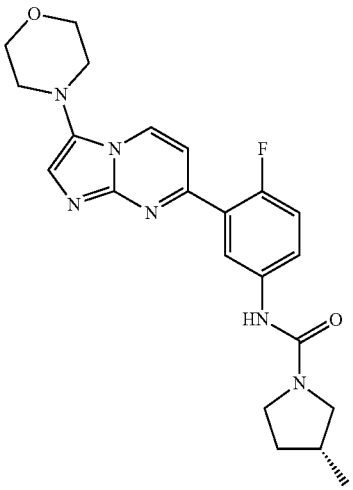<br>(R)-N-(4-fluoro-3-(3-morpholinoimidazo[1,2-a]pyrimidin-7-yl)phenyl)-3-methylpyrrolidine-1-carboxamide | ¹H NMR (400 MHz, DMSO-d₆) δ 9.17 (d, J = 7.2 Hz, 1H), 8.45 (d, J = 14.0 Hz, 1H), 8.43 (s, 1H), 8.04 (s, 1H), 7.88 (d, J = 6.8 Hz, 1H), 7.78-7.66 (m, 1H), 7.36 (dd, J = 11.3, 9.1 Hz, 1H), 3.93-3.74 (m, 4H), 3.60 (dd, J = 9.8, 7.5 Hz, 1H), 3.57-3.44 (m, 1H), 3.35 (dd, J = 17.1, 8.9 Hz, 1H), 3.19-3.01 (m, 4H), 3.01-2.82 (m, 1H), 2.28 (dd, J = 21.7, 13.8 Hz, 1H), 2.01 (d, J = 6.3 Hz, 1H), 1.65-1.40 (m, 1H), 1.06 (d, J = 6.6 Hz, 3H). m/z = 425 (M + H). |

| Example | Structure Chemical name | Physical data (¹H NMR or MS) |
| --- | --- | --- |
| 34a | 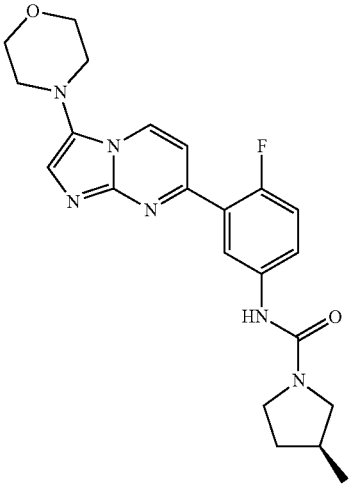<br>(S)-N-(4-fluoro-3-(3-morpholinoimidazo[1,2-a]pyrimidin-7-yl)phenyl)-3-methylpyrrolidine-1-carboxamide | ¹H NMR (400 MHz, DMSO-d₆) δ 9.19 (d, J = 7.1 Hz, 1H), 8.47 (s, 1H), 8.42 (dd, J = 7.1, 2.7 Hz, 1H), 8.06 (s, 1H), 7.89 (d, J = 6.4 Hz, 1H), 7.82-7.69 (m, 1H), 7.37 (dd, J = 11.2, 9.1 Hz, 1H), 3.88-3.80 (m, 4H), 3.60 (dd, J = 9.8, 7.2 Hz, 1H), 3.56-3.46 (m, 1H), 3.35 (dd, J = 16.9, 8.9 Hz, 1H), 3.16-3.05 (m, 4H), 2.98-2.86 (m, 1H), 2.36-2.18 (m, 1H), 2.09-1.97 (m, 1H), 1.51 (td, J = 17.5, 8.8 Hz, 1H), 1.06 (d, J = 6.6 Hz, 3H). m/z = 425 (M + H). |
| 35 | 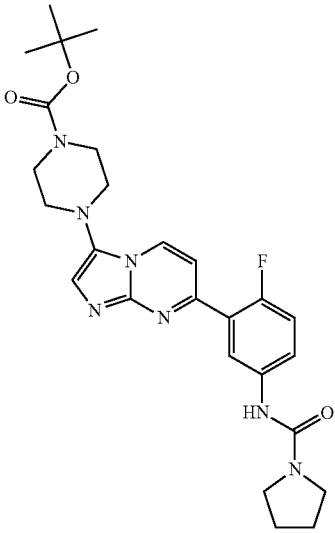<br>tert-butyl 4-(7-(2-fluoro-5-(pyrrolidine-1-carboxamido)phenyl)imidazo[1,2-a]pyrimidin-3-yl)piperazine-1-carboxylate | ¹H NMR (400 MHz, DMSO-d₆) δ 8.75 (d, J = 7.2 Hz, 1H), 8.43 (s, 1H), 8.21 (d, J = 7.0 Hz, 1H), 7.78 (s, 1H), 7.52 (s, 1H), 7.44 (d, J = 5.2 Hz, 1H), 7.34-7.19 (m, 1H), 3.56 (s, 4H), 3.38 (d, J = 6.7 Hz, 4H), 3.14-2.92 (m, 4H), 1.87 (s, 4H), 1.53-1.39 (m, 9H). m/z = 510 (M + H). |

| Example | Structure Chemical name | Physical data (¹H NMR or MS) |
|---|---|---|
| 36 | 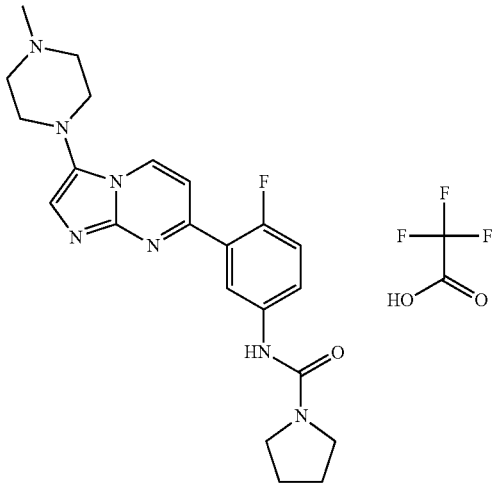<br>N-(4-fluoro-3-(3-(4-methylpiperazin-1-yl)imidazo[1,2-a]pyrimidin-7-yl)phenyl)pyrrolidine-1-carboxamide 2,2,2-trifluoroacetate | ¹H NMR (400 MHz, DMSO-$d_6$) δ 10.08 (s, 1H), 9.11 (d, J = 7.4 Hz, 1H), 9.11 (d, J = 7.4 Hz, 1H), 8.49 (s, 1H), 8.39 (dd, J = 7.1, 2.5 Hz, 1H), 8.07 (s, 1H), 7.86 (d, J = 6.3 Hz, 1H), 7.80-7.67 (m, 1H), 7.36 (dd, J = 11.1, 9.1 Hz, 1H), 3.60 (d, J = 11.3 Hz, 2H), 3.50 (d, J = 11.9 Hz, 2H), 3.36-3.27 (m, 6H), 3.20 (t, J = 11.5 Hz, 2H), 2.93 (s, 3H), 1.88 (s, 4H). m/z = 424 (M + H) |
| 37 | 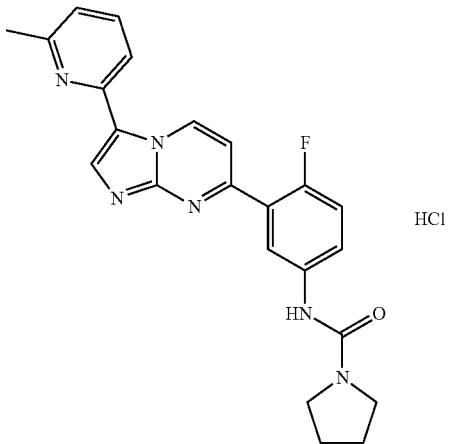<br>N-(4-fluoro-3-(3-(6-methylpyridin-2-yl)imidazo[1,2-a]pyrimidin-7-yl)phenyl)pyrrolidine-1-carboxamide hydrochloride | 1H NMR (400 MHz, DMSO-$d_6$): δ 10.45 (d, J = 7.3 Hz, 1H), 8.85 (br s, 1H), 8.48 (s, 1H), 8.43-8.40 (m, 1H), 7.93-7.86 (m, 3H), 7.80-7.76 (m, 1H), 7.36-7.28 m, 2H), 3.41-3.38 (m, 4H), 2.64 (s, 3H), 1.89-1.85 (m, 4H). m/z = 417 (M + H) |

| Example | Structure Chemical name | Physical data (¹H NMR or MS) |
|---|---|---|
| 38 | 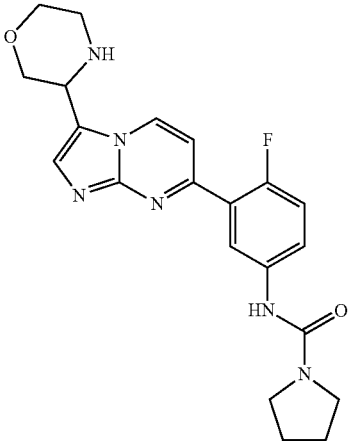<br>N-(4-fluoro-3-(3-(morpholin-3-yl)imidazo[1,2-a]pyrimidin-7-yl)phenyl)pyrrolidine-1-carboxamide | ¹H NMR (400 MHz, MeOD) δ 9.21 (d, J = 7.2 Hz, 1H), 8.33 (dd, J = 6.9, 2.8 Hz, 1H), 8.24 (s, 1H), 7.89 (d, J = 7.1 Hz, 1H), 7.79-7.55 (m, 1H), 7.27 (dd, J = 11.2, 9.0 Hz, 1H), 5.24 (dd, J = 8.2, 3.7 Hz, 1H), 4.39-4.08 (m, 3H), 4.09-3.95 (m, 1H), 3.51 (t, J = 6.7 Hz, 5H), 2.01 (s, 4H). m/z = 411 (M + H) |
| 39 | 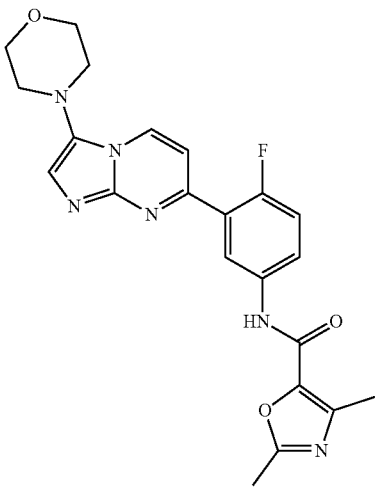<br>N-(4-fluoro-3-(3-morpholinoimidazo[1,2-a]pyrimidin-7-yl)phenyl)-2,4-dimethyloxazole-5-carboxamide | ¹H NMR (400 MHz, MeOD) δ 8.75 (d, J = 7.2 Hz, 1H), 8.46 (d, J = 5.1 Hz, 1H), 7.92 (s, 1H), 7.62 (d, J = 6.7 Hz, 1H), 7.54 (s, 1H), 7.31 (dd, J = 11.1, 9.0 Hz, 1H), 3.94 (s, 4H), 3.15 (s, 4H), 2.57 (s, 3H), 2.48 (s, 3H). m/z = 437 (M + H) |
| 40 | 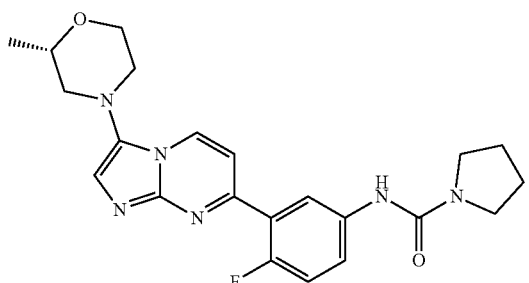<br>(S)-N-(4-fluoro-3-(3-(2-methylmorpholino)imidazo[1,2-a]pyrimidin-7-yl)phenyl)pyrrolidine-1-carboxamide | ¹H NMR (400 MHz, DMSO-d₆) δ 9.14 (d, J = 7.2 Hz, 1H), 8.48 (s, 1H), 8.40 (dd, J = 7.0, 2.7 Hz, 1H), 7.99 (s, 1H), 7.85 (d, J = 7.2 Hz, 1H), 7.80-7.70 (m, 1H), 7.36 (dd, J = 11.2, 9.0 Hz, 1H), 3.94 (d, J = 10.0 Hz, 1H), 3.82 (d, J = 8.8 Hz, 2H), 3.39 (t, J = 6.5 Hz, 4H), 3.20 (dd, J = 25.5, 12.0 Hz, 2H), 2.93 (td, J = 11.5, 3.1 Hz, 1H), 2.63 (s, 1H), 1.88 (t, J = 6.5 Hz, 4H), 1.15 (d, J = 6.3 Hz, 3H). m/z = 425 (M + H) |

-continued

| Example | Structure Chemical name | Physical data (¹H NMR or MS) |
|---|---|---|
| 41 | 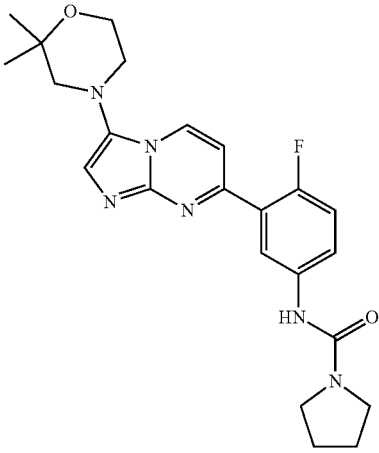  N-(3-(3-(2,2-dimethylmorpholino)imidazo[1,2-a]pyrimidin-7-yl)-4-fluorophenyl)pyrrolidine-1-carboxamide | ¹H NMR (400 MHz, DMSO-$d_6$) δ 9.06 (d, J = 7.3 Hz, 1H), 8.49 (s, 1H), 8.47-8.31 (m, 1H), 7.99 (s, 1H), 7.89 (d, J = 7.0 Hz, 1H), 7.75 (dd, J = 8.4, 3.8 Hz, 1H), 7.36 (dd, J = 11.3, 9.0 Hz, 1H), 3.99-3.82 (m, 2H), 3.39 (t, J = 6.6 Hz, 4H), 3.10-2.94 (m, 2H), 2.90 (s, 2H), 1.87 (d, J = 6.6 Hz, 4H), 1.29 (d, J = 37.2 Hz, 6H). m/z = 439 (M + H) |
| 42 | 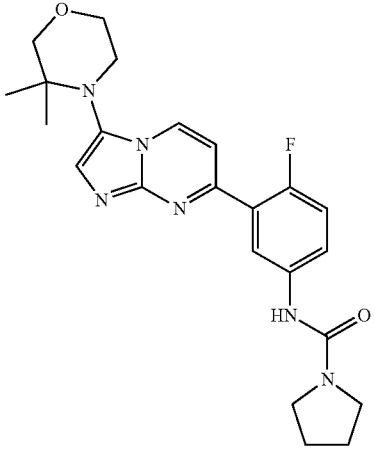  N-(3-(3-(3,3-dimethylmorpholino)imidazo[1,2-a]pyrimidin-7-yl)-4-fluorophenyl)pyrrolidine-1-carboxamide | ¹H NMR (400 MHz, DMSO-$d_6$) δ 9.29 (d, J = 7.2 Hz, 1H), 8.49 (s, 1H), 8.42 (dt, J = 18.5, 9.3 Hz, 1H), 8.28 (s, 1H), 7.91 (d, J = 6.2 Hz, 1H), 7.84-7.67 (m, 1H), 7.37 (dd, J = 11.2, 9.0 Hz, 1H), 3.97 (s, 4H), 3.55 (s, 2H), 3.39 (t, J = 6.6 Hz, 4H), 1.88 (t, J = 6.6 Hz, 4H), 1.06 (d, J = 88.0 Hz, 6H). m/z = 439 (M + H) |
| 43 | 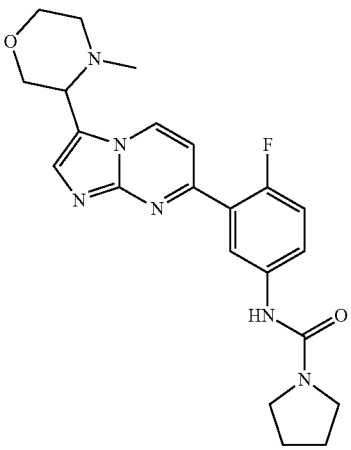  N-(4-fluoro-3-(3-(4-methylmorpholin-3-yl)imidazo[1,2-a]pyrimidin-7-yl)phenyl)pyrrolidine-1-carboxamide | ¹H NMR (400 MHz, DMSO-$d_6$) δ 9.29 (d, J = 7.3 Hz, 1H), 8.43 (s, 1H), 8.23 (dd, J = 7.1, 2.8 Hz, 1H), 7.79 (s, 2H), 7.47 (d, J = 5.2 Hz, 1H), 7.27 (dd, J = 11.4, 9.0 Hz, 1H), 3.87 (d, J = 11.0 Hz, 1H), 3.81-3.67 (m, 3H), 3.39 (t, J = 6.6 Hz, 3H), 2.89 (d, J = 11.9 Hz, 1H), 2.68 (s, 1H), 2.34 (s, 2H), 2.02 (s, 3H), 1.87 (s, 4H). m/z = 425 (M + H) |

| Example | Structure Chemical name | Physical data (¹H NMR or MS) |
|---|---|---|
| 44 | 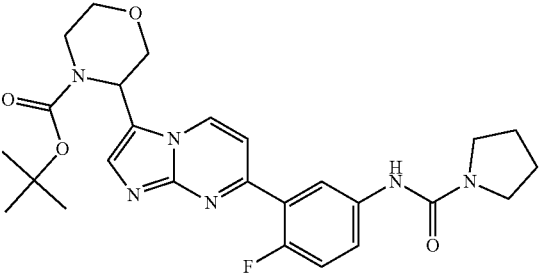<br>tert-butyl 3-(7-(2-fluoro-5-(pyrrolidine-1-carboxamido)phenyl)imidazo[1,2-a]pyrimidin-3-yl)morpholine-4-carboxylate | ¹H NMR (400 MHz, DMSO-d₆) δ 9.13 (d, J = 6.9 Hz, 1H), 8.46 (d, J = 14.0 Hz, 1H), 8.36 (d, J = 6.9 Hz, 1H), 8.25 (s, 1H), 7.96 (s, 1H), 7.87-7.67 (m, 1H), 7.46-7.26 (m, 1H), 5.65 (s, 1H), 4.22 (d, J = 12.5 Hz, 1H), 4.06-3.81 (m, 2H), 3.70 (d, J = 13.9 Hz, 1H), 3.55 (t, J = 10.5 Hz, 1H), 3.40 (t, J = 6.5 Hz, 4H), 3.20-3.00 (m, 1H), 1.88 (s, 42H), 1.44 (s, 9H). m/z = 511 (M + H) |
| 45 | 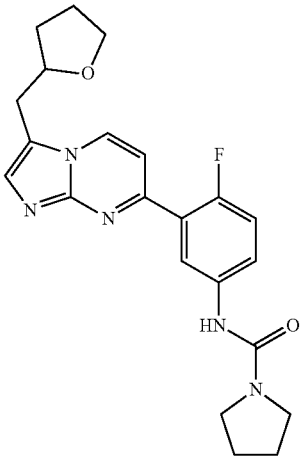<br>N-(4-fluoro-3-(3-((tetrahydrofuran-2-yl)methyl)imidazo[1,2-a]pyrimidin-7-yl)phenyl)pyrrolidine-1-carboxamide | ¹H NMR (400 MHz, MeOD) δ 9.30 (d, J = 7.3 Hz, 1H), 8.45 (dd, J = 6.9, 2.7 Hz, 1H), 8.09 (d, J = 7.1 Hz, 1H), 8.04 (s, 1H), 7.73-7.60 (m, 1H), 7.30 (dd, J = 11.3, 9.0 Hz, 1H), 4.27 (qd, J = 7.6, 3.7 Hz, 1H), 3.90 (dd, J = 14.9, 6.8 Hz, 1H), 3.81-3.68 (m, 1H), 3.51 (t, J = 6.7 Hz, 4H), 3.41 (dt, J = 9.3, 4.9 Hz, 1H), 3.22 (dd, J = 15.7, 7.8 Hz, 1H), 2.20 (tt, J = 15.3, 7.6 Hz, 1H), 2.05-1.92 (m, 4H), 1.94 (d, J = 6.8 Hz, 1H), 1.92-1.84 (m, 1H), 1.76 (ddd, J = 16.1, 12.1, 7.8 Hz, 1H). m/z = 410 (M + H). |
| 46 | 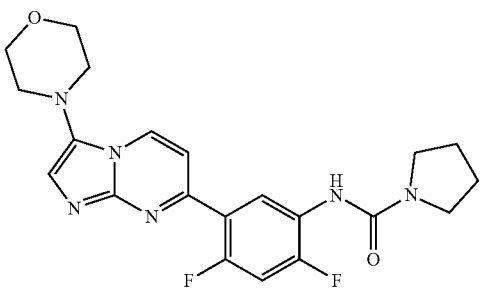<br>N-(2,4-difluoro-5-(3-morpholinoimidazo[1,2-a]pyrimidin-7-yl)phenyl)pyrrolidine-1-carboxamide | 1H NMR (400 MHz, DMSO-d₆): δ 8.76 (m, 1H), 8.20 (m, 1), 8.07 (s, 1H), 7.53 (s, 1H), 7.45 (m, 3H), 3.82 (m, 4H), 3.38 (m, 4H), 3.08 (m, 4H), 1.87 (m, 4H). m/z = 429 (M + H) |

| Example | Structure Chemical name | Physical data ($^1$H NMR or MS) |
|---|---|---|
| 47 | 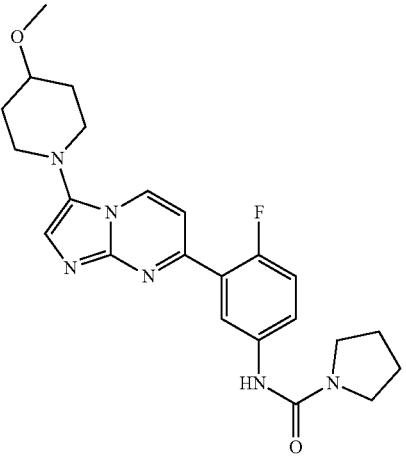<br>N-(4-fluoro-3-(3-(4-methoxypiperidin-1-yl)imidazo[1,2-a]pyrimidin-7-yl)phenyl)pyrrolidine-1-carboxamide | 1H NMR (400 MHz, DMSO-$d_6$, 80° C.): δ 8.60 (d, J = 7.1 Hz, 1H), 8.20-8.18 (m, 2H), 7.77-7.74 (m, 1H), 7.45 (s, 1H), 7.41-7.39 (m, 1H), 7.23-7.18 (m, 1H), 3.47-3.40 (m, 6H), 3.25-3.30 (m, 2H), 3.02 (s, 1H), 2.96-2.90 (m, 2H), 2.08-1.97 (m, 2H), 1.94-1.82 (m, 5H), 1.78-1.70 (m, 2H). m/z = 439 (M + H) |
| 48 | 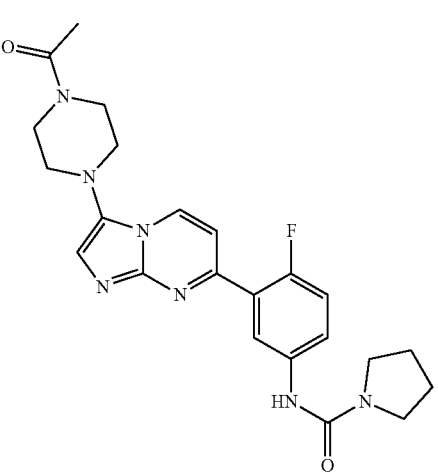<br>N-(3-(3-(4-acetylpiperazin-1-yl)imidazo[1,2-a]pyrimidin-7-yl)-4-fluorophenyl)pyrrolidine-1-carboxamide | 1H NMR (400 MHz, DMSO-$d_6$): δ 8.78 (d, J = 7.1 Hz, 1H), 8.41 (s, 1H), 8.21 dd, J = 2.8, 7.1 Hz, 1H), 7.80-7.76 (m, 1H), 7.52 (s, 1H), 7.48-7.44 (m, 1H), 7.25 (dd, J = 11.1, 9.1 Hz, 1H), 3.70-3.63 (m, 4H), 3.43-3.35 (m, 4H), 3.07-2.98 (m, 4H), 2.07 (s, 3H), 1.88-1.84 (m, 4H). m/z = 452 (M + H) |

| Example | Structure Chemical name | Physical data (¹H NMR or MS) |
|---|---|---|
| 49 | 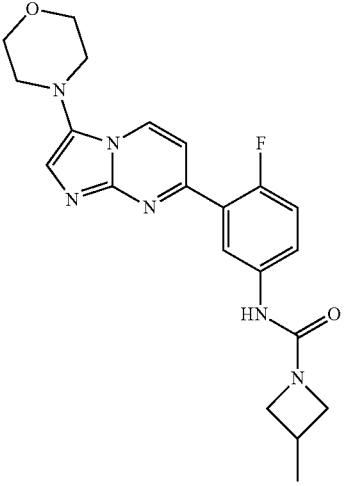<br>N-(4-fluoro-3-(3-morpholinoimidazo[1,2-a]pyrimidin-7-yl)phenyl)-3-methylazetidine-1-carboxamide | ¹H NMR (400 MHz, DMSO-d$_6$) δ 9.16 (d, J = 7.2 Hz, 1H), 8.72 (s, 1H), 8.34 (dt, J = 34.2, 17.0 Hz, 1H), 8.03 (s, 1H), 7.86 (d, J = 6.7 Hz, 1H), 7.80-7.64 (m, 1H), 7.37 (dd, J = 11.2, 9.1 Hz, 1H), 4.09 (t, J = 8.1 Hz, 2H), 3.99-3.72 (m, 3H), 3.54 (dd, J = 8.0, 5.6 Hz, 2H), 3.19-2.99 (m, 4H), 2.77-2.57 (m, 1H), 1.34-1.06 (m, 3H). m/z = 411 (M + H) |
| 50 | 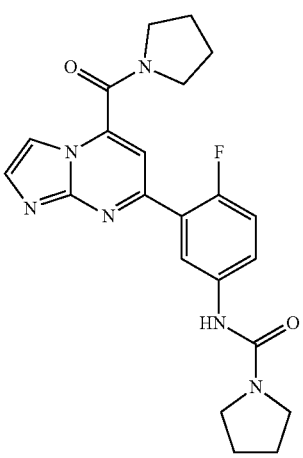<br>N-(4-fluoro-3-(5-(pyrrolidine-1-carbonyl)imidazo[1,2-a]pyrimidin-7-yl)phenyl)pyrrolidine-1-carboxamide | 1H NMR (400 MHz, DMSO-d$_6$): δ 8.43 (s, 1H), 8.23 (d, J = 7.1, 2.8 Hz, 1H), 7.97-7.93 (m, 1H), 7.90-7.87 (m, 1H), 7.83-1.79 (m, 1H), 7.63-7.59 (m, 1H), 7.30-7.25 (m, 1H), 3.63-3.59 (m, 2H), 3.53-3.50 (m, 2H), 3.40-3.37 (m, 4H), 1.97-1.81 (m, 8H). m/z = 423 (M + H) |

| Example | Structure Chemical name | Physical data (¹H NMR or MS) |
|---|---|---|
| 51 | 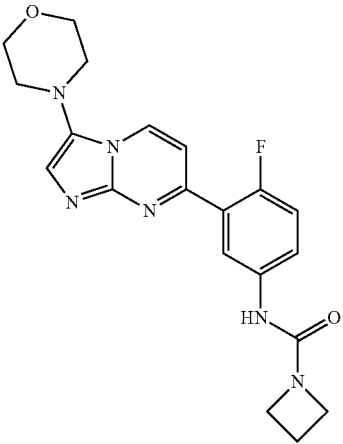<br>N-(4-fluoro-3-(3-morpholinoimidazo[1,2-a]pyrimidin-7-yl)phenyl)azetidine-1-carboxamide | ¹H NMR (400 MHz, DMSO-d₆) δ 9.15 (d, J = 7.1 Hz, 1H), 8.73 (s, 1H), 8.54-8.24 (m, 1H), 8.02 (s, 1H), 7.85 (d, J = 6.9 Hz, 1H), 7.79-7.66 (m, 1H), 7.50-7.27 (m, 1H), 3.98 (t, J = 7.5 Hz, 4H), 3.83 (d, J = 4.3 Hz, 4H), 3.09 (s, 4H), 2.30-2.07 (m, 2H). m/z = 397 (M + H) |
| 52 | 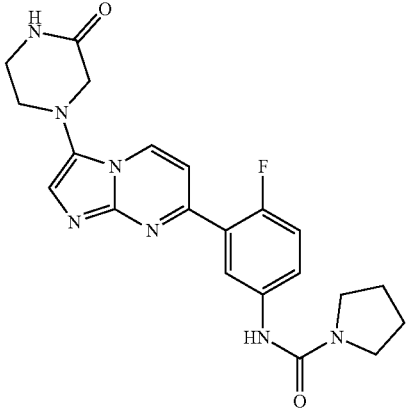<br>N-(4-fluoro-3-(3-(3-oxopiperazin-1-yl)imidazo[1,2-a]pyrimidin-7-yl)phenyl)pyrrolidine-1-carboxamide | 1H NMR (400 MHz, DMSO-d₆): δ 8.75 (d, J = 7.1 Hz, 1H), 8.41 (s, 1H), 8.20 (dd, J = 2.8, 7.1 Hz, 1H), 8.02 (br s, 1H), 7.80-7.76 (m, 1H), 7.55 (s, 1H), 7.42 (dd, J = 2.0, 7.1 Hz, 1H), 7.28-7.23 (m, 1H), 3.68 (s, 2H), 3.40-3.37 (m, 6H), 3.23-3.20 (m, 2H), 1.88-1.84 (m, 4H). m/z = 424 (M + H) |
| 53 | 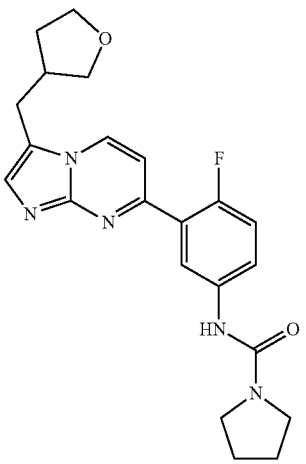<br>N-(4-fluoro-3-(3-((tetrahydrofuran-3-yl)methyl)imidazo[1,2-a]pyrimidin-7-yl)phenyl)pyrrolidine-1-carboxamide | ¹H NMR (400 MHz, DMSO-d₆) δ 9.33 (d, J = 7.2 Hz, 1H), 8.49 (s, 1H), 8.40 (dd, J = 7.0, 2.7 Hz, 1H), 8.14 (s, 1H), 7.91 (d, J = 7.2 Hz, 1H), 7.82-7.68 (m, 1H), 7.36 (dd, J = 11.1, 9.1 Hz, 1H), 3.91-3.76 (m, 2H), 3.69 (dd, J = 15.4, 7.6 Hz, 1H), 3.49-3.33 (m, 5H), 3.05 (d, J = 7.4 Hz, 2H), 2.69 (dt, J = 13.7, 6.9 Hz, 1H), 2.09 (dt, J = 13.2, 7.7 Hz, 1H), 1.88 (t, J = 6.4 Hz, 4H), 1.64 (dt, J = 13.9, 7.2 Hz, 1H). m/z = 410 (M + H). |

| Example | Structure Chemical name | Physical data (¹H NMR or MS) |
|---|---|---|
| 54 | 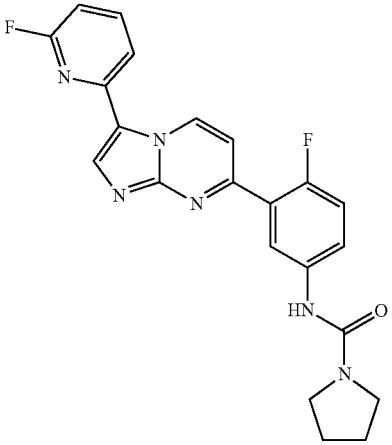<br>N-(4-fluoro-3-(3-(6-fluoropyridin-2-yl)imidazo[1,2-a]pyrimidin-7-yl)phenyl)pyrrolidine-1-carboxamide hydrochloride | ¹H NMR (400 MHz, DMSO-d₆) δ 10.11 (d, J = 7.3 Hz, 1H), 8.94 (s, 1H), 8.49 (s, 1H), 8.38 (dd, J = 7.1, 2.5 Hz, 1H), 8.18 (q, J = 8.1 Hz, 1H), 8.09-8.07 (m, 1H), 7.91 (d, J = 7.3 Hz, 1H), 7.82-7.78 (m, 1H), 7.36-7.31 (m, 1H), 7.20 (dd, J = 8.1, 2.0 Hz, 1H), 4.92-4.48 (br, 1H), 3.41-3.38 (m, 4H), 1.89-1.85 (m, 4H). m/z = 421 (M + H). |
| 55 | 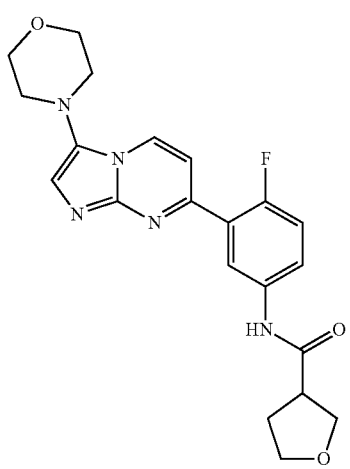<br>N-(4-fluoro-3-(3-morpholinoimidazo[1,2-a]pyrimidin-7-yl)phenyl)tetrahydrofuran-3-carboxamide | ¹H NMR (400 MHz, DMSO-d₆) δ 10.29 (br s, 1H), 8.76 (d, J = 7.1 Hz, 1H), 8.33-8.30 (m, 1H), 7.84-7.80 (m, 1H), 7.52 (s, 1H), 7.42 (dd, J = 7.1, 2.0 Hz, 1H), 7.37-7.32 (m, 1H), 3.97-3.93 (m, 1H), 3.82-3.69 (m, 8H), 3.05-3.03 (m, 4H), 2.12-2.07 (m, 2H). m/z = 412 (M + H). |

| Example | Structure Chemical name | Physical data ($^1$H NMR or MS) |
|---|---|---|
| 56 | 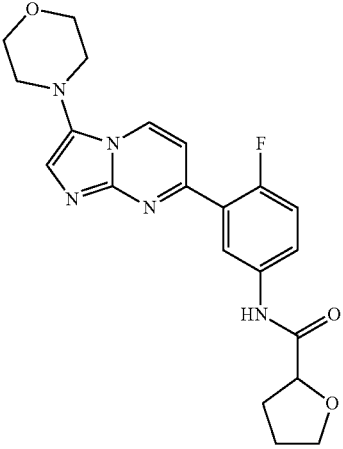<br>N-(4-fluoro-3-(3-morpholinoimidazo[1,2-a]pyrimidin-7-yl)phenyl)tetrahydrofuran-2-carboxamide | $^1$H NMR (400 MHz, DMSO-$d_6$) δ 9.96 (br s, 1H), 8.76 (d, J = 7.3 Hz, 1H), 8.44-8.41 (m, 1H), 7.90-7.86 (m, 1H), 7.52 (s, 1H), 7.41 (dd, J = 7.1, 2.3 Hz, 1H), 7.37-7.32 (m, 1H), 4.40 (dd, J = 8.3, 5.6 Hz, 1H), 4.04-3.98 (m, 1H), 3.86-3.80 (m, 5H), 3.05-3.03 (m, 4H), 2.26-2.17 (m, 1H), 2.04-1.96 (m, 1H), 1.91-1.84 (m, 2H). m/z = 412 (M + H). |
| 57 | 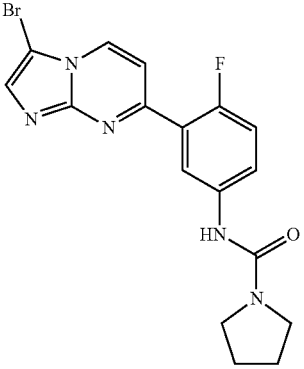<br>N-(3-(3-bromoimidazo[1,2-a]pyrimidin-7-yl)-4-fluorophenyl)pyrrolidine-1-carboxamide | $^1$H NMR (400 MHz, DMSO-$d_6$) δ 8.88 (d, J = 7.3 Hz, 1H), 8.44 (br s, 1H), 8.25 (dd, J = 7.1, 2.8 Hz, 1H), 7.97 (s, 1H), 7.83-7.79 (m, 1H), 7.59 (dd, J = 7.3, 1.8 Hz, 1H), 7.28 (dd, J = 11.3, 9.1 Hz, 1H), 3.41-3.36 (m, 4H), 1.88-1.84 (m, 4H). |

The following compound can be prepared by processes analogous to those described above: N-(4-fluoro-3-(3-(pyrrolidin-1-yl)imidazo[1,2-a]pyrimidin-7-yl)phenyl)pyrrolidine-1-carboxamide

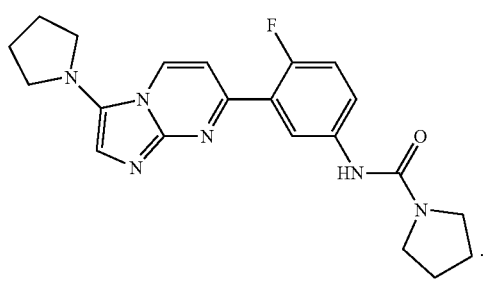 [SMILES: O=C(Nc1ccc(F)c(-c2ccn3c(N4CCCC4)cnc3n2)c1)N1CCCC1]

Biological Activity

Assay 1. Intramacrophage *Leishmania donovani* Assay

The intramacrophage *Leishmania* assay was performed using a modified version of the method described in De Rycker et al. (Antimicrob Agents Chemother. 2013 July; 57(7):2913-22. Comparison of a high-throughput high-content intracellular *Leishmania donovani* assay with an axenic amastigote assay. De Rycker M, Hallyburton I, Thomas J, Campbell L, Wyllie S, Joshi D, Cameron S, Gilbert I H, Wyatt P G, Frearson J A, Fairlamb A H, Gray D W.). Procedure: 350 nl of compound was pre-dispensed into 384 well sterile intermediary plates. For single point screening, amphotericin B was added to all wells of column 24 as a positive control (final concentration 2 μM) and DMSO to column 23. For potency determinations, ten-point, one in three dilution curves were created with the highest concentration being 50 μM and on each plate a control curve of amphotericin B was included. Controls were as follows: columns 11 and 12: DMSO, columns 23 and 24: amphotericin B (final concentration 2 μM). To the intermediary plates, 35 μl of THP-1 media was added and plates were shaken for >5 min to ensure complete mixing. THP-1 cells (8,000 per well, 50 μl) were plated into black clear-bottom 384 well plates (Corning) in presence of 20 nM PMA. After 20 min at RT, the plates were incubated at 37° C. under 5%

$CO_2$ in a humidified incubator for 75 h. The cells were then washed with 450 µl sterile phosphate buffered saline (PBS) supplemented with 1 mM $CaCl_2$, 0.5 mM $MgCl_2$, 0.1% (w/v) bovine serum albumin (PBS-A) and amastigotes were added to all wells at a multiplicity of infection of 5 (40,000 amastigotes per well). After 40 min at RT, plates were returned to the incubator. Amastigotes were incubated in the presence of THP-1 macrophages for 16 h. Any remaining extracellular amastigotes were subsequently removed with an overflow wash of 1 mL PBS-A per well (wash buffer is being aspirated from the top of the well as it is being dispensed) followed by addition of 25 µl of the compound pre-dilutions using a Fluidx Ipette-pro pipetting station. The final dilution of each compound was 200-fold. Plates were incubated for 96 h and then washed (250 µl PBS-A) and fixed (4% (v/v) formaldehyde-PBS, 30 min, RT). After fixation, the wells were washed with 250 µl PBS, stained (10 µg/mL DAPI, 0.4 µg mL-1 HCS Cellmask Deep Red in PBS+0.1% (v/v) Triton X-100, 30 min, RT) and washed with 250 µl PBS. Finally, PBS+0.05% (v/v) thimerosal was added to the wells, the plates were sealed and imaged on a high-content microscope (GE IN Cell 2000) using a 10× objective. Image analysis was carried out with GE IN Cell Analyzer 1000 Workstation using the "Multi Target Analysis" module. Settings for segmentation were as follows: nuclei: minimum area: 142.384 µm2, sensitivity: 81, method: top-hat; cells: characteristic area: 2500 µm2, sensitivity: 60, method: multiscale top-hat; organelles (amastigotes): granule size 1-3, 3 scales, sensitivity: 90, detection in entire cell. For each well, i) THP-1 cell count (cytotoxicity readout) and ii) average number of amastigotes per cell (potency readout) were calculated, both in terms of $pEC_{50}$ values.

Results of the Intramacrophaqe *Leishmania donovani* Assay (Assay 1)

Examples 1-22, 23a, 24-27, 29-36, 38-44, 46-50 and 52 were tested in the Intramacrophage *Leishmania donovani* assay.

Examples 1-10, 12, 13, 17-19, 21, 22, 24, 26, 27, 29-31, 33, 34, 34a, 35, 39-44 and 47 were found to have a $pEC_{50}$ value between 5.0 and 6.6 against *Leishmania donovani*. Examples 11, 15, 16, 20, 25, 36, 38 and 49 were found to have a $pEC_{50}$ value of between 4.7 and 4.9 and Examples 14, 23a, 32, 33a, 46, 48, 50 and 52 were found to have a $pEC_{50}$ value of less than 4.3. All examples tested were found to show cytotoxicity against THP-1 cells with a $pEC_{50}$ value of 4.4 or lower. Example 4 was found to have a $pEC_{50}$ value against *Leishmania donovani* of 5.8 and to show cytotoxicity against THP-1 cells with a $pEC_{50}$ of less than 4.3.

The following compounds were also tested in Assay 1 and were found to have a $pEC_{50}$ value against *Leishmania donovani* of less than 4.3:
N-(4-cyano-3-(3-morpholinoimidazo[1,2-a]pyrimidin-7-yl)phenyl)pyrrolidine-1-carboxamide, N-(4-fluoro-3-(3-morpholinoimidazo[1,2-a]pyrimidin-7-yl)phenyl)-3,3-dimethylazetidine-1-carboxamide, N-(4-fluoro-3-(3-morpholinoimidazo[1,2-a]pyrimidin-7-yl)phenyl)-3,3-dimethylpyrrolidine-1-carboxamide, N-(4-fluoro-3-(3-morpholinoimidazo[1,2-a]pyrimidin-7-yl)phenyl)-2,2-dimethylpyrrolidine-1-carboxamide and N-(4-fluoro-2-methyl-5-(3-morpholinoimidazo[1,2-a]pyrimidin-7-yl)phenyl)pyrrolidine-1-carboxamide.

Assay 2. *Trypanosoma cruzi* Intracellular Assay

Compounds were dispensed into black 384-well assay plates (Greiner) by acoustic dispensing (LabCyte ECHO). For potency determinations, eleven-point, one in three dilution curves were generated, with a top concentration of 50 µM. H9C2 rat cardiomyocytes cells were dispensed in T225 tissue culture flasks and after 4 hours they were infected during 18 hours with *T. cruzi* trypomastigotes in the same T225 tissue culture flasks at a multiplicity of infection of 1. Next, any remaining free trypomastigotes were washed away with PBS and the infected H9C2 cells were harvested by trypsinisation. The infected H9C2 cells were then plated into 384-well plates containing the compounds to be tested, at 2500 cells per well in DMEM media with 2% FBS, 1% Penicillin/Streptomicin, 2 mM L-Glutamine, 1 mM Na Pyruvate and 25 mM HEPES. After 72 h incubation at 37° C. in presence of 5% $CO_2$, the plates were fixed and stained with 4% formaldehyde and 2 µM Draq5 for 3 hours at room temperature. The plates were imaged on a Perkin Elmer Opera high-content imaging system using a 20× air objective. Images were analyzed using the Acapella building blocks system (Perkin Elmer). The image analysis algorithm first identified the H9C2 nuclei followed by demarcation of the cytoplasm and identification of intracellular amastigotes. This algorithm reported mean number of parasites per H9C2 cell, the percentage of infected H9C2 cells and the total number of H9C2 cells.

Results of the *Trypanosoma cruzi* Intracellular Assay (Assay 2)

Examples 1-5, 7-42 and 44-51 were tested in the *Trypanosoma cruzi* intracellular assay and were found to have a $pEC_{50}$ value against *Trypanosoma cruzi* between 5.3 and 8.2, except examples 23a and 33a, which were found to have a $pEC_{50}$ value of 4.5 and 4.9 respectively. All Examples tested were found show cytotoxicity against RnH9c2 cells with a $pEC_{50}$ below 4.3, except Examples 7, 17, 19, 26, 28 and 37, which were found to show cytotoxicity against RnH9c2 cells with a $pEC_{50}$ of 4.7, 5.3, 4.4, 4.4, 5.1 and 4.6 respectively. Example 4 was found to have a $pEC_{50}$ value against *Trypanosoma cruzi* of 7.4 and to show cytotoxicity against RnH9c2 cells with a $pEC_{50}$ of <4.3.

Assay 3. *Trypanosoma brucei* Cell Growth Inhibition Assay

Measurement of the ability of the compounds to inhibit trypanosome (*T. b. brucei*, BSF427, VSG118) cell growth was performed using a modification of the cell viability assay previously described by Raz et al. (Raz B.; Iten M.; Grether-Buhler Y.; Kaminski R.; Brun R. The Alamar Blue assay to determine drug sensitivity of African trypanosomes (*T. b. rhodesiense* and *T. b. gambiense*) in vitro. Acta Trop. 1997, 68, 139-147). Compounds were dissolved in DMSO at a top concentration of 10 mM and serially diluted in half log steps to achieve a range of final assay concentrations of 50 µM to 0.5 nM. Compound at each concentration (200-fold final) was added to clear 96-well tissue culture plates in a volume of 1 µL. Then 2000 cells per well in relevant growth medium (HMI-9T for *T. brucei*, a modification of HMI-9 as described by Hurumi et al. (Hirumi H.; Hirumi K. Continuous cultivation of *Trypanosoma brucei* blood stream forms in a medium containing a low concentration of serum-protein without feeder cell-layers. J. Parasitol. 1989, 75, 985-989.) where 0.2 mM 2-mercaptoethanol was replaced with 0.056 mM thiolglycerol, and MEM with 10% FBS for MRC5) were then added to columns 1-11 of the plates in a volume of 199 µL. To column 12, 200 µL of medium was added to provide a no cells control. Plates were then incubated at 37° C. in an atmosphere of 5% $CO_2$ for 69 h, before the addition of 20 µL of 500 µM rezasurin solution, and a further incubation period of 4 h. Plates were then read on a BioTek flx800 fluorescent plate reader, and percentage inhibition was compared to the maximum and minimum assay controls. Concentration effect curves were fitted using nonlinear regression using XLFit 4.2 and $EC_{50}$ values determined.

Results of the *Trypanosoma Brucei* Cell Growth Inhibition Assay (Assay 3)

Examples 1-5, 7-8, 11-15, 18 and 20 were tested in the *Trypanosoma brucei* cell growth inhibition assay.

All Examples tested were found to have a $pEC_{50}$ value of between 6.2 and 8.2 *Trypanosoma brucei*, Example 4 was found to have a $pEC_{50}$ value of 8.0 against *Trypanosoma brucei*.

Assay 4. Solubility Assay—ChemiLuminescent Nitrogen Detection (CLND)

I. Compounds

A 10 mM DMSO stock solution of the compound was prepared.

Solvents and Buffers

Organic solvents of HPLC grade were used. Ultra pure water (Milli-Q grade) was used. Buffers were prepared with ultra pure water and filtered using 0.45µ cameo filters.

Aqueous Buffer Solution:

Phosphate Buffer Saline (PBS) @ pH 7.4 was prepared from Sigma dry powder packs, P-3813. Each one was diluted to 1 liter with deionised water. The pH was checked before the solution was used II. Procedures.

a) DMSO concentration was measured. DMSO blanks and ondansetron and caffeine standards were added to the plate (column 12, A, B, C, & D for the blanks and E, F, G, & H for the standards). Plates were covered with foil. When the UV and CLND detectors baselines appeared to be stable, the CLND was zeroed.
b) Once DMSO concentration measurements were complete, a filtration plate was prepared from each parent plate by diluting 5 µl of the 10 mM DMSO stock solution to 100 L with pH7.4 PBS.
c) After the plates were prepared, they were covered with a plate lid and left to incubate for 1 h at room temperature.
d) Sample was filtered using MILLIPORE MultiScreen Solubility (MSSLBPC10) Filtration Plates, to NUNC V well plates. The filter plate was removed and the NUNC plate was sealed with a power seal plate seal.
e) HPLC/CLND instruments were set up and left to equilibrate. Mobile phases (MeOH:$H_2O$ 1:1, flow rate: 0.2 ml/min, sensitivity z10, Gain High). The samples were run.
f) The assay curve fit was done by linear regression and solubility values were reported in µM.

Results of the Solubility Assay (CLND)

Examples 1-5, 12-42 and 44-51-were tested in the solubility assay (CLND).

All Examples tested were found to have an average solubility value of 24 µM or higher in this assay, except Example 28, which was found to have an average solubility value of <1 µM. Example 4 was found to have an average solubility value of >444 µM.

Assay 5. *Leishmania donovani* Intracellular Assay

Compounds were dispensed into black 384-well assay plates (Greiner) by acoustic dispensing (LabCyte ECHO). For potency determinations, eleven-point, one in three dilution curves were generated, with a top concentration of 50 µM. THP-1 human monocytes cells were dispensed in T225 tissue culture flasks and differentiated using 30 nM of PMA, after 24 hours they were infected overnight using *Leishmania donovani* expressing Green Fluorescent Protein (eGFP) amastigotes in the same T225 tissue culture flasks at a multiplicity of infection of 10. Next, any remaining free amastigotes were washed away with PBS and the infected THP-1 cells were harvested by trypsinisation. The infected cells were then plated into 384-well plates containing the compounds to be tested, at 3000 cells per well in RPMI media with 2% FBS and 25 mM Sodium bicarbonate. After 96 h incubation at 37° C. in presence of 5% $CO_2$, the plates were fixed with 4% formaldehyde for 30 minutes, washed with PBS and stained with 0.1 mg/mL of DAPI for 30 minutes and washed again with PBS. The plates were imaged on a Perkin Elmer Opera high-content imaging system using a 20× air objective with two expositions, one for DAPI stain and other for eGFP. Images were analysed using the Acapella building blocks system (Perkin Elmer). The image analysis algorithm first identified the THP-1 nuclei followed by demarcation of the cytoplasm and identification of intracellular amastigotes. This algorithm reported mean number of parasites per THP-1 cell, the percentage of infected THP-1 cells and the total number of THP-1 cells.

Results of the *Leishmania donovani* Intracellular Assay (Assay 5)

Examples 1-5, 12-37 and 39-51 were tested in the *Leishmania donovani* intracellular assay.

Examples 1-5, 12-13, 17-23, 24-31, 33, 34-37, 39-49 and 51 were found to have a $pEC_{50}$ value between 5.0 and 6.9 against *Leishmania donovani*. Examples 14-16, 32, 33a and 50 were found to have a $pEC_{50}$ value between 4.4 and 4.9 against *Leishmania donovani* while Example 23a was found to have a $pEC_{50}$ value of less than 4.3. All Examples tested were found to show cytotoxicity against THP-1 cells with a $pEC_{50}$ value of less than 4.3, except Examples 2, 3, 5, 16, 26, 28 and 37, which were found to show cytotoxicity with a $pEC_{50}$ value of between 4.3 and 4.9. Example 4 was found to have a $pEC_{50}$ value against *Leishmania donovani* of 6.2 and to show cytotoxicity against THP-1 cells with a $pEC_{50}$ of less than 4.3.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of Formula (I), or a salt thereof,

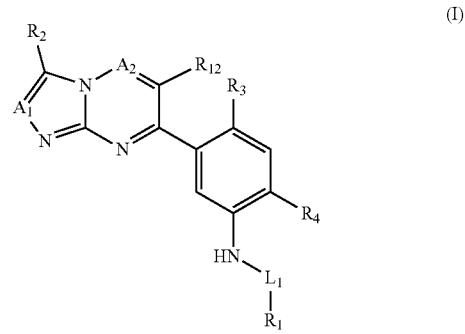

wherein
$A_1$ is CH;
$A_2$ is selected from $CR_{13}$ and N;
$R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$; wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups independently selected from hydroxy, methoxy, $C_1$-$C_3$alkyl and halo;

$L_1$ is a linker group selected from —C(O)— and —S(O)$_n$—, wherein n represents 1 to 2;

$R_3$ is selected from hydrogen, halo, methyl, methoxy and cyano;

$R_4$ is selected from hydrogen, halo, methyl, methoxy and cyano;

$R_2$ is selected from hydrogen, halo, Ar, Cy, X, $NR_{5a}R_{5b}$ and —C(O)—$R_{15}$;

Ar is selected from phenyl and $C_5$-$C_6$heteroaryl, each of which is optionally substituted with one to three groups independently selected from halo and -$L_2$-$R_7$;

$L_2$ is a linker group selected from a bond, —(CH$_2$)$_m$—, —O(CH$_2$)$_m$—, —$C_2$-$C_4$alkenyl-, —$OC_2$-$C_4$alkenyl-, —(CH$_2$)$_p$—NH—(CH$_2$)$_q$—, and —(CH$_2$)$_p$C(O)—(CH$_2$)$_q$—; wherein m represents 1 to 4 and p and q independently represent 0 to 4;

$R_7$ is selected from hydrogen; hydroxy; $NR_{8a}R_{8b}$; $C_4$-$C_7$heterocycloalkyl optionally substituted with one or two $C_1$-$C_3$alkyl groups; $C_3$-$C_7$cycloalkyl; $C_1$-$C_6$alkoxy optionally substituted with one $NR_{14a}R_{14b}$ group; and phenyl optionally substituted with one to three groups independently selected from halo, methoxy and methyl;

Cy is selected from $C_3$-$C_7$cycloalkyl, $C_4$-$C_7$heterocycloalkyl, $C_5$-$C_7$cycloalkenyl and $C_5$-$C_7$heterocycloalkenyl, each of which is optionally substituted with one to three groups independently selected from $C_1$-$C_3$alkyl, $C_1$-$C_3$alkoxy, $C_4$-$C_7$heterocycloalkyl, $NR_{11a}R_{11b}$, =O, —C(O)—$R_{15}$ and —C(O)O—$R_{15}$;

X is selected from $C_1$-$C_6$alkyl, $C_2$-$C_6$alkenyl and $C_1$-$C_6$alkoxy, each of which is optionally substituted with one to three groups independently selected from hydroxy, methoxy, halo, $NR_{13a}R_{13b}$ and $C_4$-$C_7$heterocycloalkyl, wherein $C_4$-$C_7$heterocycloalkyl is optionally substituted with one to three $C_1$-$C_3$alkyl groups;

$R_{5a}$ is selected from hydrogen; $C_1$-$C_6$alkyl optionally substituted with one group selected from Ar and Cy; —C(O)—$R_9$; —C(O)—O$R_9$; and —SO$_2$—$R_9$;

$R_{5b}$ is selected from hydrogen and $C_1$-$C_3$alkyl;

$R_{8a}$ and $R_{8b}$ are independently selected from hydrogen and $C_1$-$C_3$alkyl;

$R_9$ is selected from $C_1$-$C_6$alkyl, $C_3$-$C_7$cycloalkyl, $C_4$-$C_7$heterocycloalkyl, phenyl and $C_5$-$C_6$heteroaryl;

$R_{10a}$ and $R_{10b}$ are independently selected from hydrogen and $C_1$-$C_3$alkyl;

$R_{11a}$ and $R_{11b}$ are independently selected from hydrogen and $C_1$-$C_3$alkyl;

$R_{12}$ is selected from hydrogen, halo and methyl;

$R_{13}$ is selected from hydrogen, $C_1$-$C_3$alkyl, —C(O)—$C_4$-$C_7$heterocycloalkyl, —C(O)—$C_1$-$C_3$alkyl and —C(O)—$C_3$-$C_7$cycloalkyl;

$R_{13a}$ and $R_{13b}$ are independently selected from hydrogen and $C_1$-$C_3$alkyl;

$R_{14a}$ and $R_{14b}$ are independently selected from hydrogen and $C_1$-$C_3$alkyl; and $R_{15}$ is selected from $C_1$-$C_6$alkyl, Ar, $C_3$-$C_7$cycloalkyl and $C_4$-$C_7$heterocycloalkyl.

2. A compound according to claim 1, wherein $R_1$ is $C_4$-$C_7$heterocycloalkyl optionally substituted with one $C_1$-$C_3$alkyl or with one or two halo.

3. A compound according to claim 1, wherein $L_1$ is —C(O)—.

4. A compound according to claim 1, wherein $R_2$ is selected from hydrogen, halo, Ar, Cy, and X.

5. A compound according to claim 1, wherein $R_2$ is Cy and Cy is optionally substituted $C_4$-$C_7$heterocycloalkyl.

6. A compound according to claim 1, wherein $R_3$ is hydrogen or halo and $R_4$ is hydrogen, halo, or methyl.

7. A compound of Formula (I) according to claim 1, which is

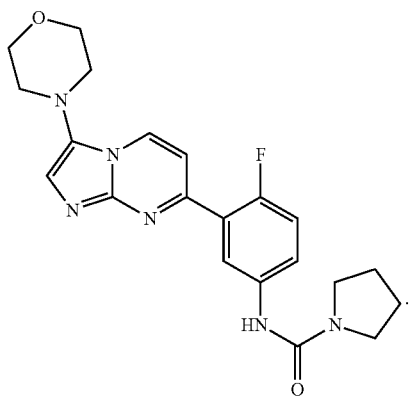 [SMILES: O=C(Nc1ccc(F)c(-c2ccn3c(N4CCOCC4)cnc3n2)c1)N1CCCC1]

8. A compound of Formula (IA), or a salt thereof,

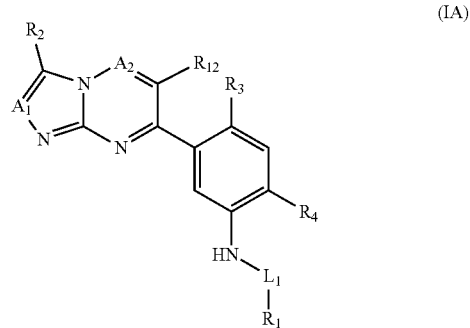

(IA)

wherein $A_1$ is CH;

$A_2$ is selected from $CR_{13}$ and N;

$R_1$ is selected from $C_1$-$C_6$alkyl, $C_3$-$C_7$cycloalkyl, $C_4$-$C_7$heterocycloalkyl, phenyl, $C_5$-$C_6$heteroaryl, $C_1$-$C_6$alkoxy, —$OC_3$-$C_7$cycloalkyl and $NR_{10a}R_{10b}$; wherein $C_3$-$C_7$cycloalkyl, $C_4$-$C_7$heterocycloalkyl, phenyl, $C_5$-$C_6$heteroaryl and —$OC_3$-$C_7$cycloalkyl are optionally substituted with one to three groups selected from hydroxy, methoxy, $C_1$-$C_3$alkyl and halo;

$L_1$ is a linker group selected from —C(O)— and —S(O)$_n$—; wherein n represents 1 to 2;

$R_3$ is selected from hydrogen, halo, methyl, methoxy and cyano;

$R_4$ is selected from hydrogen, halo, methyl, methoxy and cyano;

$R_2$ is selected from hydrogen, halo, Ar, Cy, X and $NR_{5a}R_{5b}$;

Ar is selected from phenyl and $C_5$-$C_6$heteroaryl, each of which is optionally substituted with one to three groups independently selected from $NR_{6a}R_{6b}$ and -$L_2$-$R_7$;

$L_2$ is a linker group selected from a bond, —$(CH_2)_m$—, —$O(CH_2)_m$—, —$C_2$-$C_4$alkenyl- and —$OC_2$-$C_4$alkenyl-; wherein m represents 1 to 4;

$R_7$ is selected from hydrogen, $C_4$-$C_7$heterocycloalkyl, $C_3$-$C_7$cycloalkyl, $C_1$-$C_6$alkoxy, hydroxy and $NR_{8a}R_{8b}$;

Cy is selected from $C_3$-$C_7$cycloalkyl, $C_4$-$C_7$heterocycloalkyl, $C_5$-$C_7$cycloalkenyl and $C_5$-$C_7$heterocycloalkenyl, each of which is optionally substituted with one to three groups independently selected from $C_1$-$C_3$alkyl, $C_4$-$C_7$heterocycloalkyl and $NR_{11a}R_{11b}$;

X is selected from $C_1$-$C_6$alkyl, $C_2$-$C_6$alkenyl and $C_1$-$C_6$alkoxy, each of which is optionally substituted with one to three groups independently selected from hydroxy, methoxy, halo and $C_4$-$C_7$heterocycloalkyl, wherein $C_4$-$C_7$heterocycloalkyl is optionally substituted with one to three $C_1$-$C_3$alkyl groups;

$R_{5a}$ is selected from hydrogen, $C_1$-$C_6$alkyl, —C(O)—$R_9$, —C(O)—$OR_9$ and —$SO_2$—$R_9$;

$R_{5b}$ is selected from hydrogen and $C_1$-$C_3$alkyl;

$R_{6a}$ and $R_{6b}$ are independently selected from hydrogen and $C_1$-$C_3$alkyl;

$R_{8a}$ and $R_{8b}$ are independently selected from hydrogen and $C_1$-$C_6$alkyl;

$R_9$ is selected from $C_1$-$C_6$alkyl, $C_3$-$C_7$cycloalkyl, $C_4$-$C_7$heterocycloalkyl, phenyl and $C_5$-$C_6$heteroaryl;

$R_{10a}$ and $R_{10b}$ are independently selected from hydrogen and $C_1$-$C_3$alkyl;

$R_{11a}$ and $R_{11b}$ are independently selected from hydrogen and $C_1$-$C_3$alkyl;

$R_{12}$ is selected from hydrogen, halo and methyl; and $R_{13}$ is selected from hydrogen and $C_1$-$C_3$alkyl.

9. A compound of Formula (I) according to claim 1, or a pharmaceutically acceptable salt thereof.

10. A pharmaceutical composition comprising (a) a compound of Formula (I) according to claim 1, or a pharmaceutically acceptable salt thereof, and (b) a pharmaceutically acceptable carrier.

11. A combination comprising (a) a compound of Formula (I) according to claim 1, or a pharmaceutically acceptable salt thereof, and (b) at least one additional therapeutic agent.

12. A method of treatment of a parasitic disease selected from Chagas disease, Human African Trypanosomiasis, Animal African trypanosomiasis and leishmaniasis, which method comprises administering to a mammal in need thereof, a therapeutically effective amount of a compound of Formula (I) according to claim 1, or a pharmaceutically acceptable salt thereof.

13. The method of treatment according to claim 12, wherein the mammal is a human.

14. The method of treatment according to claim 12, wherein the leishmaniasis is visceral leishmaniasis.

15. A compound of Formula (IA) according to claim 8, or a pharmaceutically acceptable salt thereof.

16. A pharmaceutical composition comprising (a) a compound of Formula (IA) according to claim 8, or a pharmaceutically acceptable salt thereof, and (b) a pharmaceutically acceptable carrier.

17. A combination comprising (a) a compound of Formula (IA) according to claim 8, or a pharmaceutically acceptable salt thereof, and (b) at least one additional therapeutic agent.

18. A method of treatment of a parasitic disease selected from Chagas disease, Human African Trypanosomiasis, Animal African trypanosomiasis and leishmaniasis, which method comprises administering to a mammal in need thereof, a therapeutically effective amount of a compound of Formula (IA) according to claim 8, or a pharmaceutically acceptable salt thereof.

19. The method of treatment according to claim 18, wherein the mammal is a human.

20. The method of treatment according to claim 18, wherein the leishmaniasis is visceral leishmaniasis.

21. The combination of claim 11, wherein the at least one additional therapeutic agent is selected from the group consisting of an anti-leishmaniasis agent, an anti-parasitic agent, an anti-AIDS agent, an anti-HIV agent, and an anti-TB agent.

22. The combination of claim 17, wherein the at least one additional therapeutic agent is selected from the group consisting of an anti-leishmaniasis agent, an anti-parasitic agent, an anti-AIDS agent, an anti-HIV agent, and an anti-TB agent.

23. The combination of claim 11, wherein the at least one additional therapeutic agent is an anti-leishmaniasis agent selected from the group consisting miltefosine, paromomycin, sodium stibugluconate, meglumine antimoniate, amphotericin B deoxycholate, and liposomal amphotericin B.

24. The combination of claim 17, wherein the at least one additional therapeutic agent is an anti-leishmaniasis agent selected from the group consisting miltefosine, paromomycin, sodium stibugluconate, meglumine antimoniate, amphotericin B deoxycholate, and liposomal amphotericin B.

* * * * *